(12) United States Patent
Noble et al.

(10) Patent No.: US 9,572,981 B2
(45) Date of Patent: Feb. 21, 2017

(54) METHODS AND SYSTEMS FOR CUSTOMIZING COCHLEAR IMPLANT STIMULATION AND APPLICATIONS OF SAME

(71) Applicant: Vanderbilt University, Nashville, TN (US)

(72) Inventors: Jack H. Noble, Nashville, TN (US); Rene H. Gifford, Franklin, TN (US); Robert F. Labadie, Nashville, TN (US); Benoit M. Dawant, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 0 days.

(21) Appl. No.: 14/390,503

(22) PCT Filed: Apr. 3, 2013

(86) PCT No.: PCT/US2013/035076
§ 371 (c)(1),
(2) Date: Oct. 3, 2014

(87) PCT Pub. No.: WO2013/152077
PCT Pub. Date: Oct. 10, 2013

(65) Prior Publication Data
US 2015/0088225 A1 Mar. 26, 2015

Related U.S. Application Data

(60) Provisional application No. 61/619,824, filed on Apr. 3, 2012.

(51) Int. Cl.
*A61N 1/36* (2006.01)
*A61B 5/12* (2006.01)
(Continued)

(52) U.S. Cl.
CPC ............ *A61N 1/36032* (2013.01); *A61B 5/12* (2013.01); *A61B 5/4893* (2013.01);
(Continued)

(58) Field of Classification Search
CPC .............. A61N 1/0541; A61N 1/36032; A61N 1/36185; A61B 5/0033; A61B 5/037;
(Continued)

(56) References Cited

U.S. PATENT DOCUMENTS 6,068,652 A * 5/2000 Cohen ................ A61N 1/36032
600/25
2007/0293785 A1 12/2007 Litvak
(Continued)

FOREIGN PATENT DOCUMENTS

WO 2006118915 A2 11/2006
WO 2007013891 A2 2/2007
WO 2012037305 A1 3/2012

OTHER PUBLICATIONS

Noble et al. "Automatic Identification of Cochlear Implant Electrode Arrays for Post-Operative Assessment." Proc SPIE Int Soc Opt Eng. 2011; 7962: 10.1117/12.878490.*
(Continued)

*Primary Examiner* — Eugene T Wu
(74) *Attorney, Agent, or Firm* — Locke Lord LLP; Tim Tingkang Xia, Esq.

(57) ABSTRACT

One aspect of the invention provides a method for customizing cochlear implant stimulation of a living subject. The cochlear implant includes an electrode array having a plurality of electrodes implanted in a cochlea of the living subject. The method includes determining a position for each of the plurality of electrodes and spiral ganglion nerves that the electrode array stimulates, determining a geometric relationship between neural pathways within the cochlea and
(Continued)

(a)

(b)

(c)

the electrode array implanted therein, and using one or more electrodes of the electrode array to stimulate a group of SG neural pathways of the cochlea based on the location of the one or more electrodes and their geometric relationship with the neural pathways.

20 Claims, 30 Drawing Sheets

(51) Int. Cl.
    *A61B 5/00*     (2006.01)
    *G06T 7/00*     (2006.01)
    *H04R 25/00*     (2006.01)
    *A61N 1/05*     (2006.01)
    *G06F 19/00*     (2011.01)
    *A61B 6/03*     (2006.01)
    *A61B 6/00*     (2006.01)

(52) U.S. Cl.
    CPC ........ *A61N 1/36185* (2013.01); *G06T 7/0024* (2013.01); *G06T 7/0083* (2013.01); *G06T 7/0089* (2013.01); *H04R 25/50* (2013.01); *H04R 25/606* (2013.01); *A61B 6/032* (2013.01); *A61B 6/501* (2013.01); *A61B 6/5235* (2013.01); *A61B 2034/104* (2016.02); *A61B 2034/105* (2016.02); *A61N 1/0541* (2013.01); *G06F 19/3437* (2013.01); *G06T 2207/10081* (2013.01); *G06T 2207/20124* (2013.01); *G06T 2207/20128* (2013.01); *G06T 2207/30052* (2013.01)

(58) Field of Classification Search
    CPC ..... A61B 5/004; A61B 5/0073; A61B 5/0082; A61B 5/4893; A61B 5/742; A61B 5/7425; A61B 5/743
    See application file for complete search history.

(56) References Cited

U.S. PATENT DOCUMENTS

2009/0012580 A1    1/2009    Arnoldner
2010/0070000 A1*    3/2010    Litvak ................ A61N 1/36185
                                                                        607/57
2011/0238176 A1    9/2011    Bradley et al.
2011/0319965 A1*    12/2011    Fridman ............ A61N 1/36032
                                                                          607/57

OTHER PUBLICATIONS

Stakhovskaya et al. "Frequency Map for the Human Cochlear Spiral Ganglion: Implications for Cochlear Implants." J Assoc Res Otolaryngol. Jun. 2007; 8(2): 220-233.*
Noble et al. "Modeling and segmentation of intra-cochlear anatomy in conventional CT." Proc. SPIE 7623, Medical Imaging 2010: Image Processing, 762302 (Mar. 5, 2010); doi:10.1117/12.844747.*
Bonham et al. "Current focusing and steering: Modeling, physiology, and psychophysics." Hear Res. Aug. 2008; 242(1-2): 141-153.*
Noble et al. "Automatic Segmentation of Intra-Cochlear Anatomy in Conventional CT." IEEE Trans Biomed Eng. Sep. 2011; 58(9): 2625-2632.*
Wanna et al. "Assessment of Electrode Placement and Audiologic Outcomes in Bilateral Cochlear Implantation." Otol Neurotol. Apr. 2011; 32(3): 428-432.*
Schuman et al. "Anatomic verification of automatic segmentation algorithms for precise intrascalar localization of cochlear implant electrodes in adult temporal bones using clinically-available computed tomography." Laryngoscope. Nov. 2010; 120(11): 2277-2283.*
Noble et al. "Statistical Shape Model Segmentation and Frequency Mapping of Cochlear Implant Stimulation Targets in CT." Med Image Comput Comput Assist Interv. 2012; 15(Pt 2): 421-428.*
Noble et al. "Image-Guidance Enables New Methods for Customizing Cochlear Implant Stimulation Strategies." Neural Systems and Rehabilitation Engineering, IEEE Transactions on , vol. 21, No. 5, pp. 820-829, Sep. 2013.*
Wise, Nancy. "High Fidelity: Cochlear implant users report dramatically better hearing with new Vanderbilt process." Tuesday, Mar. 5, 2013. <http://news.vanderbilt.edu/2013/03/high-fidelity/>.*
Noble et al. "Clinical Evaluation of an Image-Guided Cochlear Implant Programming Strategy." Audiol Neurotol 2014;19:400-411 (DOI:10.1159/000365273).*
Slides describing Image-Guided cochlear implant programming. <https://www.vanderbilt.edu/CAOS/wp-content/uploads/sites/76/Slideshow-that-describes-some-recent-research-at-Vanderbilt-in-image-guided-cochlear-implant-programming.pdf>. Linked via <http://www.igcip.com/>. No publication date. Accessed Jan. 2, 2016.*
Noble, J. H. et al., Image-guidance enables new methods for customizing cochlear implant stimulation strategies, IEEE Transactions on Neural Systems and Rehabilitation Engineering., Mar. 19, 2013, pp. 1-11; Issue 99, ISSN: 1534-4320.
International Search Report and Written Opinion for Application No. PCT/US2013/035076 dated Jul. 26, 2013.
"Cochlear Implants"National Institute on Deafness and Other Communication Disorders, No. 11-4798, 2011.
Rubenstein, J.T., "How cochlear implants encode speech" Curr Opin Otolaryngol Head Neck Surg. 12(5): 444-8, 2004.
Wilson, B.S., Dorman M.F., "Cochlear implants: Current designs and future possibilities" J. Rehab. Res. Dev. 45(5): 695-730, 2008.
Fu, Q.J., Nogaki G., "Noise susceptibility of cochlear implant users: The role of spectral resolution and smearing" J Assoc Res Otolaryngol. 6(1):19-27, 2005.
Boex C, de Balthasar C., Kos M.I., Pelizzone M., "Electrical field interactions in different cochlear implant systems" J Acoust Soc Am 114:2049-2057, 2003.
Noble, J.H. et al., "Automatic segmentation of intra-cochlear anatomy in conventional CT" IEEE Trans. on Biomedical. Eng., 58(9): 2625-32, 2011.
Noble, J.H.et al., "Statistical Shape Model Segmentation and Frequency Mapping of Cochlear Implant Stimulation Targets in CT", N. Ayache et al. (Eds.): MICCAI 2012, Part II, LNCS 7511, pp. 421-428. 2012.
Noble, J.H., Schuman, A., Wright, C.G., Labadie, R.F., Dawant, B.M., "Automatic Identification of Cochlear Implant Electrode Arrays for Post-Operative Assessment" Proc. of the SPIE conf. on Med. Imag., 7962: 796217, 2011.
Wilson B.S., Finley C.C., Lawson, D.T., Wolford, R.D., Eddington, D.K., Rabinowitz, W.M., "Better speech recognition with cochlear implants" Nature 352, 236-238, 1991.
Stakhovskaya O., Spridhar D., Bonham B.H., Leake P.A., "Frequency Map for the Human Cochlear Spiral Ganglion: Implications for Cochlear Implants" J. Assoc. Res. Otol. 8: 220-33, 2007.
Friesen L.M., Shannon R.V., Baskent D., Wang X., "Speech recognition in noise as a function of the number of spectral channels: Comparison of acoustic hearing and cochlear implants" J. Acoust Soc Am. 110(2): 1150-63, 2001.
Garnham C., O'Driscoll M., Ramsden R., Saeed S., "Speech understanding in noise with a Med-El COMBI 40+ cochlear implant using reduced channel sets" Ear Hear. 23(6): 540-52, 2002.
Zwolan T.A., Collins L.M., Wakefiled G.H., "Electrode discrimination and speech recognition in postlingually deafened adult cochlear implant subjects" J. Acoust. Soc. Am. 102(6): 3673-85, 1997.
Garadat S.N., Zwolan T.A., Pfingst B.E., "Across-site patterns of modulation detection: Relation to speech recognition" J. Acoust. Soc. Am. 131(5): 4030-41, 2012.
Peterson G.E., Lehiste I., "Revised CNC lists for audiotory tests" J. Speech and Hear. Dis. 27: 62-70, 1962.
Spahr A.J., Dorman M.F., Litvak L.M., Van Wie S., Gifford R.H., Loizou P.C., Loiselle L.M., Oakes T., Cook S., "Development and validation of the AzBio sentence lists" Ear Hear. 33(1): 112-7, 2012.

(56) References Cited

OTHER PUBLICATIONS

Bench J., Kowal A., Bamford J., "The BKB (Bamford-Kowal-Bench) sentences lists for partially-hearing children" Br. J. Audiol. 13: 108-12, 1979.
Saoji A.A., Litvak L.M., Spahr A.J., Eddins D.A., "Spectral modulation detection and vowel and consonant identifications in cochlear implant listeners" J. Acoust. Soc. Am. 126 (3): 955-8, 2009.
Henry B.A., Turner C.W., "The resolution of complex spectral patterns by cochlear implant and normal-hearing listeners" J Acoust Soc Am 113(5):2861-73, 2003.
Wilcoxon, F., "Individual comparisons by ranking methods" Biometrics Bulletin 1 (6): 80-83, 1945.
Cox R.M., Alexander G.C., "The abbreviated profile of hearing aid benefit" Ear Hear. 16(2): 176-86, 1995.
Tyler R.S., Preece J.P., Lansing C.R., Otto S.R., Gantz B.J., "Previous experience as a confounding factor in comparing cochlear-implant processing schemes" J. Speech Hear. Res. 29: 282-7, 1986.
Cootes, T.F., Taylor, C.J., Cooper, D.H., Graham, J, "Active Shape Models—Their Training and Application" Comp. Vis. Image Unders. 61(1), 39-59, 1995.
Green, B. F., "The orthogonal approximation of an oblique structure in factor analysis" Psychometrika 17, 429-440, 1952.
Dice, L.R., "Measures of the amount of ecologic association between species" Ecology 26, 297-302, 1945.
Zijdenbos A.P., Dawant B.M., Margolin R., "Morphometric Analysis of White Matter Lesions in MR Images: Method and Validation" IEEE Trans. on Med. Imag. 13(4), 716-724, 1994.
Fechner GT, Elemente der Psychophysik. B. Rand, Ed. The Classical Psychologists (pp. 562-572). Boston: Houghton Mifflin, 1912.
Thornton, A. R., Raffin, M. J., "Speech-discrimination scores modeled as a binomial variable" J Speech Hear Res 21, 507-518, 1978.
Gifford RH, Shallop JK, Peterson AM., "Speech Recognition Materials and Ceiling Effects: Considerations for Cochlear Implant Programs" Audiol Neurotol, 13:193-205, 2008.
Aschendorff A, Kromeier J, Klenzner T, Laszig R, "Quality Control After Insertion of the Nucleus Contour and Contour Advance Electrode in Adults" Ear & Hearing 28, 2007: 75S-79S.
Jethanamest D, Tan CT, Fitzgerald MB, Svirsky MA, "A new software tool to optimize frequency table selection for cochlear implants" Otology & Neurotology 31(8), 2010: 1242-7.
Skinner MW, Holden TA, Whiting BR, Voie AH, Brundsden B, Neely JG, Saxon EA, Hullar TE, Finley CC. "In vivo estimates of the position of advanced bionics electrode arrays in the human cochlea" Ann Otol Rhinol Laryngol Suppl. 197, 2007.: 197:2-24.
Noble JH, Rutherford R, Labadie RF, Majdani O, Dawant BM. "Modeling and segmentation of intra-cochlear anatomy in conventional CT" Proc. of the SPIE conf. on Med. Imag. 7623, 2010: 762302.
Rogers M, Graham J. Robust Active Shape Model Search. Lecture Notes in Computer Science—ECCV 2353, 2002: 517-530.
Asman, A.J. and B.A. Landman, "Robust Statistical Label Fusion through Consensus Level, Labeler Accuracy and Truth Estimation (COLLATE)" IEEE Transactions on Medical Imaging, In press 2011.
GreenWood DD. "A cochlear frequency-position function for several species—29 years later" J. Acoust. Soc. Am. 87 (6):2592-2605, 1990.
Drennan WR, Won JH, Nie K, Jameyson E, Rubinstein JT. (2010). "Sensitivity of psychophysical measures to signal processor modifications in cochlear implant users" Hear Res. 262(1-2):1-8.
Gabrielsson A, Schenkman BN, Hagerman B. (1988), "The effects of different frequency responses on sound quality judgments and speech intelligibility" J Speech Hear Res., 31(2):166-77.
Hinderink JB, Krabbe PF, Van Broek P. (2000), "Development and application of a health-related quality-of-life instrument for adults with cochlear implants: the Nijmegen chochlear implant questionnaire" Otolaryngol Head Neck Surg. 123 (6):756-65.
Won JH, Drennan WR, Nie K, Jameyson EM, Rubinstein JT. (2011), "Acoustic temporal modulation detection and speech perception in cochlear implant listeners" J Acoust Soc Am. 130(1):376-88.
de Bruijne, M., van Ginneken, B., Viergever, M.A., Niessen, W.J.: Adapting active shape models for 3D segmentation of tubular structures in medical images, In: Proc. Inf. Process. Med. Imaging pp. 136-147. Springer (2003).
C. James, K. Albegger, and R. Battmer, et. al, "Preservation of residual hearing with cochlear implantation: How and why," Acta Oto-Laryngologica, 125:5, pp. 481-491, 2005.
E. Erixon, H. Hogstorp, K. Wadin, and H. Rask-Anderson, "Variational anatomy of the human cochlea: implications for cochlear implantation," Otology & Neurotology, 30, pp. 14-22, 2008.
P. Dimopoulos, C. Muren, "Anatomic variations of the cochlea and relations to other temporal bone structures", Acta Radiologica, 31, pp. 439-444, 1990.
D.R. Ketten, M.W. Skinner, G. Wang, et al., "In vivo measure of cochlear length and insertion depth of nucleus aochlear implant electrode arrays," Ann Otol Rhinol Laryngol Suppl., 175, pp. 1-16, 1998.
B. Escude, C. James, O. Dequine, N. Cochard, E. Eter, B. Fraysse, "The size of the cochlea and predictions of insertion depth angles for cochlear implant electrodes," Audiol. Neurootol., 11 Suppl 1, pp. 27-33, 2006.
W. H. Press, B. P. Flannery, S. A. Teukolsky, and W. T. Vetterling, "Numerical Recipes in C," 2nd ed. Cambridge, U.K.: Cambridge Univ. Press, 1992, ch. 10, pp. 412-419.
F. Maes, A. Collignon, D. Vandermeulen, G. Marchal, and P. Suetens, "Multimodality image registration by maximization of mutual information," IEEE Trans Med Imag. 16, pp. 187-198, 1997.
G.K. Rohde, A. Aldroubi, B.M. Dawant, "The adaptive bases algorithm for intensity-based nonrigid image registration," IEEE Trans. Med. Imag., 22, pp. 1470-1479, 2003.
Z. Wu, "Compactly supported positive definite radial functions," Adv. Comput. Math. 4, 283-292, 1995.
C. Studholme, D.L.G. Hill and D.J. Hawkes, "An overlap invariant entropy measure of 3D medical image alignment," Pattern Recognition 32; 1, pp. 71-86, 1999.
Frangi, A.F., Rueckert, D., Schnabel, J.A., Niessen, W.J., "Automatic construction of multiple-object three-dimensional statistical shape models: Application to cardiac modeling," IEEE Trans on Med. Imag., vol. 21, No. 9, pp. 1151-66, 2002.
Arun, K. S., Huang, T. S., and Blostein, S. D., "Least square fitting of two 3-D point sets," IEEE Trans. Patt. Anal. Machine Intell. vol. 9, No. 5, pp. 698-700, 1987.
Schuman TA, Noble JH, Wright CG, Wanna GB, Dawant B, Labadie, RF. "Anatomic Verification of a Novel, Non-rigid Registration Method for Precise Intrascalar Localization of Cochlear Implant Electrodes in Adult Human Temporal Bones Using Clinically-available Computerized Tomography." Laryngoscope, 120 (11), pp. 2277-2283, 2010.
Wanna, G., Noble, J.H., Mcrackan, T., Dawant, B.M., Dietrich, M., Watkins, L, Rivas, A., Schuman, T., Labadie, R., "Assessment of electrode positions and hearing outcome in bilateral cochlear implant patients," Otology & Neurotology, 32 (3), pp. 428-432, 2011.
Finley, C. C., Holden, T. A., Holden, L. K., Whiting, B. R., Chole, R. A., Neely, G. J., Hullar, T.E., & Skinner, M. W. (2008), "Role of electrode placement as a contributor to variability in cochlear implant outcomes" Otology & Neurotology, 29(7), 920-928.
Labadie, R.F., Balachandran, R., Mitchell, J., Noble, J.H., Majdani, O., Haynes, D.S., Bennett, M., Dawant, B.M., Fitzpatrick, J.M., 2010, "Clinical Validation Study of Percutaneous Cochlear Access Using Patient Customized Micro-Stereotactic Frames," Otology & Neurotology, 31(1):94-99.
C. Xu, J. L. Prince, "Snakes, shapes, and gradient vector flow," IEEE Trans. on Image Processing, 7(3): 259-69, 1998.
M. Kass, A. Witkin, D. Terzopoulos, "Snakes: Active Contour Models," Int'l Jour. of Computer Vision, 321-331, 1988.
M.W. Skinner, T.A. Holden, B.R. Whiting, et. al, "In vivo estimates of the position of advanced bionics electrode arrays in the human cochlea," Ann Otol Rhinol Laryngol Suppl., 197:2-24, Apr. 2007.

(56) References Cited

OTHER PUBLICATIONS

A. Aschendorff, J. Kromeier, T. Klenzner, and R. Laszig, "Quality Control After Insertion of the Nucleus Contour and Contour Advance Electrode in Adults", Ear & Hearing, 28, 75S-79S, Apr. 2007.
Fan-Gang Zeng et al., "Cochlear Implants: System Design, Integration, and Evaluation", IEEE Reviews in Biomedical Engineering, vol. 1, Nov. 2008, pp. 115-142.
Bierer, "Probing the Electrode-Neuron Interface with Focused Cochlear Implant Stimulation", Trends in Amplification, Jul. 22, 2010.
European Patent Office, "EP Search Report for EP Application No. 13772589.1", EP, Nov. 26, 2015.

\* cited by examiner

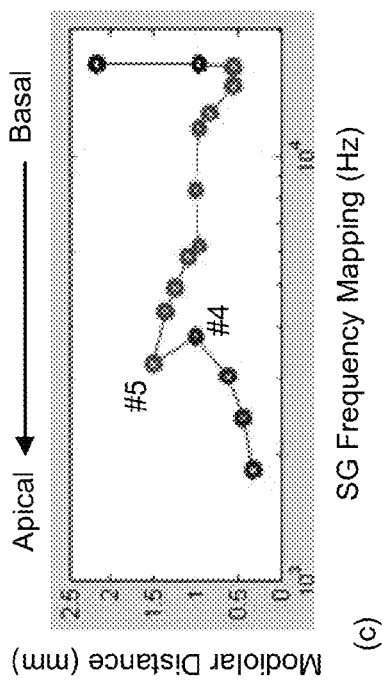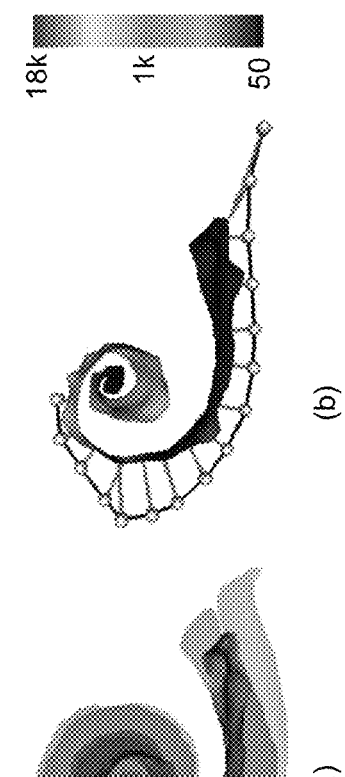
FIG. 1

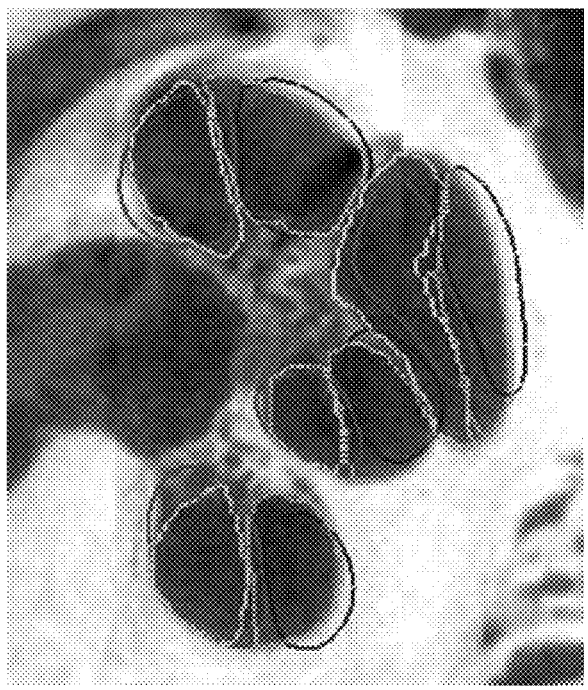
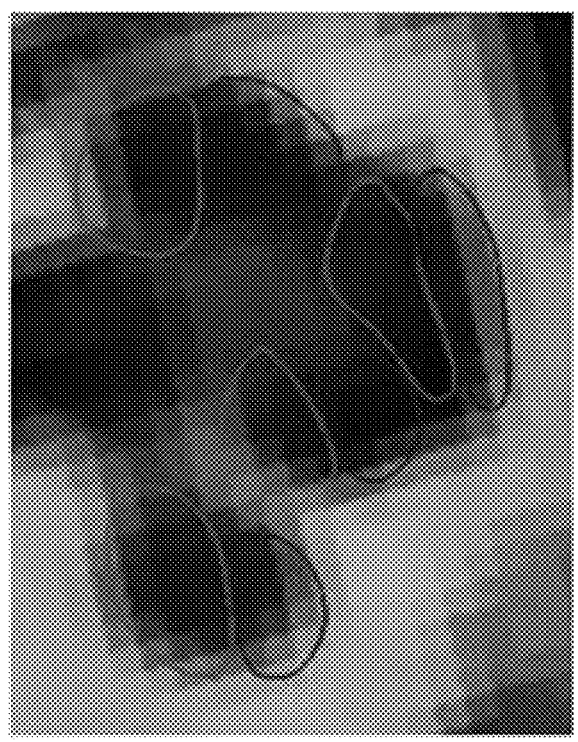
FIG. 2

(1) Establish point correspondence
    a. Rigid and non rigid registration of training volumes to reference volume
    b. Deform training surfaces into reference space
    c. Find closest points from reference to deformed training surfaces (2) Rigid + scaling register original training surfaces to reference surface with point registration (3) Compute modes of variation using eigenanalysis

FIG. 18

(1) Initialize model
    a. Affine and non- rigid registration of atlas to target volume
    b. Project corresponding model points from atlas to target
    c. Fit the model to the points given by registration (2) Search for better solutions
    a. Find an optimal adjustment for each model point
    b. Fit the shape model to the set of adjusted points (3) Iterate (2) until convergence

FIG. 19

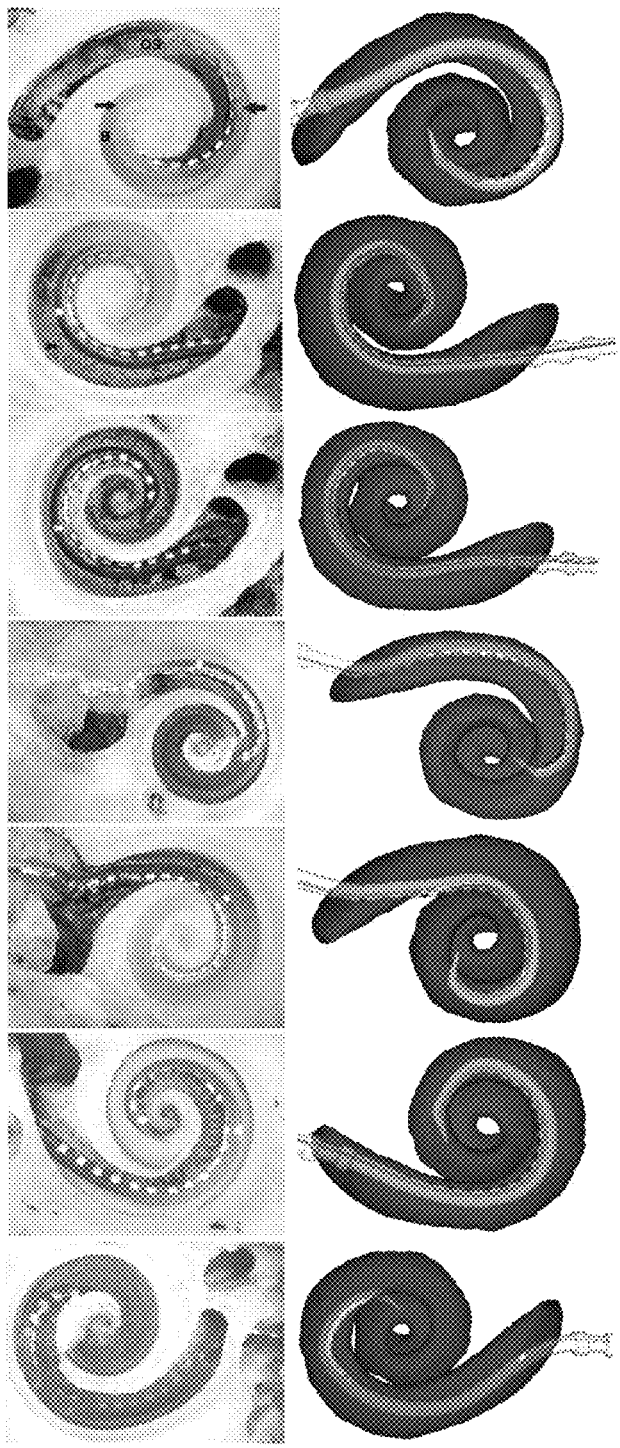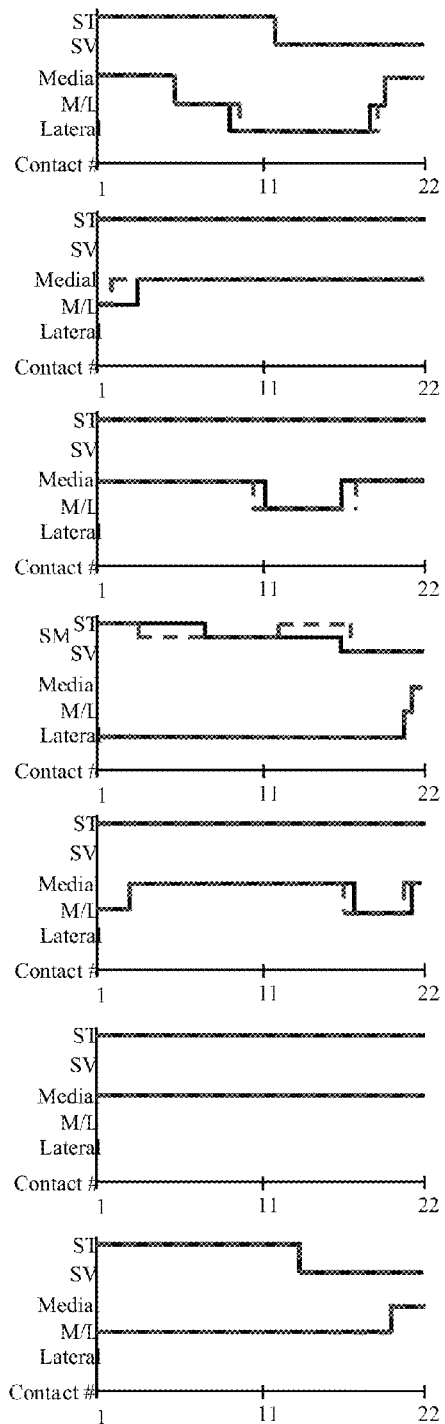
FIG. 31

METHODS AND SYSTEMS FOR CUSTOMIZING COCHLEAR IMPLANT STIMULATION AND APPLICATIONS OF SAME

CROSS-REFERENCE TO RELATED PATENT APPLICATIONS

This application is a U.S. national phase application, under 35 U.S.C. §371, of PCT Patent Application Serial No. PCT/US2013/035076, filed Apr. 3, 2013, which itself claims priority to and the benefit of, pursuant to 35 U.S.C. §119(e), U.S. provisional patent application Ser. No. 61/619,824, filed on Apr. 3, 2012, entitled "SYSTEM AND METHODS OF COCHLEAR IMPLANT MAPPING BASED ON INTRACOCHLEAR POSITION OF ELECTRODE ARRAYS AND APPLICATIONS OF SAME", by Jack H. Noble et al., which is incorporated herein in its entirety by reference.

Some references, which may include patents, patent applications, and various publications, are cited and discussed in the description of this invention. The citation and/or discussion of such references is provided merely to clarify the description of the invention and is not an admission that any such reference is "prior art" to the invention described herein. All references cited and discussed in this specification are incorporated herein by reference in their entireties and to the same extent as if each reference was individually incorporated by reference. In terms of notation, hereinafter, "[n]" represents the nth reference cited in the reference list. For example, [6] represents the 6th reference cited in the reference list, namely, Noble J. H., Labadie R. F., Majdani O., Dawant B. M., "Automatic segmentation of intracochlear anatomy in conventional CT", IEEE Trans. on Biomedical. Eng., 58(9): 2625-32, 2011

STATEMENT AS TO RIGHTS UNDER FEDERALLY-SPONSORED RESEARCH

This invention was made with government support under grant numbers R01DC008408, R01DC009404, R21DC012620 and F31DC009791 awarded by the National Institute on Deafness and Other Communication Disorders, and UL1TR000011 awarded by the National Center for Advancing Translational Sciences. The government has certain rights in the invention.

FIELD OF THE INVENTION

The invention relates generally to image processing, and more particularly to methods and systems for customizing cochlear implant (CI) stimulations by identifying the positions of implanted CI electrodes and the spiral ganglion (SG) nerves they stimulate for individual CI recipients, so as to improve their hearing outcomes without requiring additional surgical procedures.

BACKGROUND INFORMATION

In the natural hearing process, ear anatomy mechanically translates sound into vibrations of the basilar membrane (BM) in the cochlea. These vibrations stimulate nerves connected to the spiral ganglion (SG) and, eventually, the auditory nerve. Researchers have extracted the tonotopic mapping between the frequency of the sound and the SG nerves that are stimulated, i.e., higher frequencies lead to stimulation of more basal SG nerves, whereas, lower frequencies stimulate more apical SG nerves [10].

Cochlear implants (CIs) are surgically implanted neural prosthetic devices used to treat severe-to-profound hearing loss [1]. CIs exploit the natural tonotopy by applying an electric field to more apical (basal) SG nerves to induce perceived lower (higher) frequency sounds. Over the last few decades, the design of CIs has evolved to produce what is arguably the most successful neural prosthesis to date. CIs induce hearing sensation by stimulating auditory nerve pathways within the cochlea using an implanted electrode array. The CI processor, typically worn behind the ear, is programmed to process sound received through a microphone and to send instructions to each electrode. CI programming begins with selection of a general signal processing strategy, e.g., continuous interleaved sampling [9]. Then, the audiologist defines what is referred to as the "MAP," which is the set of CI processor instructions. The MAP is tuned by specifying stimulation levels for each electrode based on measures of the user's perceived loudness and by selecting a frequency allocation table, which defines which electrodes should be activated when specific frequencies are in the detected sound. The number of electrodes in the intracochlear array ranges from 12 to 22, depending on the manufacturer. Electrode activation stimulates spiral ganglion (SG) nerves, the nerve pathways that branch to the cochlea from the auditory nerve (see FIG. 1).

CI devices available today lead to remarkable results in the vast majority of users with average postoperative sentence recognition reaching over 70% correct for unilaterally implanted recipients and over 80% correct for bilateral implant recipients [31]. Despite this success, a significant number of users receive marginal benefit, and restoration to normal fidelity is rare even among the best performers. This is due, in part, to several well-known issues with electrical stimulation that prevent CIs from accurately simulating natural acoustic hearing. Electrode interaction is an example of one such issue that, despite significant improvements made by advances in hardware and signal processing, remains challenging [4, 5]. In natural hearing, a nerve pathway is activated when the characteristic frequency associated with that pathway is present in the incoming sound. Neural pathways are tonotopically ordered by decreasing characteristic frequency along the length of the cochlea, and this precisely tuned spatial organization is well known (see FIG. 1c) [10]. CI electrode arrays are designed such that when placement is optimal, each electrode stimulates nerve pathways corresponding to a pre-defined frequency bandwidth [3]. However, in surgery, the CI electrode array is blindly threaded into the cochlea with its insertion path guided only by the walls of the spiral-shaped intra-cochlear cavities. Since the final positions of the electrodes are generally unknown, the only option when designing the MAP has been to assume the electrodes are optimally situated in the cochlea and use a default frequency allocation table. Because MAP efficacy is sensitive to sub-optimal electrode positioning [2, 3], which can lead to, e.g., electrode channel interactions [4, 5], more effective MAPS could be selected if the positions of the electrodes were known.

It is widely believed that the best hearing restoration outcome can be achieved by stimulating, for a particular sound, the nerves that naturally correspond to the spectrum of that sound. However, this is not currently possible due to the following limitations:

(1) The depth of the implanted array typically falls short of the apical position corresponding to the lowest perceived frequencies. Thus, the lowest frequency nerves are not stimulated, and a frequency shifting artifact is introduced, i.e., each electrode stimulates nerves that correspond to higher frequencies than the ones of the detected sound.

(2) Using the small number of electrodes in the CI array (i.e., 12 to 22) and due to their large size relative to individual nerves, limited spectral resolution is achievable, i.e., an electrode cannot target individual nerves, but rather stimulates nerves corresponding to a wide range of frequencies.

(3) Individual electrodes are positioned at variable depths and perimodiolar distances. Moreover, there has been no technology developed that allows accurate assessment of electrode position relative to stimulation targets in vivo. Depth discrepancies result in a frequency shift artifact. A larger distance to the SG leads to wider current spread from each electrode, further decreasing the spectral resolution.

Therefore, a heretofore unaddressed need exists in the art to address the aforementioned deficiencies and inadequacies.

SUMMARY OF THE INVENTION

In one aspect, the invention relates to a method for determining locations of an electrode array implanted in a cochlea of a living subject and spiral ganglion (SG) nerves that the electrode array stimulates, where the electrode array comprises a plurality of electrodes. In one embodiment, the method includes the steps of identifying an SG neural region that is targeted for stimulation and its corresponding modiolar interface, constructing a tonotopic map of the modiolar interface to have a tonotopically mapped modiolar interface, and identifying the position for each of the plurality of electrodes relative to the tonotopically mapped modiolar interface in vivo.

In one embodiment, the step of identifying the SG neural region comprises the steps of constructing a statistical shape model (SSM) of cochlear anatomy that includes the SG from a set of CT image volumes of cochlea pre-operatively acquired from a number of living subjects.

In one embodiment, the set of CT images of cochlea comprises μCT image volumes of cochlea, where in each μCT image volume, structures of the scala vestibuli, scala tympani, and SG are manually segmented.

In one embodiment, prior to constructing the SSM, the step of identifying the SG neural region further comprises the steps of identifying points in the manual segmentation that correspond to strong cochlear edges in each CT, and arbitrarily assigning the identified points a weight of 1, and all the other points in the manual segmentation a weight of 0.01.

In one embodiment, the step of constructing the SSM comprises the steps of establishing a point correspondence between surfaces of the structures that are manually segmented in each μCT, registering the surfaces to each other with seven degrees of a freedom similarity transformation by using the points, and computing eigenvectors of the registered points' covariance matrix.

In one embodiment, the step of establishing the point correspondence between the structure surfaces comprises the steps of mapping a set of CT image volumes to one of the CT image volumes chosen as a reference volume by using a non-rigid registration, and registering surface of each CT image volume to the surface of the reference volume, so as to establish the correspondence between each point on the reference surface with the closest point in each of the registered CT image surfaces.

In one embodiment, the step of constructing the SSM further comprises the step of constructing a point distribution model (PDM) on the registered manual segmentation surfaces for weighted active shape model (wASM) segmentation by using the weights, so that the SSM is built as a standard PDM computed on the registered exemplar point sets.

In one embodiment, to segment a new image, the SSM is iteratively fitted in a weighted-least-squares scheme to features in the target image, where the edge points with the weight of 1 are fitted to strong edges in the CT image, and the non-edge points with the weight of 0.01 are fitted to the positions determined by non-rigid registration with an atlas image, such that with the chosen weights, the non-edge points provide enough weak influence on the optimization to ensure that the wASM stays near the atlas-based initialization position, while the edge points strongly influence the whole wASM towards a local image gradient-based optimum for a highly accurate result.

In one embodiment, during the SSM construction, a set of SG points in the SSM that interfaces with intra-cochlear anatomy is identified, where the set of SG points is located in an active region (AR) to be stimulated.

In one embodiment, the step of constructing the tonotopic map of the modiolar interface comprises the step of tonotopic mapping each SG point in the AR to the reference by using equations relating cochlear place frequency and angular depth, and once the segmentation is completed, transferring the tonotopic frequency labels from the SSM to the target image.

In one embodiment, the step of identifying the position for each of the plurality of electrodes comprises the step of identifying a centerline of an image artifact created by the electrode array, and sampling points representing the center of each electrode along the centerline to identify the position for each of the plurality of electrodes.

In one embodiment, the step of identifying the position for each of the plurality of electrodes comprises the step of projecting the position for each of the plurality of electrodes and the SG into the same space by using the transformation that registers the pre-operative and post-operative CTs of the living subject.

In another aspect, the invention relates to a system for determining locations of an electrode array implanted in a cochlea of a living subject and spiral ganglion (SG) nerves that the electrode array stimulates, where the electrode array comprises a plurality of electrodes. The system has a controller configured to perform functions of identifying an SG neural region that is targeted for stimulation and its corresponding modiolar interface, constructing a tonotopic map of the modiolar interface to have a tonotopically mapped modiolar interface, and identifying the position for each of the plurality of electrodes relative to the tonotopically mapped modiolar interface in vivo.

In yet another aspect, the invention relates to a non-transitory tangible computer-readable medium storing instructions which, when executed by one or more processors, cause a system to perform functions for determining locations of an electrode array implanted in a cochlea of a living subject and SG nerves that the electrode array stimulates, where the electrode array comprises a plurality of electrodes. The function includes identifying an SG neural region that is targeted for stimulation and corresponding modiolar interface, constructing a tonotopic map of the modiolar interface to have a tonotopically mapped modiolar interface, and identifying the position for each of the plurality of electrodes relative to the tonotopically mapped modiolar interface in vivo.

In a further aspect, the invention relates to a method for customizing cochlear implant stimulation of a living subject, where the cochlear implant comprises an electrode array having a plurality of electrodes, comprising the steps of obtaining one or more anatomic maps of neural frequency responses within the cochlea, determining a geometric-frequency relationship between the one or more anatomic maps of neural frequency responses within the cochlea and the electrode array implanted therein, and using one or more electrodes of the electrode array to stimulate a group of SG neural pathways of the cochlea based on the location of the one or more electrodes and their geometric relationship with the neural pathways.

In one embodiment, each electrode has a distance relative to a closest stimulation point on the SG pathway, and where the SG has a characteristic frequency corresponding to each closest stimulation point.

In one embodiment, the geometric-frequency relationship is represented by an electrode distance-vs-frequency curve showing the distance for each electrode against said spiral ganglion characteristic frequency for each corresponding closest stimulation point.

In one embodiment, the electrode distance-vs-frequency curve is visualized, such that the label above each of the curve segments, which alternate color between two different colors, indicates which electrode is the closest in the frequency region spanned by that segment.

In one embodiment, the method further includes the step of deactivating at least one electrode of the electrode array if the position of the at least one electrode on the electrode distance-vs-frequency curve shows that it interferes with other electrodes.

In one embodiment, the step of using one or more electrodes of the electrode array to stimulate comprises the step of assigning a frequency band to the one or more electrodes of the electrode array for stimulation.

In one embodiment, the step of using one or more electrodes of the electrode array to stimulate comprises the step of adjusting the strength of the input to the one or more electrodes to produce an electric field that is tailored to stimulate specific areas on a tonotopically mapped modiolar interface using the position of the electrodes on the distance-to-frequency curve.

In one embodiment, the step of using one or more electrodes of the electrode array to stimulate comprises the step of adjusting the strength of the input to one or more electrodes to produce an electric field that is tailored to stimulate specific areas on a tonotopically mapped modiolar interface using the position of the electrodes on the electrode distance-vs-frequency curve and inner ear tissue-specific conductivity values.

In yet a further aspect, the invention relates to a system for customizing cochlear implant stimulation of a living subject, where the cochlear implant comprises an electrode array having a plurality of electrodes implanted in a cochlea of the living subject. In one embodiment, the system has a controller configured to perform functions of obtaining one or more anatomic maps of neural frequency responses within the cochlea, determining a geometric-frequency relationship between the one or more anatomic maps of neural frequency responses within the cochlea and the electrode array implanted therein, and using one or more electrodes of the electrode array to stimulate a group of SG neural pathways of the cochlea based on the location of the one or more electrodes and their geometric relationship with the neural pathways.

In one aspect, the invention relates to a non-transitory tangible computer-readable medium storing instructions which, when executed by one or more processors, cause a system to perform functions for customizing cochlear implant stimulation of a living subject, where the cochlear implant comprises an electrode array having a plurality of electrodes implanted in a cochlea of the living subject. In one embodiment, the functions includes obtaining one or more anatomic maps of neural frequency responses within the cochlea, determining a geometric-frequency relationship between the one or more anatomic maps of neural frequency responses within the cochlea and the electrode array implanted therein, and using one or more electrodes of the electrode array to stimulate a group of SG neural pathways of the cochlea based on the location of the one or more electrodes and their geometric relationship with the neural pathways.

In another aspect, the invention relates to a method for customizing cochlear implant stimulation of a living subject, where the cochlear implant comprises an electrode array having a plurality of electrodes implanted in a cochlea of the living subject. In one embodiment, the method includes the steps of determining a position for each of the plurality of electrodes and SG nerves that the electrode array stimulates, determining a geometric relationship between neural pathways within the cochlea and the electrode array implanted therein, and using one or more electrodes of the electrode array to stimulate a spiral ganglion neural region and corresponding modiolar interface of the cochlea according to the location of the one or more electrodes corresponding to the geometric-frequency relationship.

In one embodiment, the step of determining the locations of the electrode array and SG nerves comprises the steps of identifying an SG neural region that is targeted for stimulation and its corresponding modiolar interface, constructing a tonotopic map of the modiolar interface to have a tonotopically mapped modiolar interface, and identifying the position for each of the plurality of electrodes relative to the tonotopically mapped modiolar interface in vivo.

In one embodiment, the step of identifying the SG neural region comprises the steps of constructing an SSM of cochlear anatomy that includes the SG from a set of CT image volumes of cochlea pre-operatively acquired from a number of living subjects.

In one embodiment, the set of CT images of cochlea comprises μCT image volumes of cochlea, where in each μCT image volume, structures of the scala vestibuli, scala tympani, and SG are manually segmented.

In one embodiment, prior to constructing the SSM, the step of identifying the SG neural region further comprises the steps of identifying points in the manual segmentation that correspond to strong cochlear edges in each CT, and arbitrarily assigning the identified points a weight of 1, and all the other points in the manual segmentation a weight of 0.01.

In one embodiment, the step of constructing the SSM comprises the steps of establishing a point correspondence between surfaces of the structures that are manually segmented in each μCT, registering the surfaces to each other with seven degrees of a freedom similarity transformation by using the points, and computing eigenvectors of the registered points' covariance matrix.

In one embodiment, the step of establishing the point correspondence between the structure surfaces comprises the steps of mapping a set of CT image volumes to one of the CT image volumes chosen as a reference volume by using a non-rigid registration, and registering surface of each CT image volume to the surface of the reference volume, so as to establish the correspondence between each point on the reference surface with the closest point in each of the registered CT image surfaces.

In one embodiment, the step of constructing the SSM further comprises the step of constructing a PDM on the registered manual segmentation surfaces for wASM segmentation by using the weights, so that the SSM is built as a standard PDM computed on the registered exemplar point sets.

In one embodiment, during the SSM construction, a set of SG points in the SSM that interfaces with intra-cochlear anatomy is identified, where the set of SG points is located in an AR to be stimulated.

In one embodiment, the step of constructing the tonotopic map of the modiolar interface comprises the step of tonotopic mapping each SG point in the AR to the reference by using equations relating cochlear place frequency and angular depth, and once the segmentation is completed, transferring the tonotopic frequency labels from the SSM to the target image.

In one embodiment, the step of identifying the position for each of the plurality of electrodes comprises the step of identifying a centerline of an image artifact created by the electrode array, and sampling points representing the center of each electrode along the centerline to identify the position for each of the plurality of electrodes.

In one embodiment, the step of identifying the position for each of the plurality of electrodes comprises the step of projecting the position for each of the plurality of electrodes and the SG into the same space by using the transformation that registers the pre-operative and post-operative CTs of the living subject.

In one embodiment, each electrode has a distance relative to a closest stimulation point on the SG pathway, and where the SG has a characteristic frequency corresponding to each closest stimulation point.

In one embodiment, the geometric-frequency relationship is represented by an electrode distance-vs-frequency curve showing the distance for each electrode against said spiral ganglion characteristic frequency for each corresponding closest stimulation point.

In one embodiment, the electrode distance-vs-frequency curve is visualized, such that the label above each of the curve segments, which alternate color between two different colors, indicates which electrode is the closest in the frequency region spanned by that segment.

In one embodiment, the method further includes the step of deactivating at least one electrode of the electrode array if the position of the at least one electrode on the electrode distance-vs-frequency curve shows that it interferes with other electrodes.

In one embodiment, the step of using one or more electrodes of the electrode array to stimulate comprises the step of assigning a frequency band to the one or more electrodes of the electrode array for stimulation.

In one embodiment, the step of using one or more electrodes of the electrode array to stimulate comprises the step of adjusting the strength of the input to the one or more electrodes to produce an electric field that is tailored to stimulate specific areas on a tonotopically mapped modiolar interface using the position of the electrodes on the distance-to-frequency curve.

In one embodiment, the step of using one or more electrodes of the electrode array to stimulate comprises the step of adjusting the strength of the input to one or more electrodes to produce an electric field that is tailored to stimulate specific areas on a tonotopically mapped modiolar interface using the position of the electrodes on the electrode distance-vs-frequency curve and inner ear tissue-specific conductivity values.

In another aspect, the invention relates to a system for customizing cochlear implant stimulation of a living subject, where the cochlear implant comprises an electrode array having a plurality of electrodes implanted in a cochlea of the living subject. In one embodiment, the system has a controller configured to perform functions of determining a position for each of the plurality of electrodes and spiral ganglion (SG) nerves that the electrode array stimulates, determining a geometric relationship between neural pathways within the cochlea and the electrode array implanted therein, and using one or more electrodes of the electrode array to stimulate a group of SG neural pathways of the cochlea based on the location of the one or more electrodes and their geometric relationship with the neural pathways.

In yet another aspect, the invention relates to a non-transitory tangible computer-readable medium storing instructions which, when executed by one or more processors, cause a system to perform functions for customizing cochlear implant stimulation of a living subject, where the cochlear implant comprises an electrode array having a plurality of electrodes implanted in a cochlea of the living subject. In one embodiment, the functions include determining a position for each of the plurality of electrodes and spiral ganglion (SG) nerves that the electrode array stimulates, determining a geometric relationship between neural pathways within the cochlea and the electrode array implanted therein, and using one or more electrodes of the electrode array to stimulate a group of SG neural pathways of the cochlea based on the location of the one or more electrodes and their geometric relationship with the neural pathways.

These and other aspects of the invention will become apparent from the following description of the preferred embodiment taken in conjunction with the following drawings and their captions, although variations and modifications therein may be affected without departing from the spirit and scope of the novel concepts of the disclosure.

BRIEF DESCRIPTION OF THE DRAWINGS

The following figures form part of the present specification and are included to further demonstrate certain aspects of the invention. The invention may be better understood by reference to one or more of these figures in combination with the detailed description of specific embodiments presented herein. The drawings described below are for illustration purposes only. The drawings are not intended to limit the scope of the present teachings in any way.

FIG. 1 illustrates a synthetic example of electrode position analysis. Shown in (a) are a patient's scala tympani (red), scala vestibuli (blue), and modiolar wall (green). In (b), the modiolus surface is color-encoded with its tonotopic mapping (Hz). Also shown are implanted electrodes (gray spheres) and their closest points on the modiolus (indicated by purple lines). The plot in (c) shows the distance of each electrode to the modiolus vs. the SG's characteristic frequency at those closest points. Color indicates whether the electrode is positioned in scala vestibuli (blue), scala tympani (red), or outside the cochlea (black).

FIG. 2 illustrates the contours of segmentation results (red and blue) of the scalae CT (left) and µCT (right). Also shown are manually delineated contours (green and blue-green).

FIG. 18 shows constructing a point distribution model from a set of surfaces.

FIG. 19 shows performing segmentation with the active shape model.

FIG. 31 shows renderings of array reconstruction results. Shown are the histological image (left), automatic reconstruction (middle) and graphs of the electrode position assessment based on histology (black lines) and automatic reconstruction (red dashed lines) for experiments 1-7 (top-to-bottom).

DETAILED DESCRIPTION OF THE INVENTION

Figure 3:
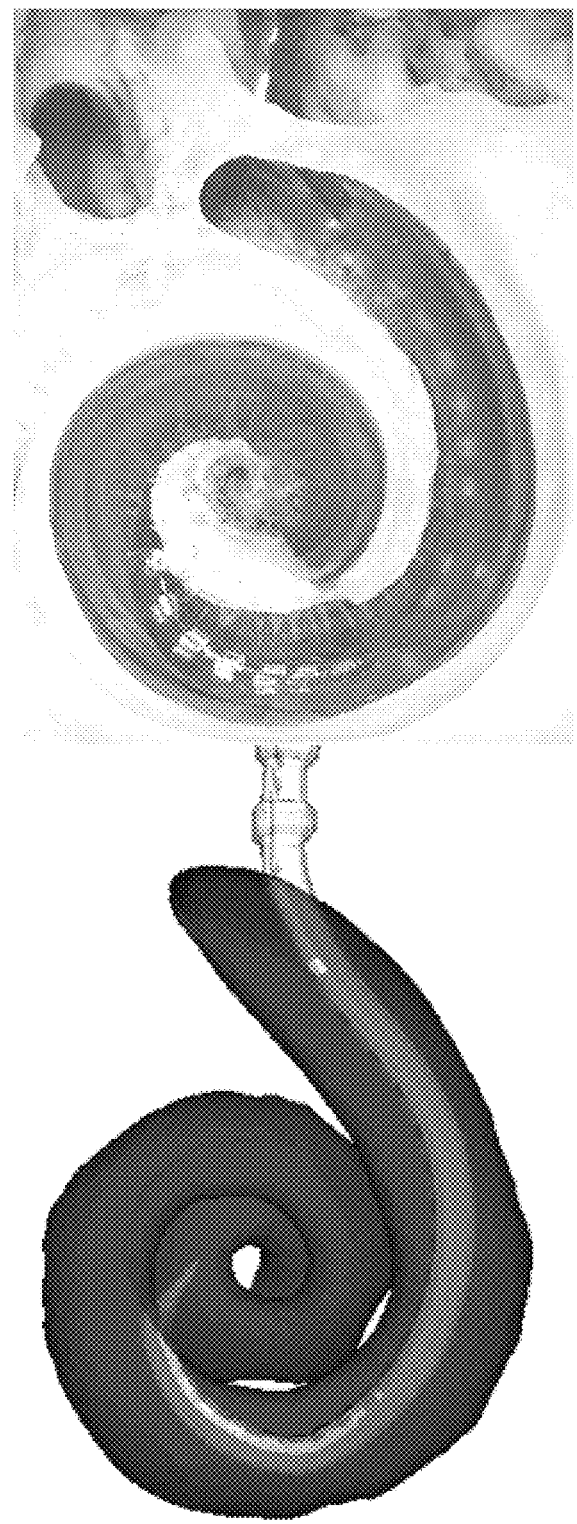
FIG. 3 illustrates the Histology (right) and 3D reconstruction (left) of the electrode array and scala tympani of an implanted specimen.

The invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term are the same, in the same context, whether or not it is highlighted. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", or "includes" and/or "including" or "has" and/or "having" when used in this specification specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top", may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower" can, therefore, encompass both an orientation of "lower" and "upper", depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "around", "about", "substantially" or "approximately" shall generally mean within 20 percent, preferably within 10 percent, and more preferably within 5 percent of a given value or range. Numerical quantities given herein are approximate, meaning that the term "around", "about", "substantially" or "approximately" can be inferred if not expressly stated.

As used herein, the terms "comprise" or "comprising", "include" or "including", "carry" or "carrying", "has/have" or "having", "contain" or "containing", "involve" or "involving" and the like are to be understood to be open-ended, i.e., to mean including but not limited to.

As used herein, the phrase "at least one of A, B, and C" should be construed to mean a logical (A or B or C), using a non-exclusive logical OR. It should be understood that one or more steps within a method may be executed in different order (or concurrently) without altering the principles of the invention.

The description is now made as to the embodiments of the invention in conjunction with the accompanying drawings. In accordance with the purposes of this invention, as embodied and broadly described herein, this invention relates to methods and systems for customizing cochlear implant (CI) stimulations by identifying the positions of implanted CI electrodes and the spiral ganglion (SG) nerves they stimulate for individual CI recipients, so as to improve their hearing outcomes without requiring additional surgical procedures.

As discussed in the background section, there exists no technology to accurately assess the positions of CI electrodes relative to the region targeted for stimulation. It is widely believed in the audiologic research community that individualized tuning schemes based on electrode position have the potential to increase outcomes and subjective sound quality (e.g., [33]). However, it has not until this invention been possible to test this hypothesis. The first image-based approach for identifying electrode position relative to intra-cochlear anatomy was to use rotational tomography to qualitatively analyze electrode position [32]. Their imaging approach produces very high quality in vivo images of the implanted electrode array. However, distinct intra-cochlear anatomy features such as the modiolus and the Basilar Membrane (BM) are still not visible in these images, thus small scale quantitative analysis is not possible using this imaging technique alone. At the same time, other researchers developed a model-based approach for electrode position analysis where the patient's pre- and post-operative CTs are manually aligned with a rigid model of the cochlea created from a single specimen [34]. While this approach was a groundbreaking step towards electrode position analysis, it is limited in that it does not account for non-rigid variations in cochlear anatomy, which have been shown to be substantial [35]. Also, the amount of required expert time per case may be prohibitive for any large scale clinical use. The method the inventors proposed is fully automatic and capable of explicitly and quantitatively identifying both the position of the electrode array and small scale features of intra-cochlear anatomy in vivo [6,8]. The software requires only a pre-operative CT, such as one usually acquired prior to implantation, and a post-operative CT that can be low radiation dose. In one embodiment, this technology is expanded to identify CI electrode positions relative to the region targeted for stimulation in vivo. Such a system could be used in the future to test a wide range of position-dependent CI tuning techniques. However, to show the utility and as an example of the invention, in one embodiment, simple yet novel tuning techniques are tested. While the techniques are highly simplified, they result in measurable improvements in audiological performance by practicing the invention. Specifically, improvements in spatial selectivity and hence, spectral resolution, from individualized tuning parameters have the potential to increase speech recognition performance. Moreover, the analysis of these experiments gives one clear direction for future research testing more comprehensive position-based tuning techniques. In one embodiment, the invention relates to software that can boost the performance of existing CI technology and improve the quality of hearing for implantees.

An example for electrode position analysis, according to one embodiment of the invention, is shown in FIG. 1. FIG. 1a displays a 3D rendering of the patient's intra-cochlear anatomy including the modiolar interface between intra-cochlear cavities and the nerves of the Spiral Ganglion (SG). In FIG. 1b, the modiolar surface is color-encoded with its natural tonotopy, which was extracted using known heuristic data [10]. Also shown in panel b is one possible implanted electrode configuration (electrodes rendered as gray spheres) and purple lines that indicate the closest points on the modiolar surface to each electrode. FIG. 1c displays a plot of the electrode-to-modiolus distance for each electrode as well as the frequency associated with the SG at those closest points. The coloring of each electrode indicates the electrode is positioned in the scala tympani (red), scala vestibuli (blue), or outside the cochlea (black). While typically more apical electrodes are closer to lower frequency portions of the SG, in this example, electrode E4 corresponds to a higher frequency location than E5. This phenomenon can easily occur when electrodes are relatively far from the SG, or in sub-optimal implantation conditions such as a crossing from scala tympani to vestibuli as has occurred in this example. With the traditional approach to cochlear implant mapping, there would be no way to know that this has happened; thus the default frequency allocation map as graded in frequency from apex to base would not faithfully transmit the incoming stimuli to the correct cochlear "place" nor use the correct order of stimulation. However, with the approach according to the invention, it is clear from FIG. 1c that to achieve a monotonic mapping of sound frequency information to the SG, lower frequencies should be allocated to E5 than E4. Finally, the plot also shows which electrodes are not implanted in the cochlea and therefore are ineffective and should be turned off prior to even attempting stimulation. Using the approach according to one embodiment of the invention, this quantitative analysis would be used to determine which electrodes should remain active, the frequencies allocated to each electrode, and the order of stimulation for CIS-based strategies.

The invention, among other things, provides several innovative developments as follows. To the best of the knowledge, this is the first software developed that can (1) identify the SG neural region that is targeted for stimulation and its interface (the modiolus) with intracochlear cavities, (2) compute a tonotopic map of the modiolar interface, and (3) identify the position of individual electrodes in a CI array relative to the modiolus in vivo. Accordingly, a first CI tuning scheme is developed based on the position of electrodes relative to intracochlear stimulation sites. Then, the hypothesis that hearing restoration can be improved by using a position-dependant tuning scheme is tested.

In certain aspects of the invention, a range of advanced tuning techniques that rely on knowing the position of implanted electrodes relative to tonotopically mapped SG nerves is provided. These techniques have the potential to decrease losses caused by these three limitations. However, there has been no technology developed until this invention that allows accurate assessment of electrode position relative to stimulation targets in vivo, which is provided by the certain aspects of the invention and has the potential to increase the effectiveness of existing cochlear implant technology and improve the quality of hearing restoration for implantees.

Another aspect of the invention provides an approach for accurately identifying the SG and predicting its tonotopic mapping, as well as accurately identifying the CI electrode array in post-operative imaging.

In one aspect of the invention, it is discovered that cochlear implant tuning efficacy can be enhanced by knowledge of the position of the implanted electrode array relative to the anatomical structures targeted for stimulation.

In one embodiment, image processing algorithms that are able to accurately determine the location of an implanted electrode array in geometric relationship to the spiral ganglion are developed, which is the structure that is targeted for electrical stimulation, using pre and post-operative CT imaging.

In one embodiment, one is able to accurately locate the position of the electrode array and the spiral ganglion using the patient's CTs by practicing the invention.

In one embodiment, it is developed an algorithmic approach to assist CI tuning.

In one embodiment, using known anatomic maps of neural frequency response within the cochlea and the geometric relationship between the mapped anatomy and the implanted electrode array, one is able to compute electrode tuning parameters by practicing the invention.

In one embodiment, the clinical benefit of the computer-assisted tuning techniques using spectral modulation detection is measured, which has been correlated with audiological outcome.

In one embodiment, it is shown that using the developed software according to the invention will lead to more effective tuning and hearing restoration.

Identification of the Spiral Ganglion:

In the approach, the shape of the SG is predicted based on the external wall of the cochlea, which can be improved by using two algorithmic extensions. The model of intra-cochlear anatomy is constructed is based on a set of cochlea specimens for which both μCT—in which intra-cochlear anatomy is visible—as well as conventional CT, which is the modality targeted for segmentation, are used. Thus, it should be possible to incorporate intensity information from the specimens' CTs into the target CT segmentation process to improve accuracy and robustness. Also, an area of active shape model research that has been little studied is that of weighting differently the reliability of information from different regions of the model [36]. To validate the accuracy of the approach, the set of specimens' CTs is relied using a leave-one-out strategy. The active shape model is constructed, leaving the specimen to be tested out of the model. It is then used to segment the SG in the left-out specimen's CT. Mean and maximum surface distances are computed between the automatic and the manual segmentations of the SG to characterize the error. Subsequently, errors are measured on other specimens using the same process. The data indicate whether the segmentation approach is sufficiently accurate.

It is noted that in certain embodiments, a robust approach for automatically identifying the SG neural region in CT is utilized. In other embodiments, other model-based approaches and robust multi-atlas methods (e.g., [37]) can also be utilized as alternatives.

Tonotopic Mapping of the Spiral Ganglion:

Previous researchers have developed equations that define the tonotopic mapping of the BM based on angular depth [38]. Another group has modified this equation to define the tonotopic mapping of the SG with respect to angular depth [10]. Using these equations, the appropriate frequency is assigned to each point on the scalar-modiolar interface of the SG surface of the active shape model based on angular depth. Thus, when the modiolus is segmented in a target CT, each point on the surface has a corresponding characteristic frequency. The accuracy of this approach will be tested using a leave-one-out strategy, i.e., the tonotopic map predicted by the automated technique will be compared to that computed the known equation [10]. It is expected that the proposed approach will be capable of producing an accurate tonotopy map of the SG in target CTs. If it is found that the predicted maps are inaccurate, maps will be computed for each individual using the known mapping equations.

Identification of the CI Electrode Array:

In this embodiment, the electrode array has 16 independent current sources to which parameter manipulation via their research oriented tuning software can be applied, including order of stimulation, electrode pairing for current focusing, and frequency re-allocation. Thus, as part of this invention, software is presented to accurately locate the CI electrode arrays. Note that the methods to identify the centerline of the electrode artifact also apply here. A model that defines the individual electrode locations with respect to the extracted centerline is constructed. The schematic is used to create a surface model of the array, such as the one seen in FIG. 3, which can be superimposed onto the extracted array centerline in the target image. In one embodiment, the donated arrays are used in a phantom CT experiment, which verifies the precise location in physical space that is implied by the artifact seen in the CT. This is necessary because the distribution of metal in the array is asymmetrical and varies along its length. Thus, it is unlikely that the true centerline of the array overlaps with the centerline of the metallic artifact seen in CT. Once this relationship is extracted from the phantom experiments, any error it may see during algorithmic experimentation is principally due to error in extraction of the artifact centerline. Thus, to validate the approach, error distances between automatically and manually extracted centerlines of the artifact in CTs of the CI implants are measured. It is believed that practicing the invention will lead to the development of a reliable and accurate approach for identifying the CI electrode arrays in post-operative CTs. In one embodiment, a simple automatic rigid image registration can bring the segmentation of the SG in the pre-op CT into alignment with the extracted electrode array in the post-op CTs. Thus, a complete system for determining the position of each electrode with respect to the stimulation region is developed. Alternatively, electrode segmentation include re-tuning algorithm parameters or using other thresholding or model-based techniques, such as tubular active shape models [48], which may be more robust in noisy images, may be utilized to practice the invention.

Figure 4:
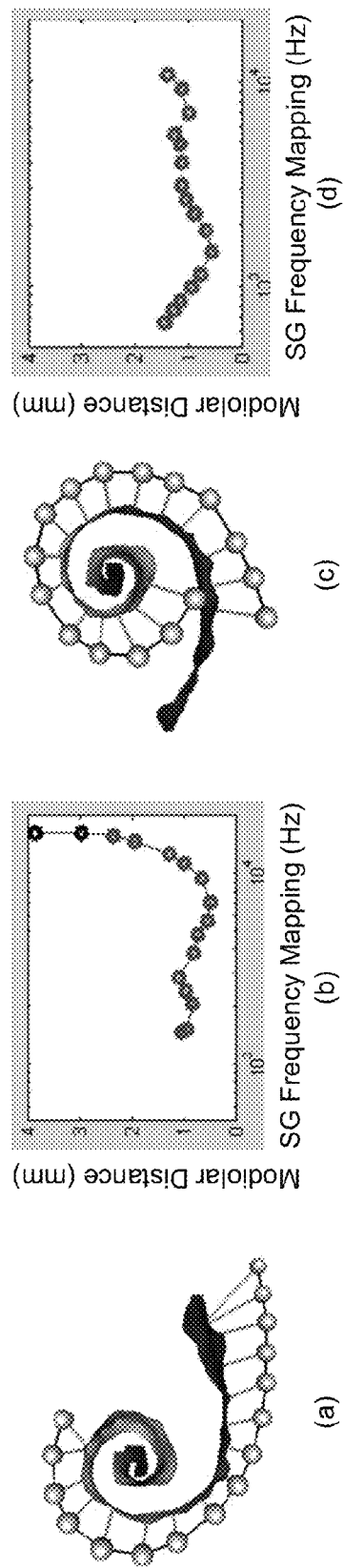
FIG. 4 illustrates the In vivo electrode position analysis. Shown in (a) and (c) are the extracted electrode positions for the patient's right and left implants. (b) and (d) show modiolar distance vs. SG frequency for the left and right implants. Color indicates whether the electrode is positioned in scala tympani (red) or outside the cochlea (black).

Development of a Tuning Approach:

According to certain embodiments of the invention, a simple yet innovative position-based tuning scheme is developed to investigate the advantages of such an individualized approach. In one embodiment, software is developed and used to predict 3 variables. First, it is hypothesized that the distance of an electrode to the modiolus should be proportional to the signal level of that electrode. The predictive software is used to retrospectively analyze implantees that have undergone traditional tuning approaches. Using this data, a heuristic function relating the signal levels applied to electrodes with their modiolar distance is obtained. Once completed, this will be incorporated into the software to predict optimal signal levels. Second, the most basal electrodes used are estimated. For many reasons, the array is often not implanted to an optimal depth, e.g., see FIGS. 4a and 4b. Sometimes these results in electrodes implanted outside of the cochlea, rendering them ineffective. Also, electrodes that are located in the most basal portion of the cochlea and stimulate the SG at >12 kHz frequency regions are generally equally ineffective as the SG cells in this region are significantly less populous and hence less sensitive for those who suffer from longstanding profound sensory hearing loss. With the approach, the potential advantages of deactivating electrodes that correspond to >12 kHz regions of the SG, subject to maintaining a minimum of 10 active internal electrodes when possible are investigated. It is recognized that transmission of speech information ranging from 200 Hz to 12 kHz is necessary in order to achieve high levels of speech recognition and sound quality, thus the full speech spectrum will be mapped to the remaining active electrodes. Finally, stimulation re-ordering of electrodes in the CIS-based strategy employed by the processors is implemented. In a case where a more apical electrode is closer to a higher frequency region of the SG than a more basal electrode (e.g., see FIG. 1), the frequency allocations, electrode pairing for current steering, as well as stimulation order of these electrodes will be manipulated accordingly. Thus, the order of frequencies allocated to the electrodes, paired electrodes for steering of current, as well as the sequential stimulation order will match the order of the SG frequency map of the electrodes. It is believed that this imaging based, individualized simple tuning scheme will yield better audiological outcomes compared to traditional methods. It is possible that this tuning approach may not yield measurably improved results for objective estimates of function, but that this will yield improvement in subjective outcomes.

In another aspects, the developed software according to the invention permits engaging in an extensive amount of clinically translational research for improving audiologic outcomes in CI recipients. While the tuning approach is intuitive, it is not a comprehensive approximation of the behavior of the electric fields induced by the CI in the cochlea. Thus, according to another embodiment of the invention, the electric field properties of the cochlea is studied and utilized. By understanding how current propagates through each tissue class involved in the process (bone, nerves, intra-cochlear fluid), one is able to model how current stimulates the nerves of the SG. Commercially available software is capable of performing this task (e.g. COMSOL Multiphysics®). Since one can accurately model the electric field from the CI array through tissue, one can test a variety of advanced tuning techniques. For instance, position-based tuning algorithms could be designed that result in optimal current focusing in the SG. This would effectively increase the spectral resolution of the CI.

In current clinical practice, the norm is to map the range of frequencies detected by the receiver to the range of active electrodes (those electrodes that a patient can detect when fired). For the vast majority of CI recipients, a default "one-size fits all" frequency allocation table is used. For some individuals it is likely that default tuning provides a reasonable approximation to the individualized anatomy; however, for other patients—particularly those who may exhibit poorer than average performance—"one size fits all" tuning may not afford the restoration of hearing that could be achieved had the recipient's anatomy and intracochlear electrode location been considered. The invention, in one aspect, represents the first step towards challenging this paradigm.

According to other aspects of the invention, certain systems and methods of patient-customized, electrode position-dependant cochlear implant stimulation are provided and further disclosed. Several embodiments utilizing several programming approaches are disclosed.

Figure 5:
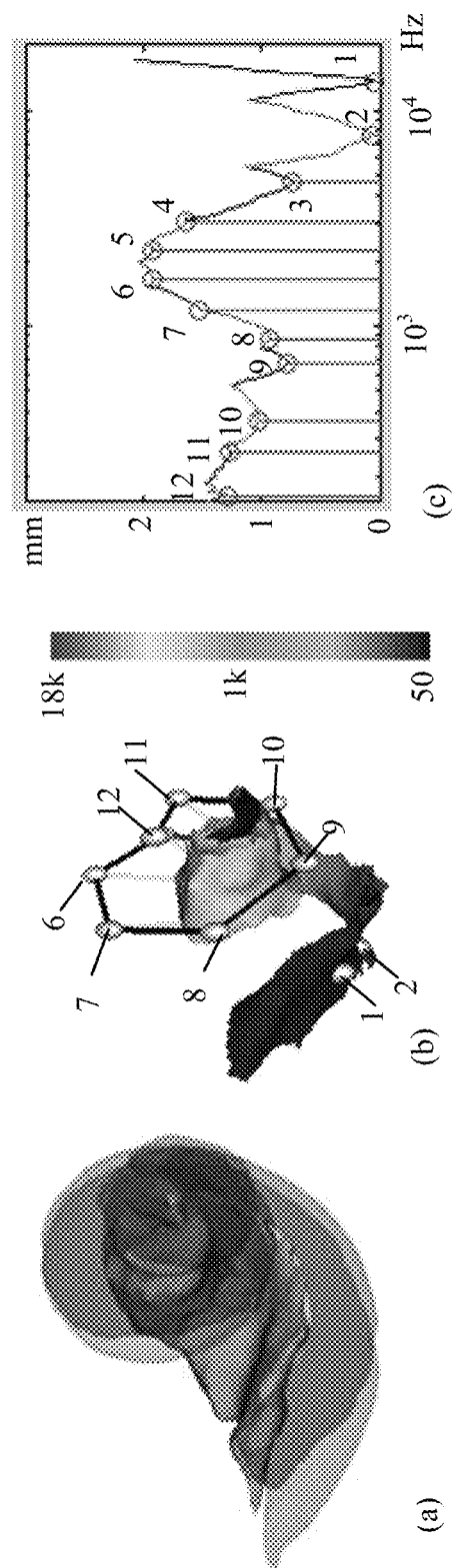
FIG. 5 illustrates in (a), the scala tympani (red), scala vestibuli (blue), and bundle of nerve cells of the SG (green) are shown in 3D. In (b), the active region of the SG is colormapped with its tonotopy (Hz), and the positions of the numbered implanted electrodes are shown (gray spheres). Green lines indicate the closest point on the SG to each electrode. In (c) is a plot of the distance vs frequency information.

Pre-Processing:

Using the above data (position of electrodes and tonotopically mapped stimulation targets), several pieces of information can be established: the distance from each electrode to the closest stimulation point and the characteristic frequency of that point; and the distance to each electrode from each frequency-mapped stimulation position. This information is plotted for a real patient in FIG. 5. In (a), the scala tympani, scala vestibuli, and the bundle of nerve cells of the SG are shown in 3D. In (b), the active region of the SG is colormapped with its tonotopy, and the positions of the implanted electrodes are shown. The green lines indicate the closest point on the SG from each electrode. In (c), red circles indicate the frequency of the closest SG point to each electrode (x-axis) and the distance to that point (y-axis). The curve connecting the points represents the distance from each frequency mapped position on the SG to the closest electrode. The color alternates between purple and black to indicate where the corresponding closest electrode changes. This is called as the electrode distance-to-frequency curve, and as will be discussed below, one inventive aspect of the invention relates to the use of these curves to perform CI programming.

First CI Programming and Stimulation Scheme:

It has not until now been possible to test how electrode position-dependent programming schemes can impact hearing outcomes because the inventors has only recently developed the first approach for detecting the position of implanted electrodes with respect to stimulation targets, as discussed above. The initial experiments test a simple yet creative position-based programming approach, described next, as a baseline for proving that such position-dependent programming schemes positively affect hearing outcomes.

Figure 6:
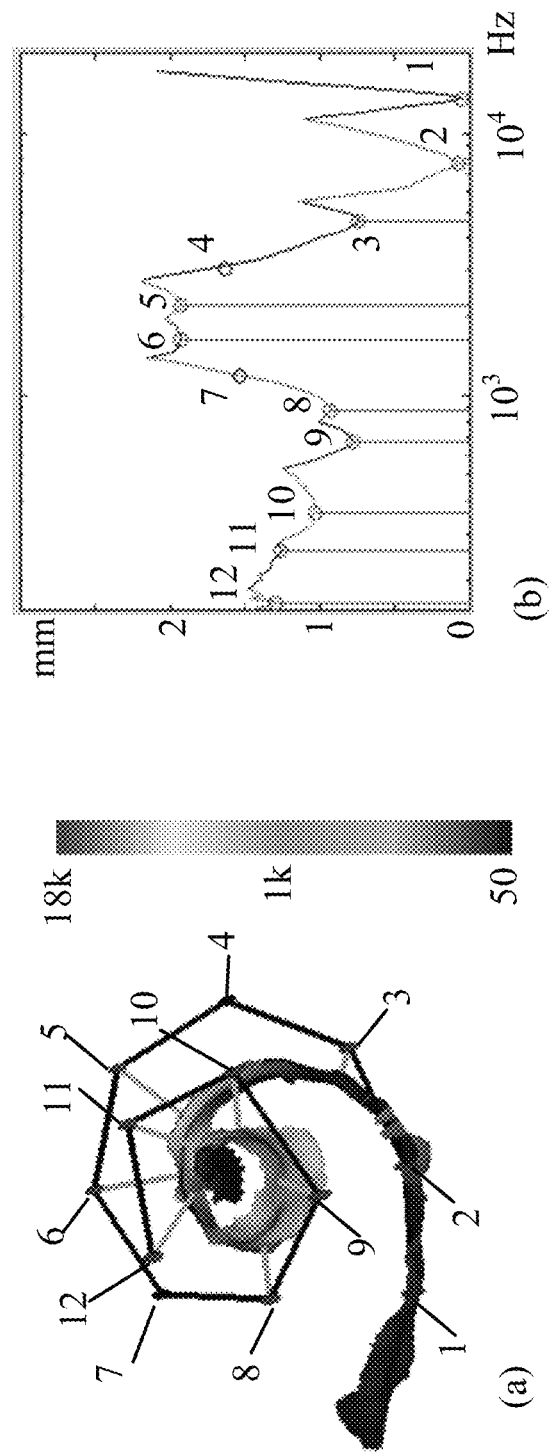
FIG. 6 illustrates in (a), the active region of the SG is colormapped with its tonotopy (Hz), and the positions of the numbered implanted electrodes are shown. In (b) is a plot of the distance vs frequency information after turning off E4 and E7.

One variable that can be modified by the audiologist using the standard software provided by the cochlear implant distributors is which electrodes are turned on and off. Once the set of active electrodes are chosen, the software automatically determines how to distribute the spectrum of frequencies of detected sounds to the set of active electrodes. In the first approach, we are using the image-based information to determine which electrodes should be turned on and off. This is determined using the following constraints: (a) Any electrodes that are unlikely to stimulate active nerve cells are turned off. This happens, for instance, when the electrodes lie outside the cochlea or lie in the most basal region corresponding to >12 kHz where the nerve cells are significantly less populous. (b) Other electrodes are turned off to minimize stimulation of individual nerve cells by multiple electrodes so that frequency information is delivered to better separated distributions of nerve cells. An example of how this is determined is shown in FIG. 6. As can be seen from the curve in FIG. 5c, E4 and E7 at their closest points are essentially equidistant to the SG as E3 and E8. Thus, many nerve cells are being stimulated by multiple electrodes, which transmit information corresponding to a wide band of sound frequencies. For this patient, it is chosen to reprogram this CI by turning off E4 and E7. The resulting electrode distance-to-frequency curve is shown in FIG. 6b. The resulting curve suggests that the new program should result in less smearing of the frequency information in that region of the SG. In general, a good rule of thumb is that an active electrode's red circle in the distance-to-frequency curve plot should be at a local minimum on the curve and the curve should have the same color on both sides of this minimum.

For this patient, improvements in hearing were statistically significant using a binomial distribution statistic for the individual speech perception metrics tested [A1,A2]. The patient's monosyllabic word recognition scores (a quantitative measure of hearing performance) jumped from 33% to 84%, and sentence recognition performance in noise at +10 dB signal-to-noise ratio increased from 46% to 83%. Further, the patient reported significant improvement in hearing and overall sound quality. While very preliminary, these results indicate that image-based programming schemes, even very simple ones, may significantly improve hearing restoration for CI users.

Second CI Programming and Stimulation Scheme:

Once enough data are acquired to prove that electrode position-based programming improves hearing outcome and better learn the mechanisms through which hearing is improved, one can begin testing more advanced approaches. While the programming software from the CI distributer will automatically distribute the spectrum of sound frequencies to the set of active electrodes, as discussed above, it also allows the audiologist to manipulate those frequency bands if desired. Thus, in another embodiment, certain frequency bands are assigned using information from the electrode distance-to-frequency curves. For instance, the group of nerve cells for which E3 is closest, as seen in the distance-to-frequency curve in FIG. 6b, corresponds to a wider frequency band in the logarithmic scale than does E5. Thus, it may be better to map a wider band of detected frequencies to E3 than E5. Extending this innovative approach to the entire array, each electrode could be assigned a frequency band with width proportional to its width in the distance-to-frequency curve. It is possible that such an approach would result in improved hearing outcomes.

Figure 7:
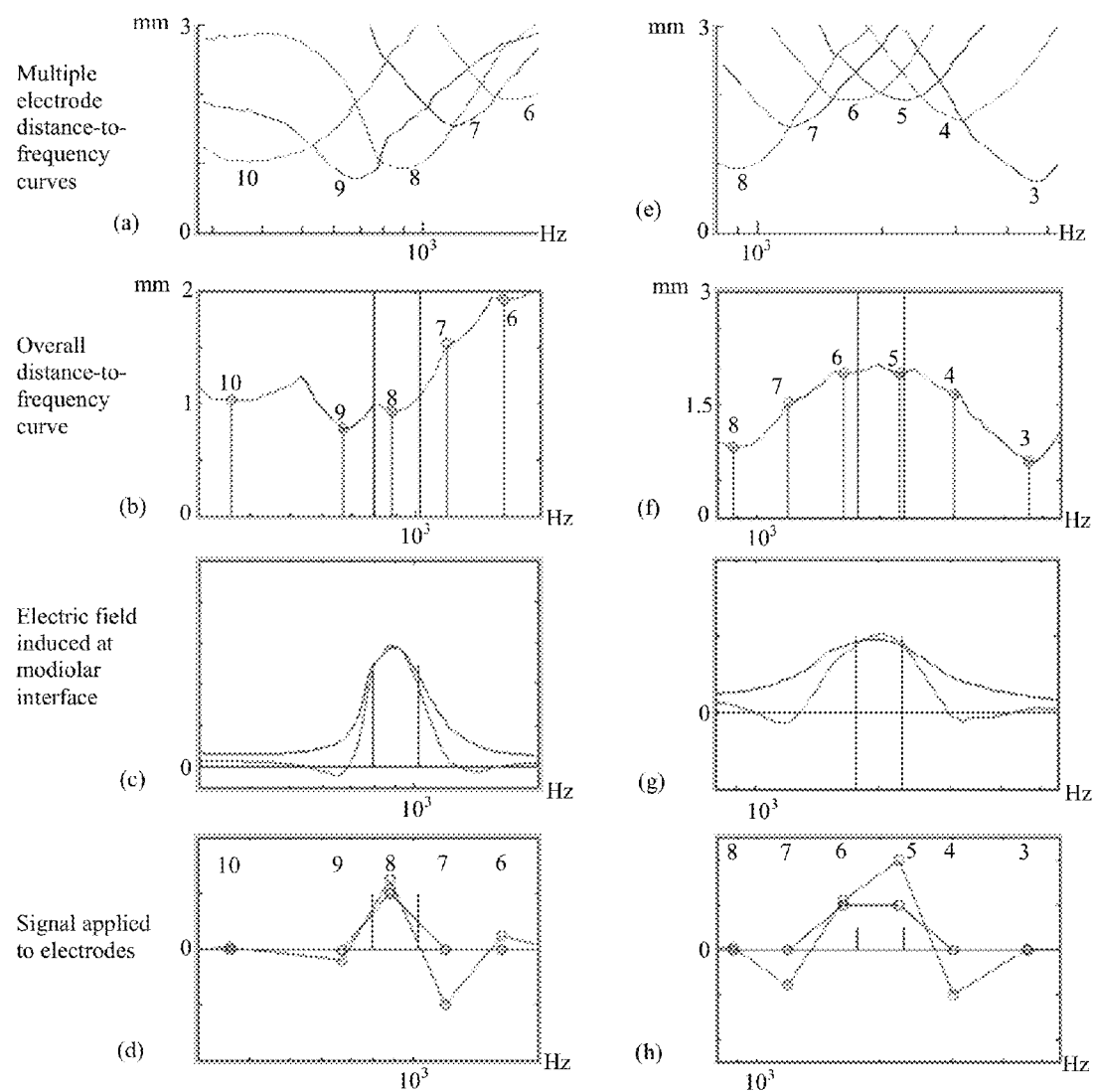
FIG. 7 illustrates two examples of creating sharper electric fields using multiple electrodes.

Third CI Programming and Stimulation Scheme:

It is believed that there is great potential for comprehensive CI programming optimization using electrode position information obtained according to various embodiments of the invention. While the first and second CI programming and stimulation schemes set forth above are creative, they can be further improved by utilizing a more comprehensive approximation of the behavior of the electric fields created by the CI in the cochlea. In yet another aspect of the invention, the electric field properties of the cochlea is studied and taken into the consideration. By understanding how current propagates through each tissue class involved in the process (bone, nerves, intra-cochlear fluid), one is able to model how current stimulates the nerves of the SG. If one can accurately model the electric field from the CI array through tissue in individual patients, one can program the electrode to create specific field patterns. For example, optimization algorithms could be designed to achieve optimal current focusing, i.e., one could create complex electric fields using a combination of electrodes so that electric current is focused at more specific nerve cell regions, effectively creating many more spectral channels by which sound information can be transferred to the spiral ganglion. A simplified example of this is shown in FIG. 7. Consider the problem of stimulating the nerves corresponding to the frequency band between the vertical black lines around E8 (about 800 to 1000 Hz). The strength of an electric field created by an electrode drops proportionally to the squared distance from the electrode in ideal settings. In FIG. 7, this simplified model is used to simulate the use of the electrodes to shape the electric fields in the cochlea. The individual electrode distance-to-frequency curves for E6-E10 are shown in FIG. 7(a) and the overall curve is shown in FIG. 7(b). In blue in FIG. 7(c) is a curve representing the strength of the electric field created across the SG, organized by characteristic frequency, by firing E8. The resulting electric field is strong in the frequency region that are targeting but is not very specific, i.e., it also creates electric potentials in neighboring regions. To sharpen the spectral resolution, one could also fire neighboring electrodes. The red curve represents the strength of the electric field by applying the red signals shown in FIG. 7(d) to electrodes E6-E10. Clearly, this creates a sharper electric field with respect to the SGs natural tonotopic mapping. Choosing the signal levels that best sharpen the electric field is only made possible using the image-based electrode position detection approach. Another example is shown in (FIGS. 7e-7h), in which one would like to stimulate an arbitrary frequency band for which no electrode is in the center (about 1800-2300 Hz). In blue in FIG. 7(g) is the electric field strength at the modiolar interface when E5 and E6 are fired with the signals in blue in FIG. 7(h). Using the signals on E3-E8 shown in red in FIG. 7(h), the electric field can be sharpened as shown in red in FIG. 7(g).

Using this type of analysis, the CI can be programmed to optimize spectral resolution in the cochlea by shaping the electric fields. Many overall programming strategies are possible with the benefits of the invention. One approach is a further extension to current techniques. With traditional programming, the transmission of sound information is broken up into cycles, in each of which, all active electrodes are fired sequentially. Similarly to this, one could divide the stimulation region into a sequence of individual frequency bands, like the ones shown in FIG. 7, and stimulate those bands sequentially for every stimulation cycle using the sets of signals that best sharpen the sequence of electric fields. This type of optimization has the potential to significantly improve hearing quality by increasing the number of information channels the implant can transmit and by minimizing interference between those channels.

Accordingly, in one aspect, the invention relates to a method for determining locations of an electrode array implanted in a cochlea of a living subject and SG nerves that the electrode array stimulates, where the electrode array comprises a plurality of electrodes. In one embodiment, the method includes the steps of identifying an SG neural region that is targeted for stimulation and its corresponding modiolar interface, constructing a tonotopic map of the modiolar interface to have a tonotopically mapped modiolar interface, and identifying the position for each of the plurality of electrodes relative to the tonotopically mapped modiolar interface in vivo.

In one embodiment, the step of identifying the SG neural region comprises the steps of constructing a statistical shape model (SSM) of cochlear anatomy that includes the SG from a set of CT image volumes of cochlea pre-operatively acquired from a number of living subjects.

In one embodiment, the set of CT images of cochlea comprises µCT image volumes of cochlea, where in each µCT image volume, structures of the scala vestibuli, scala tympani, and SG are manually segmented.

In one embodiment, prior to constructing the SSM, the step of identifying the SG neural region further comprises the steps of identifying points in the manual segmentation that correspond to strong cochlear edges in each CT, and arbitrarily assigning the identified points a weight of 1, and all the other points in the manual segmentation a weight of 0.01.

In one embodiment, the step of constructing the SSM comprises the steps of establishing a point correspondence between surfaces of the structures that are manually segmented in each µCT, registering the surfaces to each other with seven degrees of a freedom similarity transformation by using the points, and computing eigenvectors of the registered points' covariance matrix.

In one embodiment, the step of establishing the point correspondence between the structure surfaces comprises the steps of mapping a set of CT image volumes to one of the CT image volumes chosen as a reference volume by using a non-rigid registration, and registering surface of each CT image volume to the surface of the reference volume, so as to establish the correspondence between each point on the reference surface with the closest point in each of the registered CT image surfaces.

In one embodiment, the step of constructing the SSM further comprises the step of constructing a point distribution model (PDM) on the registered manual segmentation surfaces for weighted active shape model (wASM) segmentation by using the weights, so that the SSM is built as a standard PDM computed on the registered exemplar point sets.

In one embodiment, to segment a new image, the SSM is iteratively fitted in a weighted-least-squares scheme to features in the target image, where the edge points with the weight of 1 are fitted to strong edges in the CT image, and the non-edge points with the weight of 0.01 are fitted to the positions determined by non-rigid registration with an atlas image, such that with the chosen weights, the non-edge points provide enough weak influence on the optimization to ensure that the wASM stays near the atlas-based initialization position, while the edge points strongly influence the whole wASM towards a local image gradient-based optimum for a highly accurate result.

In one embodiment, during the SSM construction, a set of SG points in the SSM that interfaces with intra-cochlear anatomy is identified, where the set of SG points is located in an active region (AR) to be stimulated.

In one embodiment, the step of constructing the tonotopic map of the modiolar interface comprises the step of tonotopic mapping each SG point in the AR to the reference by using equations relating cochlear place frequency and angular depth, and once the segmentation is completed, transferring the tonotopic frequency labels from the SSM to the target image.

In one embodiment, the step of identifying the position for each of the plurality of electrodes comprises the step of identifying a centerline of an image artifact created by the electrode array, and sampling points representing the center of each electrode along the centerline to identify the position for each of the plurality of electrodes.

In one embodiment, the step of identifying the position for each of the plurality of electrodes comprises the step of projecting the position for each of the plurality of electrodes and the SG into the same space by using the transformation that registers the pre-operative and post-operative CTs of the living subject.

In another aspect, the invention relates to a system for determining locations of an electrode array implanted in a cochlea of a living subject and spiral ganglion (SG) nerves that the electrode array stimulates, where the electrode array comprises a plurality of electrodes. The system has a controller configured to perform functions of identifying an SG neural region that is targeted for stimulation and its corresponding modiolar interface, constructing a tonotopic map of the modiolar interface to have a tonotopically mapped modiolar interface, and identifying the position for each of the plurality of electrodes relative to the tonotopically mapped modiolar interface in vivo.

In yet another aspect, the invention relates to a non-transitory tangible computer-readable medium storing instructions which, when executed by one or more processors, cause a system to perform functions for determining locations of an electrode array implanted in a cochlea of a living subject and SG nerves that the electrode array stimulates, where the electrode array comprises a plurality of electrodes. The function includes identifying an SG neural region that is targeted for stimulation and corresponding modiolar interface, constructing a tonotopic map of the modiolar interface to have a tonotopically mapped modiolar interface, and identifying the position for each of the plurality of electrodes relative to the tonotopically mapped modiolar interface in vivo.

In a further aspect, the invention relates to a method for customizing cochlear implant stimulation of a living subject, where the cochlear implant comprises an electrode array having a plurality of electrodes, comprising the steps of obtaining one or more anatomic maps of neural frequency responses within the cochlea, determining a geometric-frequency relationship between the one or more anatomic maps of neural frequency responses within the cochlea and the electrode array implanted therein, and using one or more electrodes of the electrode array to stimulate a group of SG neural pathways of the cochlea based on the location of the one or more electrodes and their geometric relationship with the neural pathways.

In one embodiment, each electrode has a distance relative to a closest stimulation point on the SG pathway, and where the SG has a characteristic frequency corresponding to each closest stimulation point.

In one embodiment, the geometric-frequency relationship is represented by an electrode distance-vs-frequency curve showing the distance for each electrode against said spiral ganglion characteristic frequency for each corresponding closest stimulation point.

In one embodiment, the electrode distance-vs-frequency curve is visualized, such that the label above each of the curve segments, which alternate color between two different colors, indicates which electrode is the closest in the frequency region spanned by that segment.

In one embodiment, the method further includes the step of deactivating at least one electrode of the electrode array if the position of the at least one electrode on the electrode distance-vs-frequency curve shows that it interferes with other electrodes.

In one embodiment, the step of using one or more electrodes of the electrode array to stimulate comprises the step of assigning a frequency band to the one or more electrodes of the electrode array for stimulation.

In one embodiment, the step of using one or more electrodes of the electrode array to stimulate comprises the step of adjusting the strength of the input to the one or more electrodes to produce an electric field that is tailored to stimulate specific areas on a tonotopically mapped modiolar interface using the position of the electrodes on the distance-to-frequency curve.

In one embodiment, the step of using one or more electrodes of the electrode array to stimulate comprises the step of adjusting the strength of the input to one or more electrodes to produce an electric field that is tailored to stimulate specific areas on a tonotopically mapped modiolar interface using the position of the electrodes on the electrode distance-vs-frequency curve and inner ear tissue-specific conductivity values.

In yet a further aspect, the invention relates to a system for customizing cochlear implant stimulation of a living subject, where the cochlear implant comprises an electrode array having a plurality of electrodes implanted in a cochlea of the living subject. In one embodiment, the system has a controller configured to perform functions of obtaining one or more anatomic maps of neural frequency responses within the cochlea, determining a geometric-frequency relationship between the one or more anatomic maps of neural frequency responses within the cochlea and the electrode array implanted therein, and using one or more electrodes of the electrode array to stimulate a group of SG neural pathways of the cochlea based on the location of the one or more electrodes and their geometric relationship with the neural pathways.

In one aspect, the invention relates to a non-transitory tangible computer-readable medium storing instructions which, when executed by one or more processors, cause a system to perform functions for customizing cochlear implant stimulation of a living subject, where the cochlear implant comprises an electrode array having a plurality of electrodes implanted in a cochlea of the living subject. In one embodiment, the functions includes obtaining one or more anatomic maps of neural frequency responses within the cochlea, determining a geometric-frequency relationship between the one or more anatomic maps of neural frequency responses within the cochlea and the electrode array implanted therein, and using one or more electrodes of the electrode array to stimulate a group of SG neural pathways of the cochlea based on the location of the one or more electrodes and their geometric relationship with the neural pathways.

In another aspect, the invention relates to a method for customizing cochlear implant stimulation of a living subject, where the cochlear implant comprises an electrode array having a plurality of electrodes implanted in a cochlea of the living subject. In one embodiment, the method includes the steps of determining a position for each of the plurality of electrodes and SG nerves that the electrode array stimulates, determining a geometric relationship between neural pathways within the cochlea and the electrode array implanted therein, and using one or more electrodes of the electrode array to stimulate a spiral ganglion neural region and corresponding modiolar interface of the cochlea according to the location of the one or more electrodes corresponding to the geometric-frequency relationship.

In one embodiment, the step of determining the locations of the electrode array and SG nerves comprises the steps of identifying an SG neural region that is targeted for stimulation and its corresponding modiolar interface, constructing a tonotopic map of the modiolar interface to have a tonotopically mapped modiolar interface, and identifying the position for each of the plurality of electrodes relative to the tonotopically mapped modiolar interface in vivo.

In another aspect, the invention relates to a system for customizing cochlear implant stimulation of a living subject, where the cochlear implant comprises an electrode array having a plurality of electrodes implanted in a cochlea of the living subject. In one embodiment, the system has a controller configured to perform functions of determining a position for each of the plurality of electrodes and SG nerves that the electrode array stimulates, determining a geometric relationship between neural pathways within the cochlea and the electrode array implanted therein, and using one or more electrodes of the electrode array to stimulate a group of SG neural pathways of the cochlea based on the location of the one or more electrodes and their geometric relationship with the neural pathways.

In yet another aspect, the invention relates to a non-transitory tangible computer-readable medium storing instructions which, when executed by one or more processors, cause a system to perform functions for customizing cochlear implant stimulation of a living subject, where the cochlear implant comprises an electrode array having a plurality of electrodes implanted in a cochlea of the living subject. In one embodiment, the functions include determining a position for each of the plurality of electrodes and SG nerves that the electrode array stimulates, determining a geometric relationship between neural pathways within the cochlea and the electrode array implanted therein, and using one or more electrodes of the electrode array to stimulate a group of SG neural pathways of the cochlea based on the location of the one or more electrodes and their geometric relationship with the neural pathways.

Clinical Benefit from the New Innovative Approach:

To measure the clinical benefit of the new innovative approach according to the invention, the performance of the tuning techniques on CI recipients is compared against the default tuning parameters by assessing spectral resolution (SR) with the recipient's original, default parameters as well as with the individually determined parameters. Studies have shown that SR is strongly correlated with speech recognition (e.g., see [47]). Better SR can be achieved by delivering electrical stimulation over a more restricted range of independent neural populations. While CI recipients are known to have poor SR, it is possible that a more individualized approach to CI parameter manipulation based on anatomy, scalar location, and electrode-to-modiolar distance may improve SR and hence speech recognition performance. Spectral modulation detection (SMD) has received increased attention in recent years as it has been shown to provide an efficient and accurate estimate of SR both in acoustic and electric hearing [40, 44, 46]. SMD experiments require the listener to discriminate a spectrally modulated band of noise from one with a flat spectrum. Individuals demonstrating lower SMD thresholds have better SR. Further, [40] demonstrated that psychophysical measures of SR were more sensitive to changes in CI processing strategies than traditional clinical measures of speech recognition. Thus, the inventors propose to obtain SMD thresholds for CI recipients with their default CI parameters as well as with their individualized parameters, which may manipulate i) electrode stimulation order, ii) paired electrodes for current steering iii) number of recommended active electrodes and iv) frequency allocation map.

The SMD task will use a 3-interval, forced-choice procedure to allow discrimination between flat-spectrum and spectrally-modulated noise. The task will be presented with a fixed number of trials for given spectral modulation depths (range of 6 to 25 dB). The test order of modulation depths will be randomized within the procedure. Tests administered will have a bandwidth of 350-5600 Hz and spectral modulation frequencies in the range of 0.25, 0.5 and 1.0 cycles/octave [44, 47]. Each test will consist of 60 trials at a given spectral modulation frequency. Each trial will consist of two intervals with a flat-spectrum noise and one interval containing a spectrally-modulated noise. The modulated noise will be randomly assigned to an interval and listeners are instructed to identify which interval is "different" for each trial. Trials will be scored as correct or incorrect and a percent correct score will be calculated for the test. Trials will be presented in blocks of 10, with 2 repetitions of each modulation depth (20, 17, 14, 11, and 8 dB) in a randomized order. Reliability of results from each listener will be evaluated by comparing the percent correct scores of the first 30 trials with the last 30 trials. In cases where scores vary by more than 10 percentage points (>3 errors), the test will be repeated and an average of the two tests will be used as the estimate of spectral resolution.

In addition to SMD thresholds, traditional measures of speech recognition including monosyllabic word recognition as well as sentence recognition in quiet and noise (+10 and +5 dB signal-to-noise ratio) with speech presented at 60 dB SPL. CNC words [43] and AzBio sentences [45] are the metrics used for gauging performance as these metrics are included in the minimal speech test battery for evaluating performance of adult cochlear implant recipients. In addition to obtaining estimates of speech recognition, the inventors plan to administer questionnaires to measure subjective evaluation of the different tuning schemes including sound quality (Judgement of Sound Quality (JOSQ) [41]), listening benefit (Abbreviated Profile of Hearing Aid Benefit (APHAB) [39]), and implant-related quality of life (Nijmegen Cochlear Implant Questionnaire [42]). All questionnaires have been included here as appendices.

For clinical testing, a number of new and existing CI users will be enrolled. Each participant will be tuned with the technique according to the invention, as well as using the traditional approach. All testing—psychoacoustic, speech and subjective assessment—will be completed after the individual has had at least 4 weeks experience with any given program. To avoid bias that may be introduced by the sequence of the programs, every effort will be made to maintain an even distribution of the order of programs. However, existing CI users will have already been programmed using traditional methods. If, as the research progresses, it appears that more existing than newly implanted CI users are recruited, then all subsequent newly implanted subjects will start with the automated tuning scheme. Differences in outcome between programming approaches will be identified by comparing the resulting values of each performance measure.

It is noted that SMD has been shown to be significantly correlated with speech perception performance and a more sensitive index of programming parameter manipulation than traditional measures of speech perception [40]. Clinical estimates of speech recognition using materials in the minimal speech test battery will enable comparison of performance to those reported in the literature as well as those from the own clinic. Including subjective measures of sound quality, listening benefit, and implant-related quality of life will provide data to i) supplement the psychoacoustic and speech perception measures and ii) to investigate the impact of individualized tuning schemes that may or may not be observed in the objective estimates of spectral resolution and/or speech recognition. Thus, the inclusion of three elements of performance, psychoacoustic, speech, and subjective builds in a multi-dimensional assessment of performance that may improve the effectiveness of the invention.

These and other aspects of the present invention are more specifically described below.

METHODS, IMPLEMENTATIONS AND EXAMPLES OF THE INVENTION

Without intend to limit the scope of the invention, further exemplary procedures and preliminary experimental results of the same according to the embodiments of the present invention are given below.

Identification of the Positions of Cochlear Implant Electrodes and the Spiral Ganglion In one aspect, the invention provides method and system for determining the positions of implanted cochlear implant (CI) electrodes and the spiral ganglion (SG) nerves that the CI electrodes stimulate for patient-customized CI programming, which has an unexpected impact on clinical outcome. Various embodiments according to the invention are further disclosed below.

A. Overview

CIs are considered standard of care treatment for severe-to-profound sensory-based hearing loss. The CIs restore hearing by applying electric potential to neural stimulation sites in the cochlea with an implanted electrode array. The signal characteristics assigned to each electrode are tuned by an audiologist who adjusts stimulus level parameters based on patient response. The majority of potentially adjustable parameters, however, are left at the default settings determined by the CI manufacturer rather than individually adjusted for each individual recipient. Despite this, the programming process remains time consuming and, because of the one-size-fits-all approach, may not result in optimal hearing restoration for all recipients.

The major obstacle for determining the spatial relationship between the electrodes and the SG lies in identifying the SG nerve cells. Identifying the SG in vivo is difficult because nerve fibers have diameter on the order of microns and are too small to be visible in CT, which is the preferred modality for cochlear imaging due to its otherwise superior resolution. Since the SG lacks any contrast in CT, it cannot be segmented directly. However, the external walls of the cochlea are well contrasted in CT, as shown in [6], external cochlear anatomy can be used to estimate the location of intra-cochlear anatomy using a statistical shape model (SSM). Extending the method, one of the objectives of the invention is to use the location of external cochlear features as landmarks to estimate the position of the SG. To do this, an SSM of cochlear anatomy that includes the SG is constructed in one embodiment of the invention.

Figure 9:
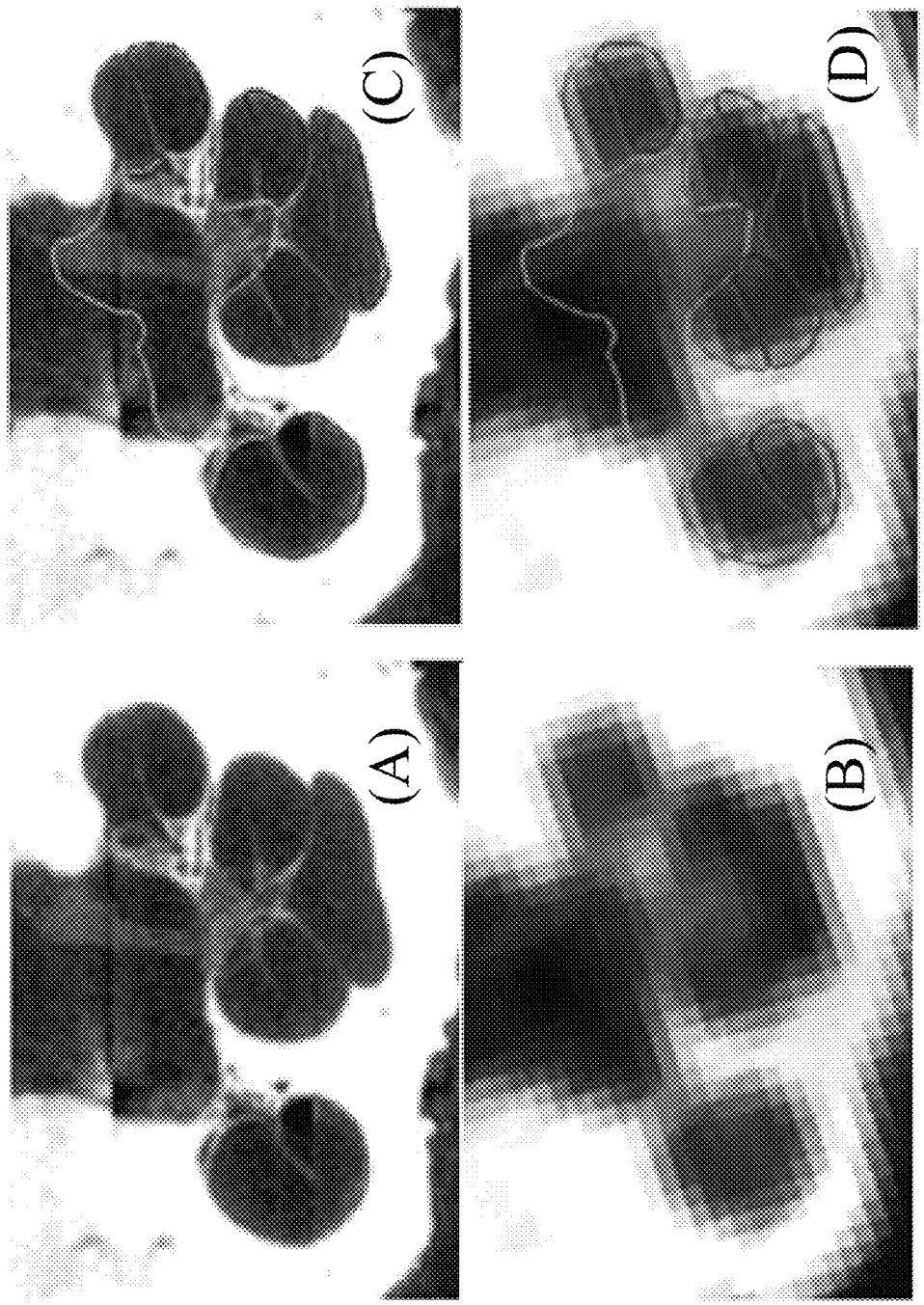
FIG. 9 shows (a) and (b) are a slice of a µCT and a CT of a human cochlea. In (c) and (d), the scala tympani (red), scala vestibuli (blue), and bundle of nerve cells of the SG (green) are delineated in the same slice.

In one embodiment, the data set used to construct the SSM includes images of six cadaveric cochlea specimens. The data set is also referred to a set of training volumes. For each specimen, a μCT image volume is acquired with a SCANCO μCT. The voxel dimensions in these images are about 36 μm isotropic. In addition, conventional CT images of the specimens are also acquired with a Xoran xCAT® fpVCT (flat panel volumetric computed tomography) scanner. In these volumes, voxels are about 0.3 mm isotropic. In each of the μCT volumes, the scala vestibuli, scala tympani, and SG were manually segmented. FIG. 9 shows an example of a conventional fpVCT image and its corresponding μCT image.

Prior to constructing the SSM, points in the manual segmentations that correspond to strong cochlear edges in the CT images are identified. In one embodiment, an importance weight of 1 is arbitrarily assigned to those points, while a lesser weight of 0.01 is assigned to all the other points. These weights are used to construct a point distribution model (PDM) on the registered manual segmentation surfaces for weighted active shape model (wASM) segmentation [24]. The SSM is built as a standard PDM computed on the registered exemplar point sets. To segment a new image, the SSM is iteratively fitted in a weighted-least-squares sense to features in the target image. The edge points with their weight of 1 are fitted to strong edges in the CT. The non-edge points with low weight are fitted to the positions determined by non-rigid registration with an atlas image. With the chosen weights, the non-edge points provide enough weak influence on the optimization to ensure that the wASM stays near the atlas-based initialization position, while the edge points strongly influence the whole wASM towards a local image gradient-based optimum for a highly accurate result.

Figure 8:
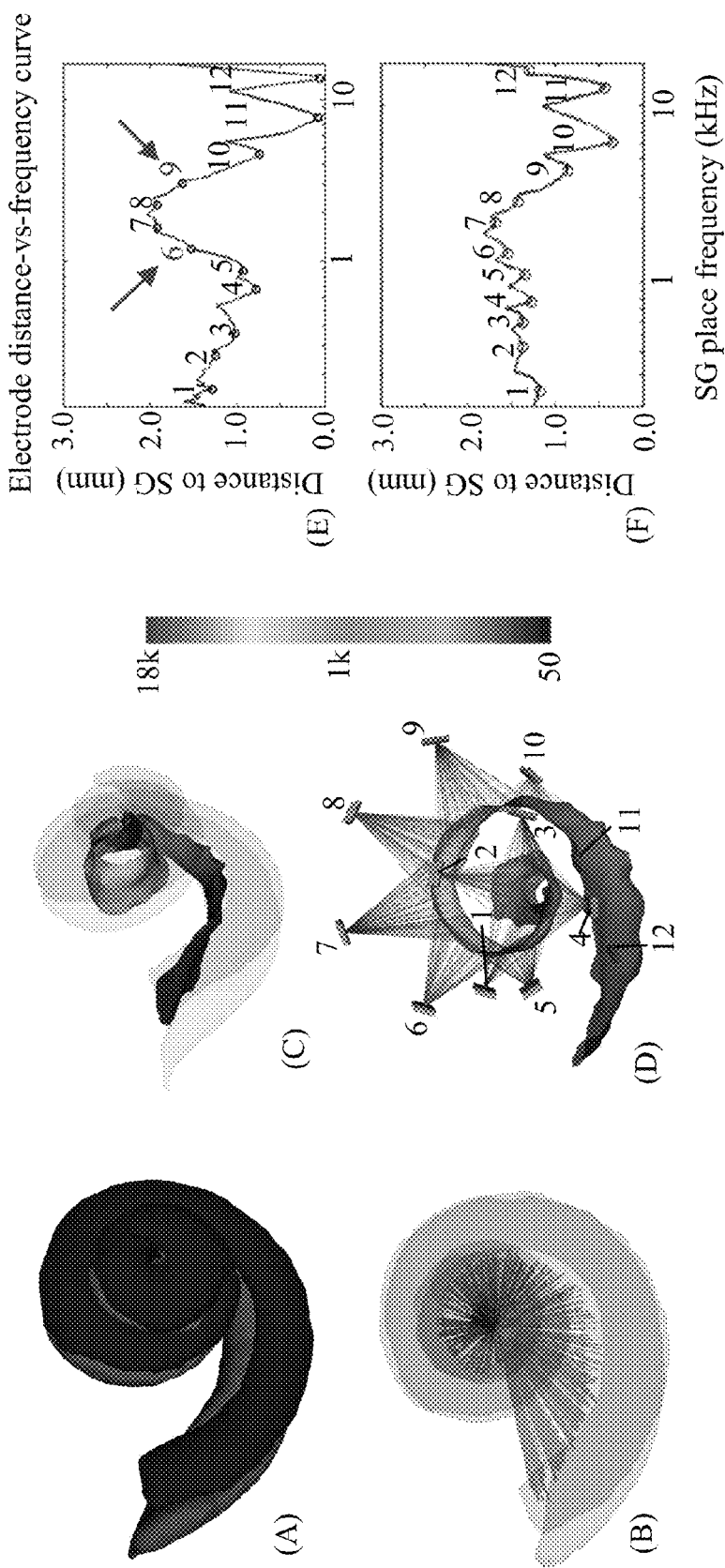
FIG. 8 shows spatial analysis of an implanted subject. The scala tympani (red) and scala vestibuli (blue), the two principal cavities of the cochlea, are shown in (A-C). In (B), also shown is a rendering of the auditory nerve bundles of the SG in green. In (C-D), the AR (the surface representing the interface between the nerves of the SG and the intracochlear cavities) is colorcoded with the tonotopic place frequencies of the SG in Hz. Also shown in (D) are the implanted electrodes of the CI, numbered 1-12. An illustration of current spread from each electrode is rendered transparently in red and blue, with the color alternating between neighboring electrodes. Electrode distance-vs.-frequency curves, shown as a sequence of blue and red segments, are plotted in (E), which corresponds to the ear shown in (D), and (F), which is the curve for the better performing contra-lateral ear of the same subject.

During model construction, the set of SG points in the model that interface with intra-cochlear anatomy are also identified. These points are referred to as the active region (AR) since they correspond to the region most likely to be stimulated by an implanted electrode (see FIG. 8). The tonotopic mapping of each point in the AR in the reference volume is computed using known equations that relate cochlear place frequency and angular depth [10]. Once segmentation is completed, the tonotopic frequency labels from the model are transferred to the target image. While the positions of the electrodes are identified in post-operative CT, the SG is segmented in the pre-operative CT where there are no CI-related metallic artifacts in the image. The transformation that registers the pre-operative and post-operative CTs is used to project the positions of the electrodes and the SG into the same space [8]. These methods are detailed in the following sub-sections.

B. Model Creation

To model cochlear structures, the following steps are performed: (1) establishing a point correspondence between the structure surfaces that are manually segmented in the μCT, (2) using these points to register the surfaces to each other with a 7 degrees of freedom similarity transformation (rigid plus isotropic scaling), and (3) computing the eigenvectors of the registered points' covariance matrix. Point correspondence is determined using the approach described in [6]. Briefly, non-rigid registration is used to map the set of training volumes to one of the training volumes chosen as a reference, and any errors seen in the results are manually corrected. Then, a correspondence is established between each point on the reference surface with the closest point in each of the registered training surfaces. Once correspondence is established, each of the training surfaces is point registered to the reference surface. Since the cochlear edge points will be the highest weighted points for the wASM segmentation, identical weights are used to register the training shapes in a weighted-least-squares sense using standard point registration techniques [26] prior to computation of the eigenspace so that the model will best capture the shape variations at these points.

To build the model, the principal modes of shape variation are extracted from the registered training shapes. This is computed according to the procedure described by Cootes et al. [25]: First, the covariance matrix of the registered training shapes is computed as $$C = \frac{1}{N}\sum_{j=1}^{N}(\vec{v}_j - \bar{v})(\vec{v}_j - \bar{v})^T, \quad (1)$$

where the $\vec{v}_j$'s are the individual shape vectors and $\bar{v}$ is the mean shape. The shape vectors are constructed by stacking the 3D coordinates of all the points composing each structure into a vector. The modes of variation in the training set are then computed as the eigenvectors $\{\vec{u}_i\}$ of the covariance matrix, $$\{\lambda_j, \vec{u}_j\}_{j=1}^{N-1}: \lambda_j \vec{u}_j = C\vec{u}_j. \quad (2)$$

These modes of variation are extracted for the combined shape of the scala tympani, scala vestibuli, and SG for all the samples in the training set.

C. Weighted Active Shape Model Segmentation

In the exemplary embodiment, the procedure for segmentation with a wASM is as follows: (1) the model is placed in the image to initialize the segmentation; (2) better solutions are found while deforming the shape using weighted-least-squares fitting; and (3) eventually, after iterative shape adjustments, the shape converges, and the segmentation is complete. Initialization is performed using the atlas-based methods proposed in [6].

Once initialized, the optimal solution is found using an iterative searching procedure. At each search iteration, an adjustment is found for each model point, and the model is fitted in a weighted-least-squares sense, as described below, to this set of candidate adjustment points. To find the candidate points, two approaches are used. For cochlear edge points, candidates are found using line searches to locate strong edges. At each external point $\vec{y}_i$, a search is performed along the vector normal to the surface at that point. The new candidate point is chosen to be the point with the largest intensity gradient over the range of −1 to 1 mm from $\vec{y}_i$ along this vector. For all other points, it is impossible to determine the best adjustment using local image features alone because there are no contrasting features at these points in CT. Therefore, the original initialization positions for these points, which were provided by atlas-based methods, are used as the candidate positions. With the chosen weights, information from the atlas weakly influences the wASM to stay near the initialization position, while the edge points strongly influence the whole wASM towards a local image gradient-based optimum.

The next step is to fit the shape model to the candidate points. A standard seven (7) degree of freedom weighted point registration is performed, creating similarity transformation T, between the set of candidate points $\{\vec{y}_i'\}$ and the mean shape $\{\bar{v}_i\}$, where $\bar{v}_i$ are the 3D coordinates of the ith point in the mean shape. Then, the residuals $$\vec{d}_i = T(\vec{y}_i') - \bar{v}_i \quad (3)$$

are computed. To obtain the weighted-least-squares fit coordinates in the SSM's eigenspace, the following is computed, $$\vec{b} = (U^T W^T W U)^{-1} U^T W^T W \vec{d} \quad (4)$$

where $\vec{d}$ is composed of $\{\vec{d}_i\}$ stacked into a single vector, $U=[\vec{u}_1\ \vec{u}_2\ \ldots\ \vec{u}_{N-1}]$ is the matrix of eigenvectors that correspond to non-trivial eigenvalues, and W is a diagonal matrix with the importance point weightings in the appropriate entries along the diagonal. This equation results in a vector $\vec{b}$ that represents the coordinates in the SSM space corresponding to a weighted-least-squares fit of the model to the candidate points. The final approximation to the shape is computed by passing the sum of the scaled eigenvectors plus the mean shape through the inverse transformation, equivalently, $$\vec{y}_i = T^{-1}(\bar{v}_i + \Sigma_{j=1}^{N-1} b_j \vec{u}_{j,i}), \quad (5)$$

where $\vec{u}_{j,i}$ is the ith 3D coordinate of the jth eigenvector. As suggested by Cootes, the magnitude of the $b_j$'s are constrained such that $$\sqrt{\sum_{j=1}^{N-1} \frac{b_j^2}{\lambda_j}} \leq 3, \quad (6)$$

which enforces the Mahalanobis distance between the fitted shape and the mean shape to be no greater than 3.

At each iteration, new candidate positions are found and the model is re-fitted to those candidates. The wASM converges when re-fitting the model results in no change to the surface. The tonotopic mapping of the SG points in the model, computed when the model was built, are directly transferred to the target image via the corresponding points in the converged solution. An example result of this mapping process is shown in FIGS. 8C-8D.

D. Electrode Identification

In the exemplary embodiment, these electrodes are identified with the techniques that the inventors have reported [8], which are described in details below. First, the centerline of the image artifact created by the array is identified. This is straightforward since the array is very bright in the image. Then, using a model of the array that describes the spacing between contacts, points representing the centers of each contact are sampled along the extracted centerline.

To permit analysis of the spatial relationship between the electrodes and the SG, the last step of the electrode identification procedure is to use the transformation that registers the subject's pre- and post-operative CTs to bring the extracted electrode positions and the segmented SG surface into the same space.

E. Spiral Ganglion Segmentation Results

The SG segmentation approach was tested on CTs of the set of cochlea specimens. The experiments were conducted using a leave-one-out approach, i.e., the specimen being segmented is left out of the model. A CT was not available for one of the six specimens, and its μCT was used as the model reference volume to simplify the leave-one-out validation study. Thus, in the validation study, segmentation error is measured on the remaining five specimens when using PDMs with four modes of variation. Because these samples were excised specimens, rather than whole heads, the atlas-based initialization process required manual intervention; however, when applied to whole head CTs, the approach is fully automatic.

Figure 10:
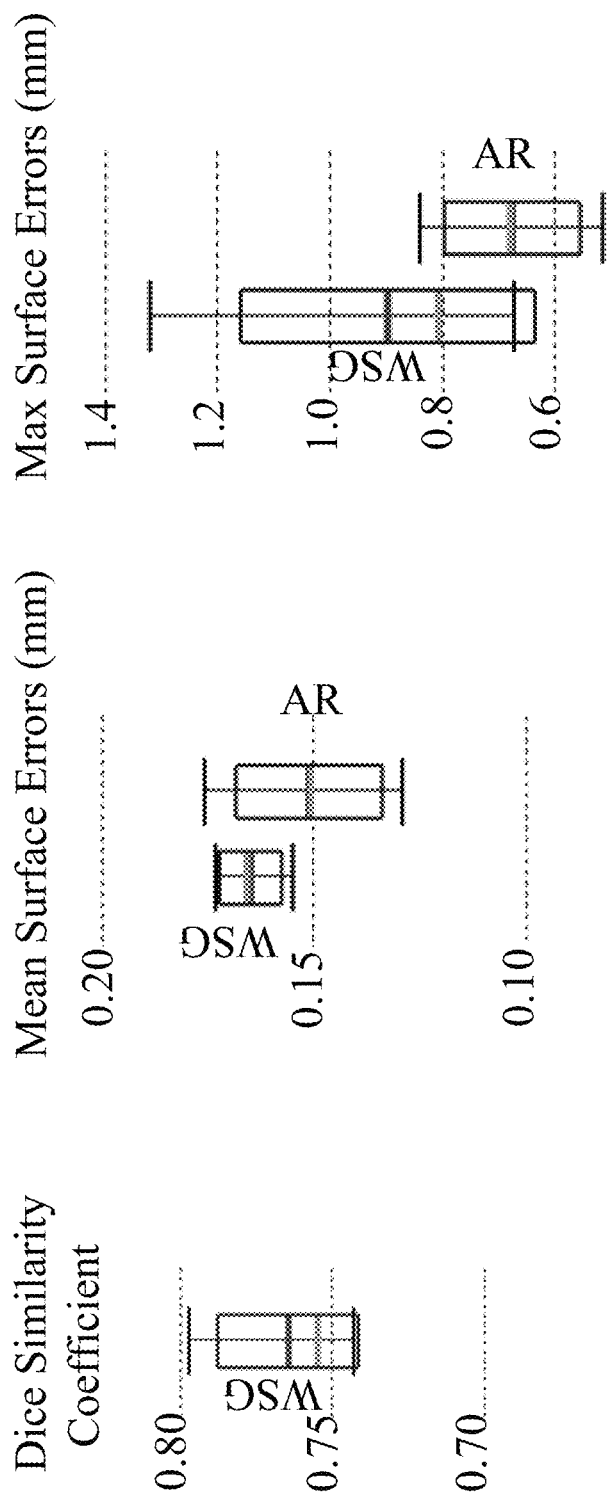
FIG. 10 shows segmentation error distributions of Dice similarity scores for the whole SG (WSG) and mean and max symmetric surface error distributions for the WSG and in the active region (AR).

To validate the results, again, information provided by the set of corresponding μCT volumes is relied. Each CT was rigidly registered to the corresponding μCT of the same specimen. The automatic segmentations were then projected from CT to μCT space. Finally, Dice index of volume overlap [27] and surface errors were computed between the registered automatic segmentations and the manual segmentations to validate the accuracy of the results. FIG. 10 shows the overall distributions of these recorded values. Surface errors were recorded between the whole SGs (WSG) and also between the active regions (AR). Dice indices were not computed for the AR because it is not a closed surface and does not represent a volumetric region. The green bars, red bars, blue rectangles, and black I-bars denote the median, mean, one standard deviation from the mean, and the overall range of the data set, respectively. As can be seen in the figure, the wASM achieves mean dice indices of approximately 0.77. For typical structures, a Dice index of 0.8 or greater is considered good [28]. Here, Dice indices close to 0.8 are consistently achieved for segmentation of a structure that is atypically small and lacks any contrast in the image. Mean surface errors are approximately 0.15 mm for both the WSG and the AR, which is about a half a voxel's distance in the segmented CT. Maximum surface errors are above 1 mm for the WSG but are all sub-millimetric for the AR.

Figure 11:
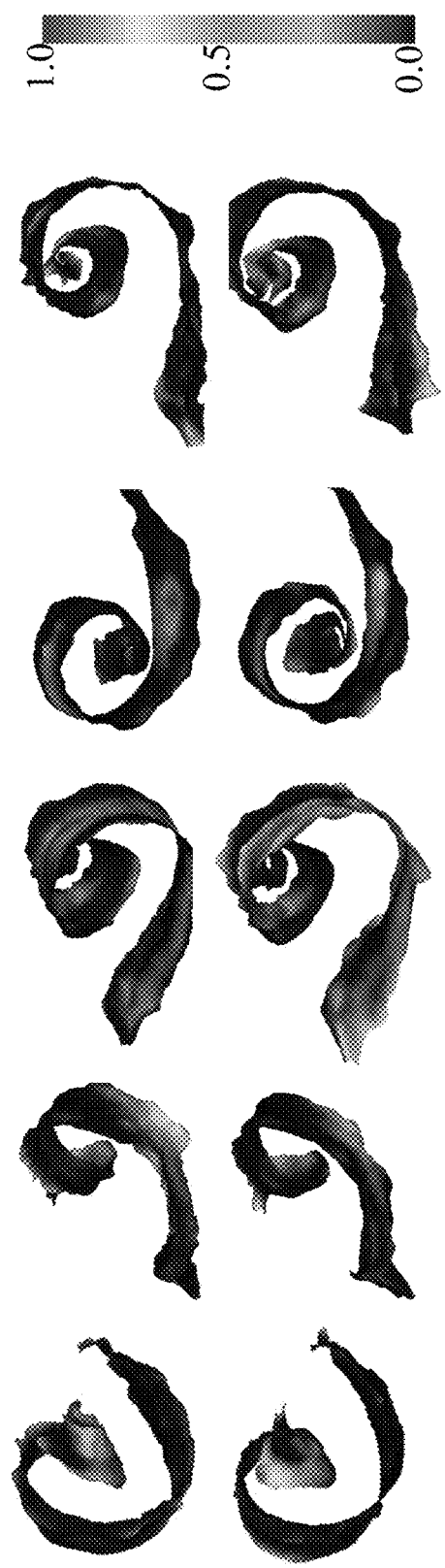
FIG. 11 shows automatic (top row) and manual (bottom row) segmentations of the active region of the SG in the 5 test volumes (left-to-right) color encoded with error distance (mm).
Figure 12:
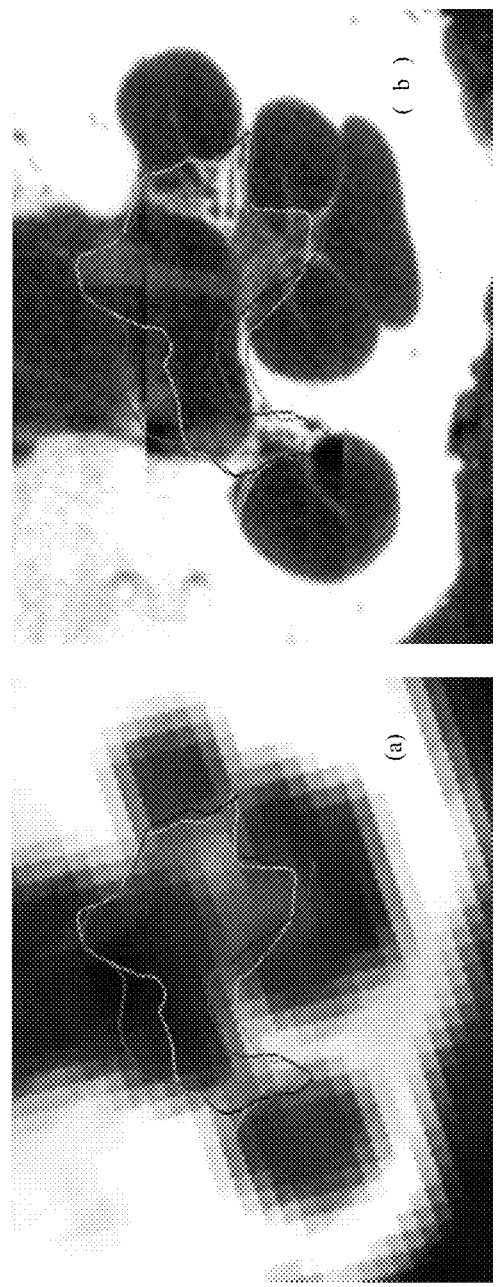
FIG. 12 shows delineations of the automatic (red/blue) and manual (green) segmentation of the SG in the CT (a) and µCT (b) slice from FIG. 9. The active region is shown in blue.

Segmentations for all 5 specimens are shown color encoded with surface error in FIG. 11. It can be seen that the wASM results in mean surface errors under 0.15 mm for the majority of the SG with average maximum errors of about 0.7 mm (<3 voxels). As can be seen in the figure, errors in the AR above 0.5 mm are rare and highly localized. Shown in FIG. 12 are contours of a representative automatic segmentation overlaid with the CT (the volume on which segmentation was performed) and the corresponding registered μCT. It can be seen from the figure that the contours achieved by automatic segmentation of the CT are in excellent agreement with contours manually delineated in the high resolution μCT, especially in the AR. Localization errors that are apparent in the μCT are less than 2 voxels width in the CT.

Image-Guided Cochlear Implant Programming

A. Spatial Visualization and Analysis

Once the positions of the electrodes and the SG are identified, analysis of their spatial relationship is necessary to extract programming-relevant information. Thus, to support the design of new image-guided MAPping methods, a new technique for visualizing programming-relevant spatial information, called as the electrode distance-vs.-frequency curve, is also developed, an example of which is shown in FIG. 8e. This plot summarizes the important information the new image processing techniques provide. The height of the curve on the vertical axis shows the distance from SG nerve pathways, organized by characteristic frequency along the horizontal axis, to the closest electrode. The label above each of the curve segments, which alternate color between red and blue, indicates which electrode is the closest in the frequency region spanned by that segment. Using this new visualization method, not only is it easy to infer the region of the SG that a specific electrode will best stimulate, e.g., the nerve pathways with characteristic frequencies around 1 kHz are closest to electrode 5; but also it is easy to detect when two electrodes stimulate the same region. For instance, the absence of local minima in curve segments associated with electrodes 6 and 9 indicates that the neural pathways stimulated by these two electrodes are receiving overlapping stimulation from neighboring electrodes, and hence are affected by channel interaction. The electrode distance-vs.-frequency curve for this subject's contra-lateral ear is shown in FIG. 8f. While electrode interactions are only one of many factors that could affect CI performance, it is interesting to note that for this particular subject, the curves indicate that channel interactions are less likely to be occurring in the better performing ear in (F) than in the poorer performing ear (E).

B. Image-Guided MAPping Strategy

To demonstrate the utility of the new information, one example image-guided MAPping strategy is tested. The approach incorporates the continuous interleaved sampling (CIS) signal processing strategy introduced by Wilson et al. [9]. Since its introduction, CIS has been widely adopted, and all CI manufacturers today use CIS-based strategies [2]. By using non-simultaneous, interleaved pulses, CIS decreases cross-electrode electric field channel interactions without precise knowledge of the relative location of the neural pathways and the electrodes. But, by integrating spatial information provided by the image-processing techniques, this concept is extended to decrease electrode interactions at the neural level, i.e., reduce the cross-electrode neural stimulation overlap. In the experiments, the MAP adjustment strategy is simple. Electrodes that are likely to cause stimulation overlap are deactivated, which, as discussed above, can be inferred from the distance-vs.-frequency curve. Conveniently, this approach does not conflict with existing signal processing strategies, and thus the MAP adjustments do not require major processing changes. Electrode deactivation schemes are not new, e.g., some groups have experimented with randomly deactivating a number of electrodes and found little effect on speech recognition as long as more than 4-8 electrodes are active [11, 12]. Other groups deactivated electrodes based on psychoacoustics measures, resulting in detectable increases in a sub-set of the measures of speech recognition reported by the authors [13, 14]. However, the deactivation scheme presented herewith is the first that uses image-guidance. In the experiments, after identified electrodes are deactivated, the sound spectrum is simply remapped to the remaining active electrodes using the CI manufacturer's clinical software. No other programming variables are adjusted.

C. Image-Guided Programming Experiments

Figure 13:
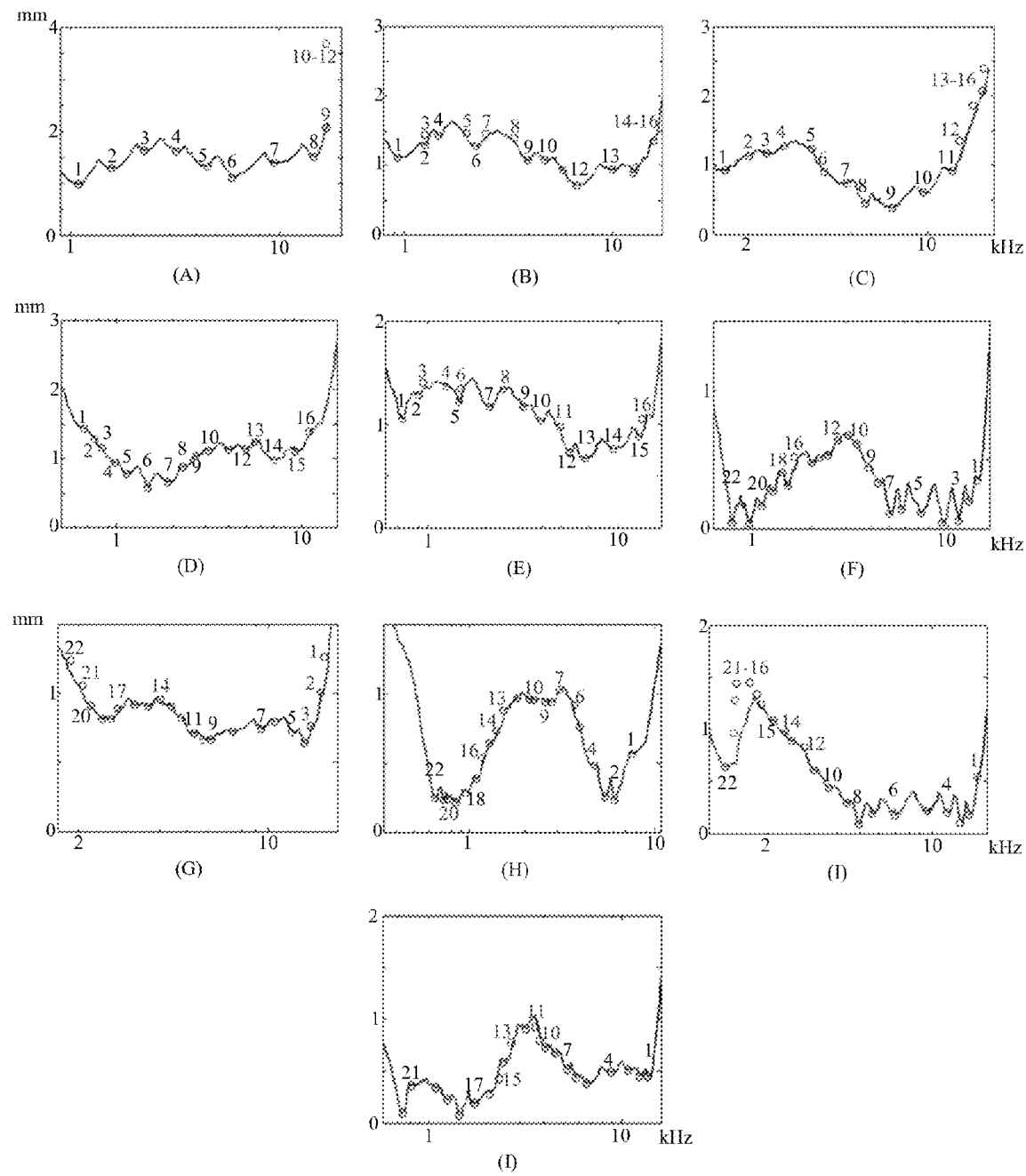
FIG. 13 shows electrode distance-vs.-frequency curves for each test subject. (A)-(I) Show the electrode distance-vs.-frequency curves, similarly to FIG. 8e, for subjects 2-10. Electrodes deactivated in our experiments are shown in red.
Figure 14:
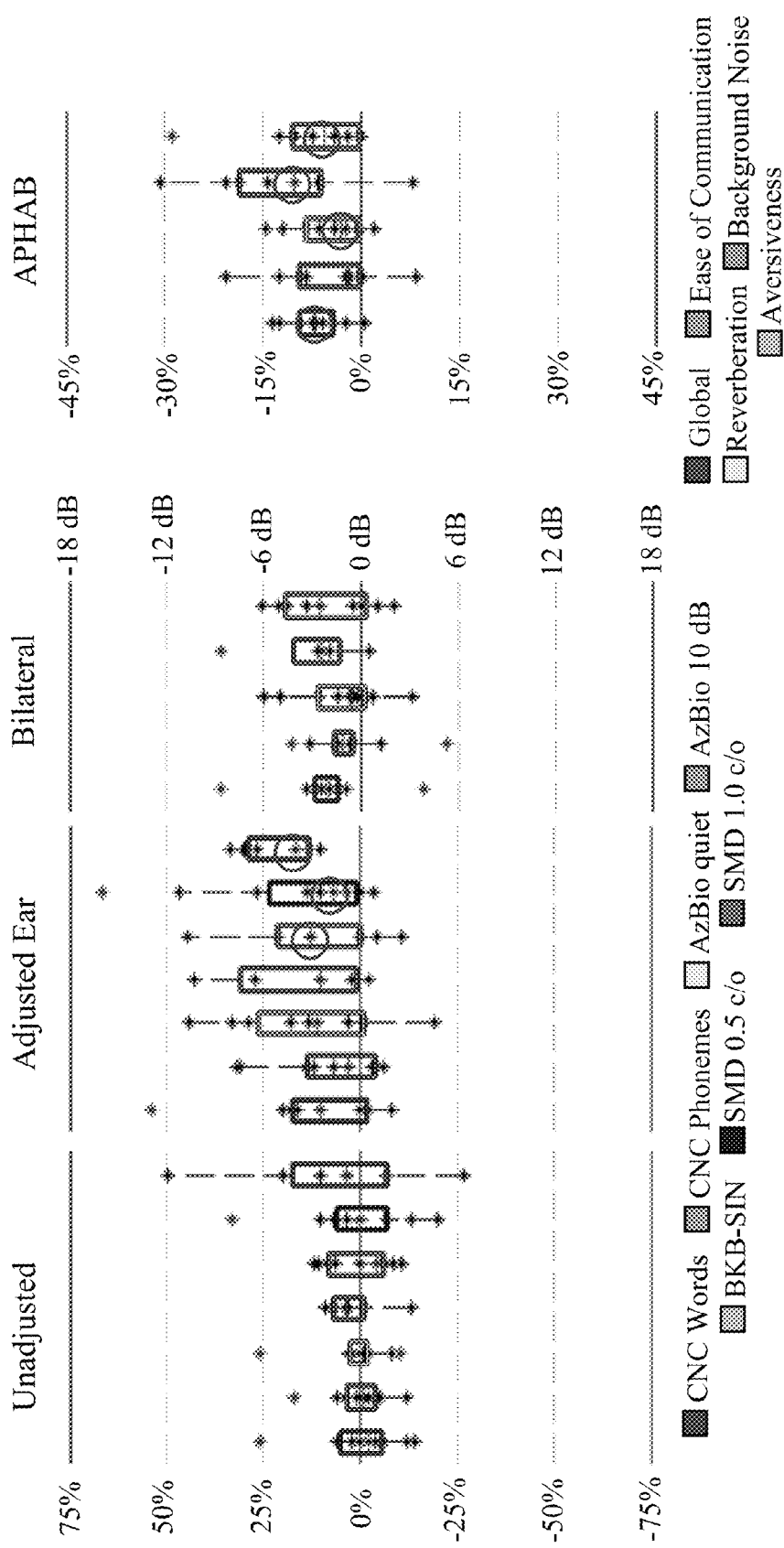
FIG. 14 shows box plots of the difference between post- and pre-adjustment scores of each hearing performance measure. Shown are the interquartile range (box), median (red line), individual data points (black dots). Whiskers extend to data points that lie within 2 times the interquartile range from the mean. Outlier points that lie beyond the whiskers are highlighted in red. Measures that reach statistical significance are indicated by red circles.

Eleven bilaterally implanted, long-term CI users participated in the image-guided programming experiment. Prior to this study, each of these subjects had undergone several iterations of traditional programming adjustments and was considered by an expert audiologist to have achieved the best hearing performance possible using the traditional behavioral programming approach. Length of CI use among subjects ranged from 0.8 to 8.9 years with an average of 3.4 years. For each subject, a battery of hearing and speech recognition tests was performed on both ears individually as well as in the bilateral condition. Then, the MAP for the poorer performing ear was manipulated according to the electrode deactivation scheme described above. The electrode distance-vs-frequency curves and deactivation plans are shown in FIG. 8e for subject 1 and FIG. 13 for the remaining subjects. Each subject returned for post-adjustment re-testing 3-4 weeks following the image-guided MAPping. Several widely used speech recognition metrics were measured including Consonant Nucleus Consonant (CNC) [15] word and phoneme scores (% correct), AzBio sentence recognition [16] in quiet and at a +10 dB signal-to-noise ratio (% correct), and the Bamford-Kowal-Bench Speech-In-Noise (BKB-SIN) test (dB SNR) [17]. Additionally, spectral modulation detection (SMD) was assessed, which is a non-speech based hearing performance metric that provides a psychoacoustic estimate of spectral resolution, i.e., the ability of the auditory system to decompose a complex spectral stimulus into its individual frequency components [18-20]. The spectral modulation detection task used a 3-interval, forced-choice procedure to contrast flat-spectrum noises with spectrally modulated noises. The task included a fixed number of trials at fixed spectral modulation depths ranging from 8 to 16 dB in 2-dB steps and was thus not an adaptive, iterative process but rather incorporated a methodology based upon the method of constant stimuli [29]. Sixty trials were presented at both 0.5 and 1.0 cycle per octave (c/o), and performance was expressed in % correct. All speech and non-speech testing was conducted at a calibrated presentation level of 60 dB SPL using a single loudspeaker presented at 0° azimuth at a distance of 1 meter. In FIG. 14, a box plot for each hearing performance metric shows the distribution across subjects of pre-adjustment scores subtracted from post-adjustment scores. As seen in the figure, results of the pre- and post-adjustment tests performed on the unadjusted ear alone show no detectable change on average. In contrast, the group average test results for the adjusted ear improve dramatically for all measures. While it is difficult to detect significance for measures that are not normally distributed with sample sizes this small (N<=11), it is notable that one was able to detect statistically significant differences for the BKB-SIN and SMD measures using the Wilcoxon signed rank test [21] at p<0.05 (indicated in the plot by red circles). In the bilateral condition, each of the measures also improves on average. In both the pre- and post-adjustment condition, each subject was also asked to complete an Abbreviated Profile of Hearing Aid Benefit (APHAB) [22] questionnaire that measures several aspects of hearing-related communication effectiveness. These results are shown in a similar box plot on the right. The APHAB questionnaire is scored as the percentage of problems with overall ease of communication, reverberation, background noise, aversiveness, and a global score that incorporates all problem types. The plot shows that the group average of each APHAB score decreases for the post-adjustment questionnaires, and the improvements in 4 of 5 of these measures reach statistical significance measured using the Wilcoxon signed rank test at the p<0.05 level. The most significant qualitative improvement may be performance in background noise. This is also reflected in the quantitative results, where in the adjusted ear, measures that include noise, i.e., AzBio+10 dB, BKB-SIN, and SMD at both modulation rates all substantially increase on average from pre- to post-adjustment tests.

Figure 15:
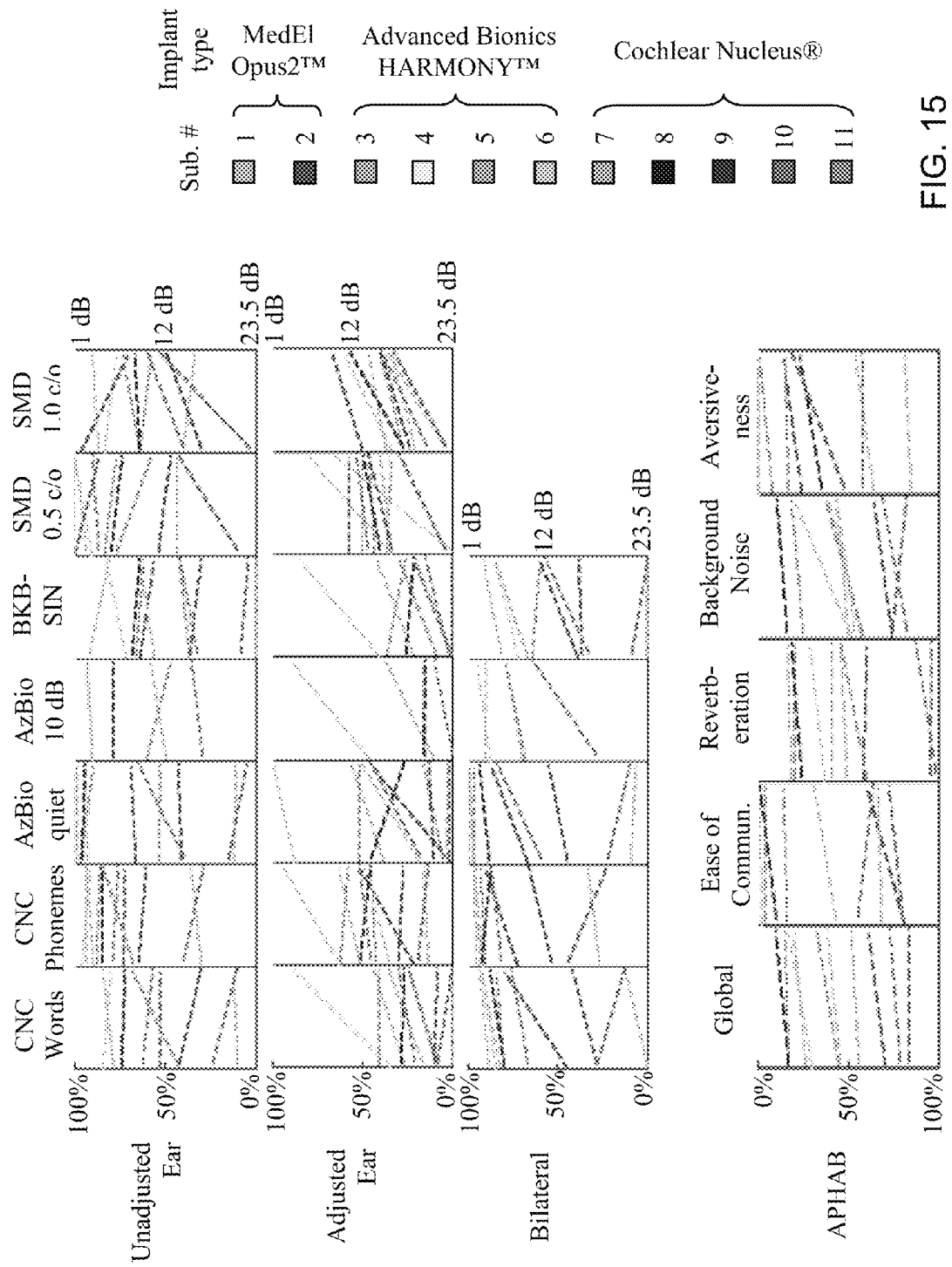
FIG. 15 shows individual hearing performance results for all eleven subjects shown as line plots. The left and right ends of each line plot show pre- and post-adjustment results for the indicated subject and hearing performance measure, respectively.

Results color-coded by individual subject are shown in as line plots in FIG. 15. Lines with positive slope indicate scores that have improved from pre- to post-adjustment. Since for APHAB, the higher the score the poorer the result, to keep a similar visual convention with the other plots, the y-axis for APHAB results on the bottom row is reversed relative to the top rows. Due to some logistical constraints, not all measures were tested for every subject, and lines corresponding to measurements that were not tested are omitted from the plot. Although the results for subject 10 were not excluded in any of the results, it is believed that they are outlier measurements as there are substantial differences in scores for the unadjusted ear, and the adjusted ear appears to follow the same trend. It was noted during testing that this subject exhibited signs of cognitive decline, but in this exemplary embodiment, the inventors did not administer any screening instruments designed to identify those at risk for cognitive impairment. Several subjects experienced remarkable improvement in scores for their adjusted ear, e.g., CNC word scores for subjects 1, 2, 3, 5, and 7 more than or almost doubled. Performance improvement for subjects 1, 2, 3, 5, 7, and 11 reached statistical significance at the individual level measured using a binomial distribution statistic for CNC monosyllables [30] and AzBio sentences [16]. SMD at 1.0 cycle/oct improved for every subject and almost double on average. This finding alone is substantial, as few developments in strategy in the past 20 years have been shown to significantly improve spectral resolution for CI recipients [8].

Improvements in bilateral performance may not seem substantial at first glance. However, with the exception of subjects 2, 9, and 11, all of the subjects already had very high scores due to their better performing ear (1, 3, 4, 7, and 8) or had very low overall scores (6 and 10), and thus the change in performance could be masked in these quantitative scores by effects of range saturation of the measures used. Bilateral scores for subjects 2, 9, and 11 on the other hand improved substantially. The quality of overall changes is best reflected in the APHAB scores. With the exception of subject 10, performance in background noise substantially improves for all subjects. This is especially significant considering that speech recognition in noise is one of the most common problems even among the best performing CI users [4]. All other measures of sound quality either also improve or, at worst, are approximately unchanged post-adjustment. With the exception of subjects 6 and 10, each subject requested no further changes to their adjusted ear and elected to keep their experimental MAPs following these experiments.

According to the embodiments of the invention, a set of novel methods that facilitate image-guided CI programming is presented. The approach is to extract programming-relevant information in the form of electrode distance-vs.-frequency curves by analyzing the spatial relationship between the CI electrodes and the SG nerves they stimulate. Also an example image-guided MAPping strategy is presented, and it is shown that it leads to significant improvement in hearing outcomes.

The biggest obstacle for user-specific CI spatial analysis is to identify the SG, which lacks any contrast in conventional CT. To do this, a weighted active shape model-based approach is used. This approach accurately locates the SG by using the exterior walls of the cochlea as landmarks. Additionally, high resolution images of cadaveric specimens are used to serve two functions. First, they provided information necessary to construct an SSM of the structure, permitting segmentation of the structure in conventional imaging for the first time. Second, the high resolution images were used to validate the results. This was performed by transferring the automatically segmented structures from the conventional images to the corresponding high resolution images and comparing those structures to manual segmentations. The approach achieves dice indices of approximately 0.77 and sub-millimetric maximum error distance in the region of interest for CI stimulation.

The results of the image-guided MAPping tests show that the image-guidance techniques can be used to significantly improve hearing outcomes with CIs. Since the MAP strategy disclosed in the application only requires deactivating electrodes, it is simple to integrate with existing sound processing strategies, such as CIS, using the existing clinical software provided by CI manufacturers. Typically when changes to a MAP are made, quantitative and qualitative hearing scores tend to favor the original MAP [23]. Thus, it is remarkable that the majority of the subjects in the experiments noted substantial improvement in sound quality immediately after re-programming, and these improvements are reflected in the quantitative results. It is likely that long-term experience with the new MAP will result in further improvements in hearing performance. According to the NIDCD, over 200,000 people have received CIs as of 2010 [1]. The electrode deactivation strategy could improve hearing in many of these CI users, thus improving their communication abilities and hearing-related quality of life, without requiring additional surgical procedures. The results show that image-guided, personalized approaches to CI programming can indeed improve spectral resolution and speech recognition in quiet and noise. However, the electrode deactivation strategy disclosed in the application exploits only a small fraction of the programming relevant information captured by the image processing and analysis techniques. Thus, it is believed that this study presents just the first of many new and significant user-customized stimulation strategies that will be developed now that analysis of the spatial relationship between electrodes and stimulation targets is possible.

Automatic Segmentation of Intra-Cochlear Anatomy in Conventional CT

Figure 16:
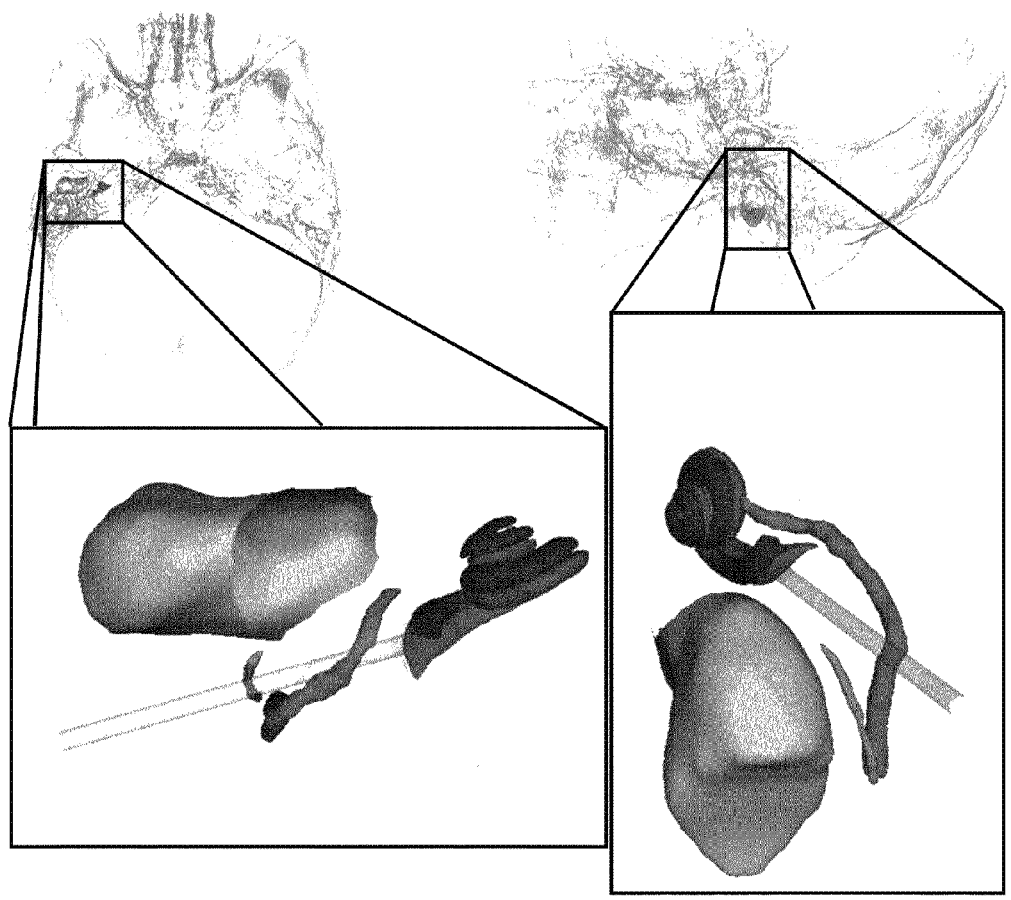
FIG. 16 shows superior-to-inferior view (left) and lateral-to-medial view (right) of ear anatomy. Shown are the cochlear labyrinth (yellow), facial nerve (purple), chorda tympani (green), auditory canal (blue-green), scala tympani (red), scala vestibuli (blue), and the traditional surgical approach (orange tube).

Cochlear implant surgery is a procedure performed to treat profound hearing loss. In a typical surgery, a mastoidectomy is performed, excavating bone posterior to the auditory canal to gain access to the cochlea while avoiding damage to vital structures. The sensitive structures along the traditional surgical approach are shown in FIG. 16. The physician drills an approximately 1.0 mm hole through the bone surrounding the cochlea through which the electrode is inserted; this process is referred to as the cochleostomy in the remainder of this article. The electrode stimulates the spiral ganglion cells to induce the sensation of hearing.

The cochlea is partitioned into several cavities: the scala tympani; scala vestibuli; and the scala media, which, for all practical purposes, can be ignored as it occupies only a small portion of the cochlear volume. Research has suggested that implanting the electrode into the scala tympani results in better hearing restoration [34]. But, it has also been reported that at most about 73% of cochlear implant procedures result in full insertion into the scala tympani [32]. The remaining 27% of implants are either fully inserted into the scala vestibuli or are initially inserted into scala tympani and then cross through the thin membranes (basilar and Reissner's membranes) separating the scala tympani from the scala vestibuli (see FIG. 17). Recent research has also suggested that the likelihood of scala tympani insertion is maximized using "soft" technique [49, 50]. In this approach, the implant is threaded at a tangential angle into the scala tympani, attempting to inflict as little stress as possible on the soft tissue within the cochlea.

The success of the soft technique is largely dependent on the angle of electrode insertion and the position of the cochleostomy, i.e., the angle should be tangential to the scala tympani and the cochleostomy should be centered on the scala tympani in the basal turn region (first turn of the spiral—see FIG. 16). Because the scala tympani is not visible in surgery, the surgeon must use other landmarks as a guide to estimate scala tympani position and orientation, a process requiring a great deal of expertise. Errors can occur here due to the imprecise nature of landmark-based, manual navigation as well as to inter-patient variations in the spatial relationship between the scala tympani and surgical landmarks [35, 51-54].

A method that could localize the scala tympani in clinical images could thus be part of a system that would help surgeons in determining the proper cochleostomy position and insertion angle relative to visible surgical landmarks. Using such a system could potentially result in more effective hearing restoration. For typical cochlear implant procedures, a conventional CT is acquired so that the surgeon can identify abnormalities along the surgical approach. But, the basilar membrane is invisible in these images, which makes automatic identification impossible using only the information available in these scans (see FIG. 17). To address this issue, one aspect of the invention provides a method that complements the information available in these images. This technique permits the fully automatic and accurate segmentation of both scalae.

The method according to one embodiment of the invention is based on a deformable model of the cochlea and its components. To create such a model, ex-vivo μCTs of the cochlea are used. In these scans, which have a spatial resolution that is much higher than the spatial resolution of clinical scans, intra-cochlear structures are visible (see FIG. 17). Thus, these structures can be segmented manually in a series of scans. The set of segmented structures can be used subsequently to create an active shape model, as proposed by Cootes et al. [25]. Once the model is created, it can be used to segment the structures of interest, which are only partially visible in the conventional CT images, using the limited information these images provide. In the following section, the method used to create the models and these models used to segment intra-cochlear structures in clinical CTs are described.

A. Data Set

Figure 17:
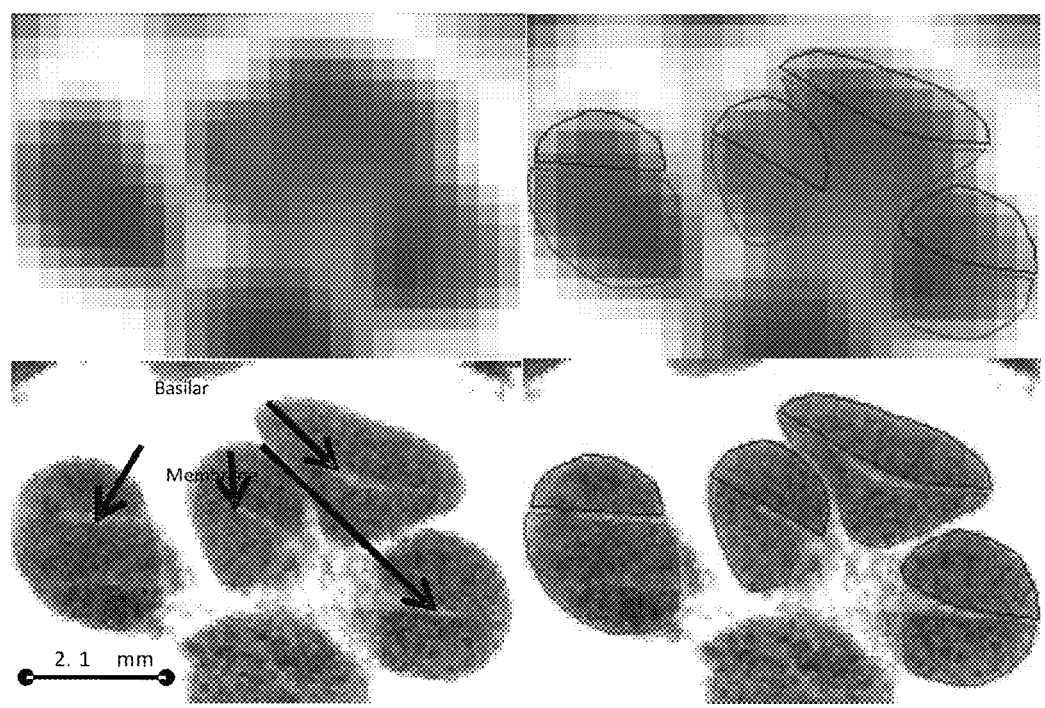
FIG. 17 shows CT (top) and µCT (bottom) of a cochlea specimen. Delineated in the right panels are the scala tympani (red) and scala vestibuli (blue).

In the example, the data set used to build the model includes image sets of six (one right and five left) cadaveric cochlea specimens received from the Vanderbilt School of Medicine's Anatomical Gifts Program. For each specimen, one μCT image volume is acquired with a Scanco μCT. The voxel dimensions in these images are 36 μm isotropic. For five of these specimens, one conventional CT image volume is also acquired with a Xoran XCAT fpVCT scanner. In these volumes, voxels are 0.3 mm isotropic. In each of the μCT volumes, the scala vestibuli and scala tympani were manually segmented. FIG. 17 shows an example of a conventional CT image and its corresponding μCT image.

B. Model Creation

In one embodiment, the approach used to model intra-cochlear anatomy is summarized in FIG. 18. It requires (1) establishing a point correspondence between the structures' surfaces, (2) using these points to register the surfaces to each other with a seven degrees of freedom similarity transformation (rigid plus isotropic scaling), and (3) computing the eigenvectors of the registered points' covariance matrix.

B.1. Image Registration Methods

As discussed in the next subsection, image registration is used in the process to establish correspondence between point sets. The registration scheme used in the embodiment is an affine, followed by a non-rigid registration process. Affine transformations are computed by optimizing 12 parameters (translation, rotation, scaling, and skew) using Powell's direction set method and Brent's line search algorithm [55] to maximize the mutual information [56] between the two images, where the mutual information between image A and B is computed as $$MI = H(A) + H(B) - H(A,B), \quad (7)$$

where $H(.)$ is the Shannon entropy in one image, and $H(.,.)$ is the joint entropy between the images. The entropy in the images is estimated as $$H(A) = -\sum_{k \in A} p(k) \log p(k), \quad (8)$$

in which $p(k)$ is the intensity probability density function, which is estimated using intensity histograms with 64 bins.

Non-rigid image registration is performed using the adaptive bases algorithm [57]. This algorithm models the deformation field that registers the two images as a linear combination of radial basis functions with finite support $$\vec{v}(\vec{x}) = \sum_{l=1}^{M} \vec{c}_l \Phi(\vec{x} - \vec{x}_l), \quad (9)$$

where $\vec{x}$ is a coordinate vector in $\mathbb{R}^d$, with d being the dimensionality of the images. $\Phi$ is one of Wu's compactly supported positive radial basis functions [58], and the $\vec{c}_l$'s are the coefficients of these basis functions. The $\vec{c}_l$'s that maximize the normalized mutual information [59] between the images are computed through an optimization process that combines steepest gradient descent and line minimization. The steepest gradient descent algorithm determines the direction of the optimization. The line minimization calculates the optimal step in this direction. The algorithm is applied using a multi-scale and multi-resolution approach. The resolution is related to the spatial resolution of the images. The scale is related to the region of support and the number of basis functions. Typically, the algorithm is started on a low-resolution image with few basis functions with large support. The image resolution is then increased and the support of the basis function decreased. This leads to transformations that become more and more local as the algorithm progresses.

B.2. Establishing Correspondence

To establish correspondence between surfaces, one μCT volume was arbitrarily chosen as a reference volume, $I_0$, and the remaining training volumes, $\{I_j\}_{j=1:N-1}$, were registered to the reference using the methods discussed in the previous section, creating the set of non-rigid transformations $\{\Psi_j\}_{j=1:N-1}$ such that $I_j \approx \Psi_j(I_0)$. The affine registration step required manual initialization since there was no standard orientation for the samples in the scans. The manually segmented reference surface $S_0$ was then deformed through each set of registration transformations into each target image space, creating the set $\{\Psi_j(S_0)\}$. Residual registration errors were corrected by manually adjusting the surfaces using a tool developed for this purpose. These additional transformations were combined with the transformations computed automatically to produce the set of compound transformations $\{\Psi_j^M\}$. Finally, for each ith vertex on each jth deformed reference surface $\Psi_j^M(\vec{S}_{0,i})$, the closest point on the respective training surface $\vec{p} \in S_j$ was found. A correspondence between this point $\vec{p}$ and the reference surface vertex $\vec{S}_{0,i}$ was established. Equivalently, $$\vec{S}_{0,i} \leftrightarrow p_{S_j}(\vec{S}_{0,i}) \quad (10)$$

such that $$p_{S_j}(\vec{S}_{0,i}) = \operatorname{argmin}_{\vec{p} \in S_j}(\|\Psi_j^M(\vec{S}_{0,i}) - p\|_2). \quad (11)$$

This results in one corresponding point on each jth training surface for every ith reference point. Using image registration to establish a correspondence between point sets was inspired by the work of Frangi et al. [60].

Once correspondence is established, each training surface is registered to the reference surface with a similarity transformation (rigid plus isotropic scaling), computed using standard point registration techniques [61]. Correspondence is established separately for the scala tympani and scala vestibuli, however, point registration is performed taking both structures into account simultaneously. This is done to maintain accurate inter-structure spatial relationships so that the shape model can be constructed with both structures simultaneously.

B.3. Computing the Shape Model

To build the model, the principal modes of shape variation are extracted from the registered training shapes. This is computed according to the procedure described by Cootes et al. [25]: First, the covariance matrix of the point sets' deviation from the mean shape is computed as $$C = \frac{1}{N} \sum_{j=1}^{N} (\vec{w}_j - \overline{w})(\vec{w}_j - \overline{w})^T, \quad (12)$$

where the $\vec{w}_j$'s are the individual shape vectors and $\overline{w}$ is the mean shape vector defined by $$\overline{w} = \frac{1}{N} \sum_{j=1}^{N} \vec{w}_j. \quad (13)$$

The shape vectors are constructed by stacking the 3D coordinates of all the points composing each structure into a vector. The modes of variation in the training set are then computed as the eigenvectors $\{\vec{u}_j\}$ of the covariance matrix, $$\{\lambda_j, \vec{u}_j\}_{j=1}^{N-1}: \lambda_j \vec{u}_j = C \vec{u}_j. \quad (14)$$

There are at most N-1 non-trivial eigenvalues, $\{\lambda_j\}$, because the rank of a covariance matrix of N linearly independent samples is N-1. The range of shapes within the training set can then be described by adding a linear combination of the eigenvectors, to $\overline{w}$, the mean shape. The eigenvalue associated with each eigenvector is equal to the variance explained by the jth mode of variation in the training set. Typical structures can be closely approximated by using a linear combination of the eigenvectors within two standard deviations of the mean. These modes of variation are extracted for the combined shape of both the scalae for all the samples in the training set.

C. Segmentation Using the Active Shape Model

In the embodiment, the procedure for segmentation with an active shape model is outlined in FIG. 19. As can be seen in the figure, the overall process follows the traditional active shape model approach, i.e., (1) the model is placed in the image to initialize the segmentation; (2) better solutions are found while deforming the shape only in ways that are described by the pre-computed modes of variation; and (3) eventually, after iterative shape adjustments, the shape converges, and the segmentation is complete. The following sections detail this approach.

C.1 Initialization

The first step to perform segmentation is to provide an initial position for the model in the target image. In one embodiment, the initialization process is performed by using an image registration-based initialization approach, in which an "atlas" is registered to the volume to be segmented, the "target." This atlas is a conventional CT volume in which the position of the scalae is known. To create this atlas, a full head clinical CT was selected (in plane voxel size of $0.218 \times 0.218$ mm$^2$, and slice thickness of 0.8 mm with 0.4 mm overlap). Next, a non-rigid transformation between the atlas volume and $I_0$, the μCT of the cochlea specimen used to create the model, was computed using image registration. Because the atlas volume and $I_0$ have very different fields of view, it was necessary to manually initialize this registration. Next, the scalae model points were projected from h to the atlas volume. Finally, visually identifiable errors in the resulting surfaces were manually corrected. This process results in a full head volume in which the position of the scalae and of the basilar membrane are known.

The atlas is used at segmentation time to initialize the model using the steps summarized in FIG. 19: (a) First, an automatic non-rigid registration is computed between the atlas and the target CTs. (b) Next, the scalae model points, which have known positions in the atlas, are transferred to the target image using the registration transformation. (c) Finally, to initialize the search, the shape model is simply fitted (the fitting procedure is described in the following section) to this set of points. The fitting procedure constrains the shape of the point-set to be similar to that of typical scalae, removing any unnatural shape changes that may have occurred due to the non-rigid registration transformation.

C.2 Searching Scheme

Once initialized, the optimal solution is found using an iterative searching procedure. At each search iteration, (a) an adjustment is found for each model point, and (b) the model is fitted to this set of candidate adjustment points (see FIG. 19). To find the candidate points, two approaches are used, one for "external" and another for "internal" model points. When the model was created, model points corresponding to the exterior of the cochlea were labeled as external points. All other model points, which are positioned inside the cochlea were labeled as internal points. For the internal points, it is impossible to determine the best adjustment using local image features alone, because there are no contrasting features inside the cochlea in CT. Therefore, the original initialization positions for these points, which were provided by image registration, are used as the candidate positions. The registration transformation, as the results will show, is sufficiently accurate to provide this useful information to the segmentation process. External points lie in regions with contrasting features in CT. Therefore, candidates for external points are found using line searches to locate strong edges. At each external point $\vec{y}_i$, a search is performed along the vector normal to the surface at that point. The new candidate point is chosen to be the point with the largest intensity gradient over the range of −1 to 1 mm from $\vec{y}_i$ along this vector.

The algorithm uses the approach just described to find a new candidate position for each point in the model. The next step is to fitted the shape model to these candidate points. A standard 7 degree of freedom point registration is performed, creating similarity transformation T, between the set of candidate points $\{\vec{y}_i'\}$ and the mean shape $\{\overline{w}_i\}$, where $\overline{w}_i$ are the 3D coordinates of the ith point in the mean shape. Then, the residuals $$\vec{d}_i = T(\vec{y}_i') - \overline{w}_i \tag{15}$$

are computed. The modes of variation that were previously extracted are fitted to the residuals by taking the inner product between each eigenvector with the full residual vector, $$b_j = \vec{u}_j^T \vec{d}, \tag{16}$$

where $\vec{d}$ is composed of $\{\vec{d}_i\}$ stacked into a single vector. Eq. (15) results in a scalar $b_j$ corresponding to each eigenvector $\vec{u}_j$ that quantifies how much of the deviation of this shape from the mean shape is explained by $\vec{u}_j$. The final approximation to the shape is computed by passing the sum of the scaled eigenvectors plus the mean shape through the inverse transformation, equivalently, $$\vec{y}_i = T^{-1}\left(\overline{w}_i + \sum_{j=1}^{N-1} b_j \vec{u}_{j,i}\right), \tag{17}$$

where $\vec{u}_{j,i}$ is the ith 3D coordinate of the jth eigenvector. As suggested by Cootes [25], the magnitude of the $b_j$'s are constrained such that $$\sqrt{\sum_{j=1}^{N-1} \frac{b_j^2}{\lambda_j}} \leq 3, \tag{18}$$

which enforces the Mahalanobis distance between the fitted shape and the mean shape to be no greater than 3. This constrains the shape such that its deviation from the mean is reasonable relative to the shape variations described by the training set.

At each iteration, new candidate positions are found and the model is re-fitted to those candidates. The active shape model converges when re-fitting the model results in no change to the surface.

D. Validation

Segmentation was performed on CT's of five of these cochlea specimens using a leave-one-out approach, i.e., the volume being segmented is left out of the model. Thus, only four modes of variations were available for each segmentation validation. Because these samples were excised specimens, rather than whole heads, the initial registration with the full head CT used as the atlas required manual initialization—however, in practice the approach is fully automatic. To validate the results, again, the set of corresponding μCT volumes is exploited. Each μCT was rigidly registered to the corresponding CT of the same specimen. The manually delineated scalae segmentations were then projected from the μCT to CT space. Finally, Dice similarity coefficient (DSC) [27] and surface errors were computed between automatic segmentations and the registered manual segmentations to validate the accuracy of the results. DSC measures volumetric overlap between two surfaces $S_1$ and $S_2$ using the equation $$DSC(S_1, S_2) = \frac{2N(S_1 \cap S_2)}{N(S_1) + N(S_2)}, \qquad (19)$$

where $N(S_1 \cap S_2)$ is the number of overlapping voxels within the surfaces, and $N(S_1) + N(S_2)$ is the sum of the number of voxels within each surface. DSC ranges from 0, corresponding to no volumetric overlap, to 1, which corresponds to perfect volumetric overlap. A larger DSC between the automatic and manual segmentations indicates higher accuracy.

Surface errors are computed by measuring mean and maximum distances between automatic and manually segmented surfaces. The distance from a vertex $\vec{p}$ on surface $S_1$ to surface $S_2$ can be computed using the equation $$d(\vec{p}, S_2) = \min_{\vec{q} \in S_2}(\|\vec{p} - \vec{q}\|_2). \qquad (20)$$

Then, the mean and maximum distances between the two surfaces can be computed as $$d_{mean}(S_1, S_2) = \operatorname{mean}_{\vec{p} \in S_1} d(\vec{p}, S_2),$$

$$d_{max}(S_1, S_2) = \max_{\vec{p} \in S_1} d(\vec{p}, S_2) \qquad (21)$$

In general, $d_{(\cdot)}(S_1, S_2) \neq d_{(\cdot)}(S_2, S_1)$, i.e., the distance measures are not symmetric. Thus, to accurately characterize the surface error, surface distances are computed in the forward (automatic-to-manual) direction as well as the reverse (manual-to-automatic) direction and include both measurements in the results. A smaller distance between the automatic and manually segmented surfaces indicates higher accuracy.

E. Results and Discussions

The model was constructed with a total of approximately 15000 unique sets of corresponding surface points. The eigenvalues of the 5 independent modes of variation for the model are given in Table 1.

TABLE 1

Eigenvalues of the modes of variation for the model.

| | Mode of Variation | | | | |
|---|---|---|---|---|---|
| | 1 | 2 | 3 | 4 | 5 |
| Eigenvalues | 555.10 | 330.39 | 183.06 | 108.97 | 72.04 |
| % of Total Variance | 44.60 | 26.54 | 14.71 | 8.76 | 4.36 |

Figure 20:
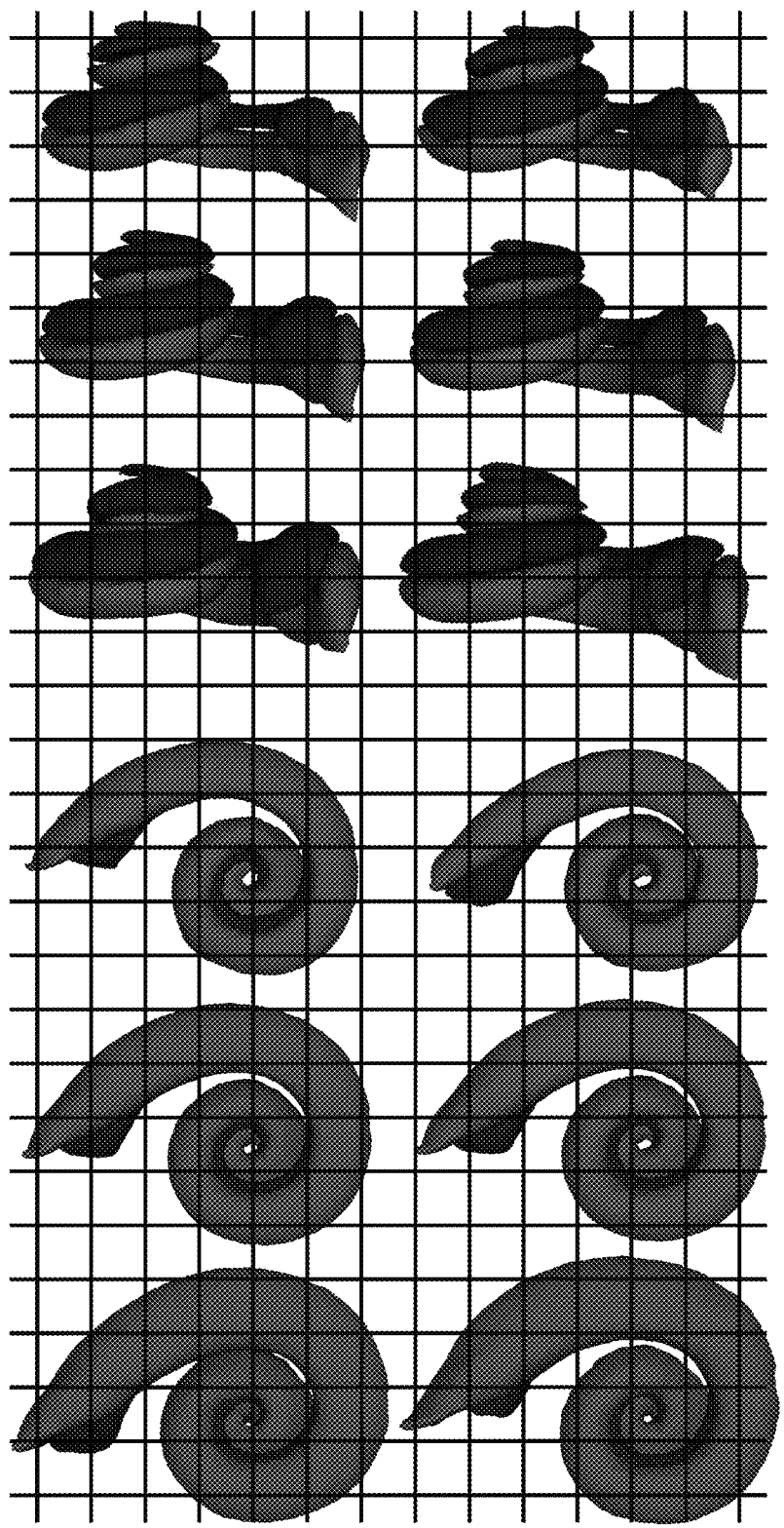
FIG. 20 shows first (top row) and second (bottom row) modes of variation of the scala tympani (red) and vestibuli (blue) in the point distribution model. On the left are (from left to right) −2, 0, and +2 standard deviations from the mean in Posterior-to-Anterior view. The same modes are shown on the right in Medial-to-Lateral view.
Figure 21:
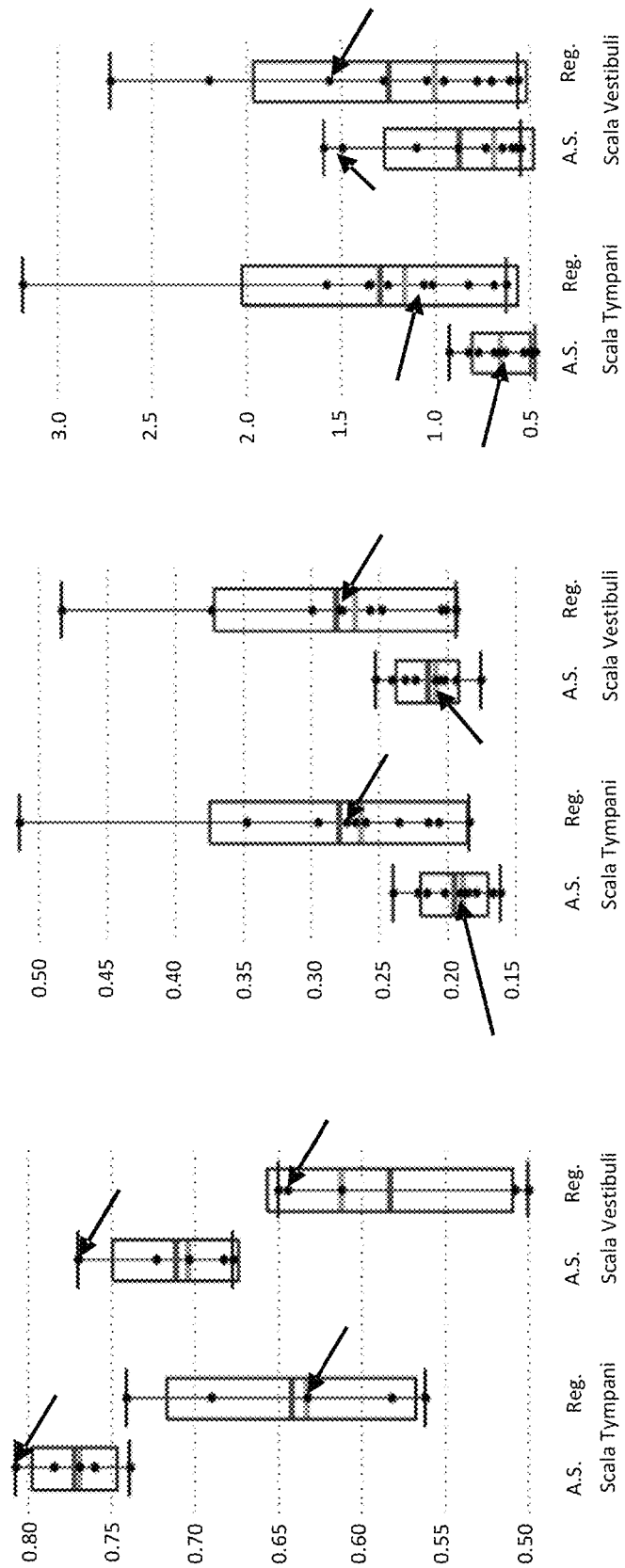
FIG. 21 shows quantitative segmentation results. Shown are the distributions of the DSC (left), mean surface distance in mm (middle), and max surface distance in mm (right) for the results of the active shape model (A.S.) and registration alone (Reg.). Arrows indicate the results for the experiment shown in FIG. 7.

At a range of two standard deviations, the maximum displacement of any point on the scala tympani or scala vestibuli surfaces are approximately 1.0 mm, and mean displacements are approximately 0.15 mm. Points on the basal turn (the first turn of the spiral) vary by approximately 0.35 mm. In the basal turn, the basilar membrane varies by approximately 0.15 mm. The first two modes of variation can be visually appreciated in FIG. 20. It appears that the first mode of variation is capturing changes in the length of the basal turn, the second mode of variation is capturing changes in the width of the basal turn, and both are capturing changes in the width and angle of the second and third turns of the cochlea Quantitative comparisons between the manual segmentations of the scalae, transformed from μCT to the respective conventional CT, and the automatic segmentations are shown in FIG. 21. DSC for measuring volumetric overlap and bi-directional mean/max surface distances are computed between each pair of automatic and manual segmentations. FIG. 21 shows the overall distributions of these recorded values. The green bars, red bars, blue rectangles, black dots, and black I-bars denote the median, mean, one standard deviation from the mean, individual data points, and the overall range of the data set, respectively. Results for segmentation with the active shape model are shown side by side with results achieved using non-rigid registration alone. Arrows indicate the results from the experiment shown in FIG. 22. The active shape model achieves mean DSC of approximately 0.77 for the scala tympani and 0.72 for the scala vestibuli. For most structures, a DSC of 0.8 is typically considered good [28]. However, this measure can be unforgiving for very thin, complicated structures, such as the scalae, which range from about 1 to 4 voxels thick along their length. In general, for structures with a relatively large surface area-to-volume ratio, 0.7 is typically considered a high DSC. The active shape model effectively improves the volumetric overlap from the results achieved by registration alone in every experiment. A consistent decrease in mean surface errors from an average 0.28 mm with registration to 0.20 mm (<1 voxel) with the active shape model approach can also be seen. Maximum surface errors are on average decreased from 1.3 mm using registration to 0.8 mm by using the active shape model approach. In fact, with the active shape model, all surface errors for scala tympani segmentation are sub-millimetric. The improvements when using the active shape model are all statistically significant for each metric.

Figure 22:
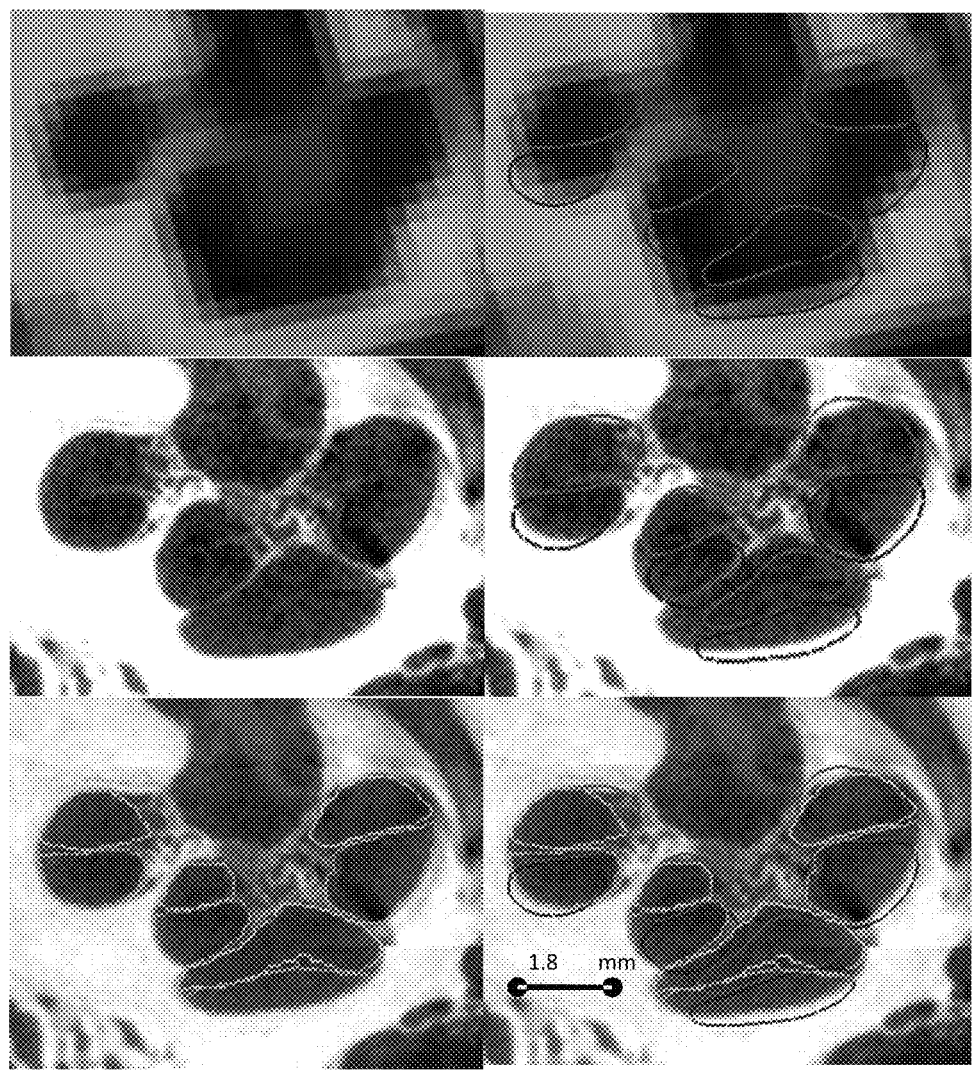
FIG. 22 shows contours of representative segmentation results. Automatic segmentation results for the scala tympani (red) and scala vestibuli (blue) are shown overlaid with the conventional CT (top row), and registered µCT (middle and bottom rows), and are compared to manually delineated contours of the scala tympani (light blue) and scala vestibuli (green).
Figure 23:
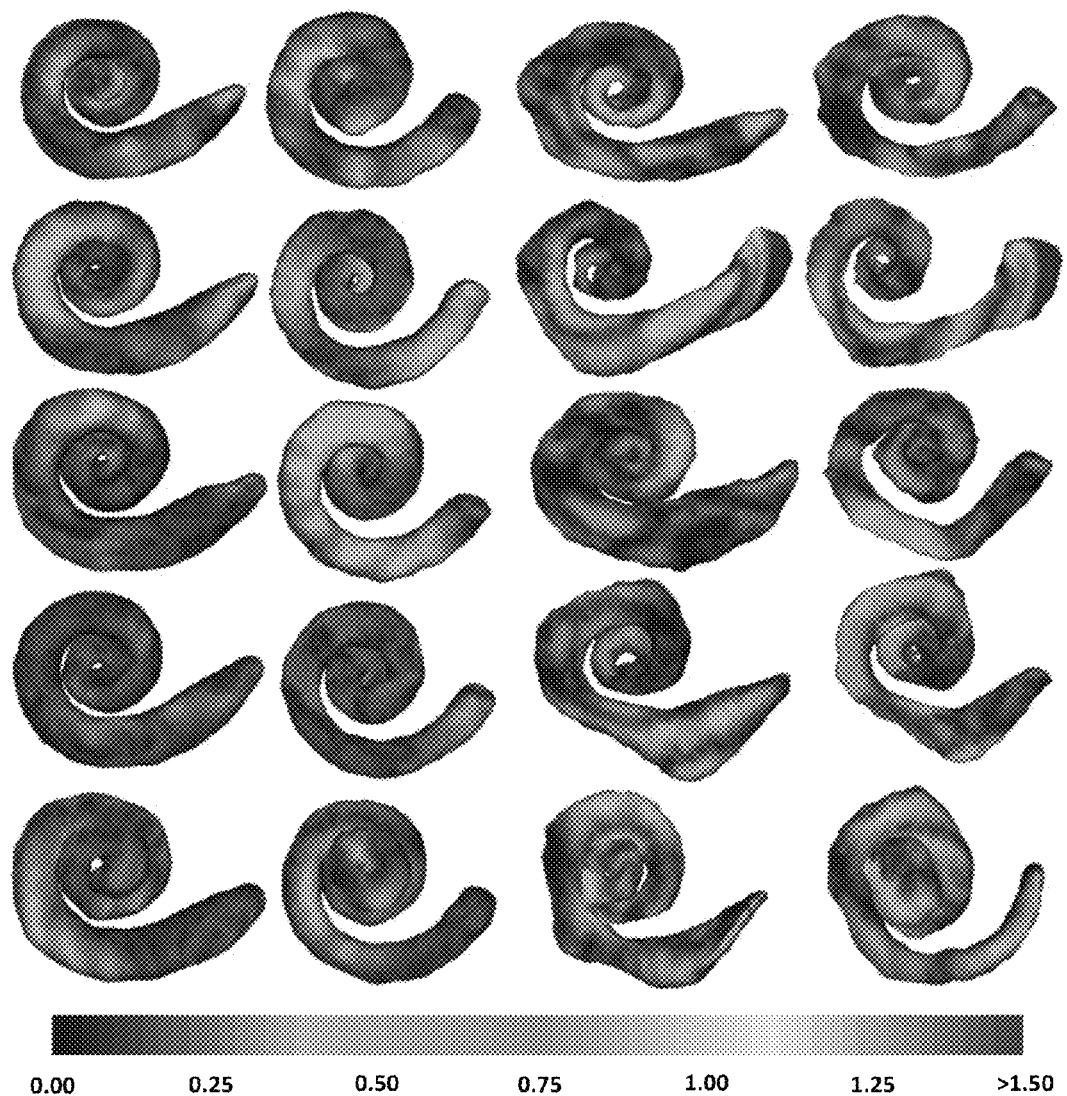
FIG. 23 shows segmentations color encoded with error in mm for the experiments 1-5 (Up to Down). (Left to Right) Active shape model segmentation of the scala tympani, scala vestibuli, atlas-based segmentation of the scala tympani, scala vestibuli.
Figure 24:
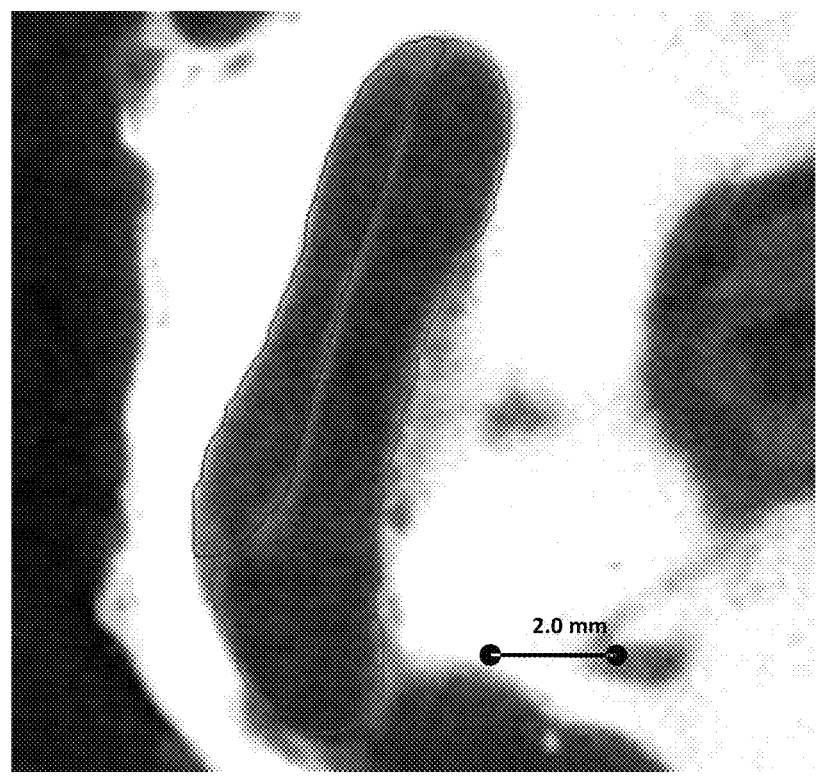
FIG. 24 shows µCT of a cadaveric cochlea in axial view. Delineated are Scala Tympani (red) and Scala Vestibuli (blue).

The results can be visually confirmed in FIGS. 22 and 23. Shown in FIG. 22 are contours of a representative automatic segmentation overlaid with the CT (the volume on which segmentation was performed) and the corresponding registered μCT. In the figure, the contours achieved by automatic segmentation of the CT can be compared to the contours manually delineated in the high resolution μCT. Local surface error maxima that are apparent in the μCT are less than 2 voxels width in the CT. Shown in FIG. 23 are the automatic segmentations for all 5 experiments, where the surfaces are color encoded with the distance to the manually segmented surface. It can be seen that the active shape model results in mean surface errors under 0.3 mm (<1 voxel) for the majority of the structure with typical average maximum errors of about 0.8 mm (<3 voxels). The active shape model converges to a surface that looks anatomically correct, whereas registration-based segmentation alone converges to unnatural, irregular surfaces.

According to the embodiments of the invention, an active shape model-based approach for identifying structures that are partially visible in conventional imaging is disclosed. In this approach, high resolution images of cadaveric specimens are used to serve two functions. First, they provide information necessary to construct a shape model of the structure, permitting segmentation of the structure in conventional imaging by coupling information from the image and non-rigid image registration to drive an active shape model to an accurate solution. Second, the high resolution images are used to validate the results. This is performed by projecting manually segmented structures from high resolution to conventional images using image registration, and comparing those structures to automatic segmentations. In one embodiment, this approach is applied to identify intra-cochlear anatomy in CT and validate the results; however, the approach is generic, and could theoretically be applied to other structures that are fully visible only in high resolution imaging.

While the number of samples used to build the model is relatively small, the leave-one-out study presented here suggests that there are enough samples for the active shape model to approximate the range of typical, non-malformed cochleae. This technology has, in fact, already been integrated into a system to assess post-operative electrode position [8, 62], which has successfully been used to identify scalae and electrode position in 16 patients [63]. The methods presented in this paper are able to automatically capture the non-rigid variations of the scalae for accurately assessing electrode position, which differs from the conventional approach where a rigid model of the anatomy is manually align with the image to identify electrode position [34, 64]. The scalae segmentation method has also been used for pre-operative planning of minimally invasive methods in 18 ears [65]. These studies and the results presented in this paper suggest that the model is powerful enough to capture the typical variations of the cochlea.

This work has shown that it is possible to accurately identify the location of the scala tympani and scala vestibuli using conventional CT. This is possible because the position of the intra-cochlear membrane separating the scalae varies predictably with respect to the rest of the cochlea. The approach accurately locates the basilar membrane in conventional CT by attracting the exterior walls of the models of intra-cochlear anatomy towards the edges of the cochlea. This approach achieves DSC of approximately 0.75, sub-millimetric maximum error distance for the scala tympani, and produces solutions that appear qualitatively reasonable. These results suggest that the approach can provide the surgeon with explicit knowledge of the location of surgical targets.

Automatic Identification of Cochlear Implant Electrode Arrays for Post-Operative Assessment This exemplary embodiment of the invention discloses an approach based on parametric Gradient Vector Flow snakes to segment the electrode array in post-operative CT. By combining this with existing methods for localizing intra-cochlear anatomy, a system that permits accurate assessment of the implant position in vivo is developed. The system is validated using a set of seven temporal bone specimens. The algorithms were run on pre- and post-operative CTs of the specimens, and the results were compared to histological images. It was found that the position of the arrays observed in the histological images is in excellent agreement with the position of their automatically generated 3D reconstructions in the CT scans.

In one embodiment, the algorithms require only a conventional pre-operative CT, such as one that is typically acquired prior to cochlear implantation, and a post-operative CT, of which image quality is not as important. In fact, good results are achieved using flat-panel volumetric CT (fpvCT), which only administers about one quarter the dose of radiation compared to that of a conventional CT. Thus, the position of the implant can be assessed in vivo, requiring only one extra CT that is of low radiation dose. This is of significance, because information about the location of the electrode would permit correlating placement and hearing restoration. It could also be used to give surgeons technical feedback and to aid implant programming, ultimately helping to better restore the patient's hearing.

Determining the intra-scalar position of the implant requires locating the electrode, as well as the scala tympani and scala vestibuli. Although finding the scalae in CT is not a straightforward task, the inventors have previously presented and validated very accurate methods to accomplish this in pre-operative CT [35]. Note that it is currently not feasible to locate the scalae in post-operative imaging due to the artifact introduced by the metallic electrodes. Since methods exist to locate the scalae in preoperative CT, the focus of this paper is to present a robust algorithm for locating the position of the electrode in post-operative CT.

The approach can be summarized as follows. The scalae are segmented in the preoperative CT using the methods proposed in [35]. Next, the post-operative CT is rigidly registered to the preoperative CT, giving us a very accurate localization of the scalae in the post-operative image. Then, the electrode is localized using techniques based on parametric Gradient Vector Flow (GVF) snakes [66, 67]. These electrode segmentation techniques are detailed as follows.

A. Methods

The algorithm to be presented is summarized in the following pseudocode (Algorithm 1). The following sections detail this approach.

---

Algorithm 1. Method for Localizing Electrode Arrays
Initialize:
    Project curve from atlas to target via non-rigid transformation
Iterate Until Convergence:
    Update curve by solving Eqn. (28)
    Resample curve points
Finalize:
    Update curve by solving Eqn. (30)
    Resample curve points
    Project surface onto curve using thin-plate splines

---

A.1 Segmentation Model

Figure 25:
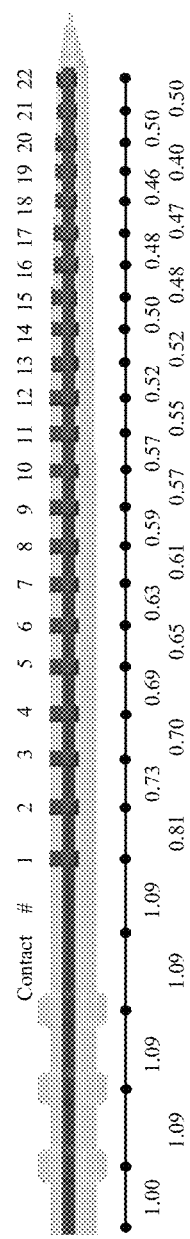
FIG. 25 shows model of the Cochlear Contour Advance electrode array. Shown are the surface model (top), the corresponding curve points (middle), and the distances in mm between curve points (bottom).

The electrode is modeled as a set of points representing the centerline of the array. Once these centerline points are matched to the metallic artifact in the image, a model of the array surface can be projected onto the centerline to get an accurate representation of the electrode location. This article focuses on the use of the Cochlear™ Contour Advance® electrode array, but the method is applicable to many types of electrodes simply by changing the centerline model and the surface model of the array itself. The Cochlear array and the centerline model are shown in FIG. 25. The placement of centerline points with respect to the array is somewhat arbitrary, but as a matter of convenience, the points in the model were chosen such that each electrode in the array is aligned with a point. Points are also placed along the array prior to the contact position in a few locations. The non-contact region is included in the model because the entry point to the cochlea usually lies in this region. Throughout the segmentation process, the centerline is restricted such that it is composed of this set of points separated by the distances as shown in the array model.

A.2 Initialization

To initialize the iterative segmentation approach, a reasonable initial placement of the centerline model in the target image must be found. It is chosen to use image registration to initialize the segmentation with an atlas-based approach. Prior to electrode segmentation, the scalae are segmented with a process that is initialized using registration between an "atlas" CT and the target pre-operative CT [35].

The registration scheme used is an affine, followed by a non-rigid registration process. Affine transformations are computed by optimizing translation, rotation, scaling, and skew parameters using Powell's direction set method and Brent's line search algorithms [55]. Mutual information is the similarity measure that is maximized and is computed between images X and Y using the equation $$MI=H(X)+H(Y)-H(X,Y), \tag{22}$$

where H(.) is the Shannon entropy of an image, and H(. , .) is the joint entropy between the images [56]. An estimation of the entropy in an image can be computed as:

$$H(X) = -\sum_{k \in X} p(k) \log p(k), \tag{23}$$

where p(k) is the intensity probability density function and is estimated using histograms with 64 bins.

Non-rigid image registration is performed using the adaptive bases algorithm [57]. This algorithm models the deformation field that registers the two images as a linear combination of radial basis functions with finite support $$\vec{v}(\vec{x}) = \sum_{l=1}^{M} \vec{c}_l \Phi(\vec{x} - \vec{x}_l), \tag{24}$$

where $\vec{x}$ is a coordinate vector, $\Phi$ is one of Wu's compactly supported positive radial basis functions [58], and the $\vec{c}_l$'s are the coefficients on the basis functions. The $\vec{c}_l$'s that maximize the normalized mutual information [59] between the images are computed using a steepest gradient descent and line minimization optimization approach. The direction of optimization is determined using the steepest gradient computation, and the optimal step in that direction is found using the line minimization calculation. The algorithm is applied using a multi-scale and multi-resolution approach. The algorithm begins optimization on a low-resolution image with few basis functions each having large support. The image resolution is then increased and the number and support of the basis function is decreased. This leads to transformations that become more local as the algorithm progresses.

To obtain a non-rigid transformation between the atlas and target cochleae, first, an affine transformation is computed between the full head images. This is followed by local affine, then non-rigid registrations over the region surrounding the cochlea. A non-rigid transformation between the same atlas CT and the post-operative CT is achieved by combining this compound non-rigid transformation between the atlas and pre-operative CT with the rigid transformation that registers the pre- and post-operative CT. This registration approach is much more effective than directly registering the atlas to the post-operative CT, because accurate non-rigid registration of the cochlea would not be possible due to the strong metallic artifact in the post-operative CT. The rigid transformation between pre- and post-operative CTs can be computed using the affine registration process described above while constraining the transformation to be rigid by optimizing only the translation and rotation parameters.

A curve was manually defined in the atlas image at a position that is typical for a cochlear implant. To initialize the segmentation, this permanently defined curve is projected onto the target post-operative CT via the non-rigid transformation, providing a rough estimation of the implant position.

A.3 Locating the Centerline of the Array

Figure 26:
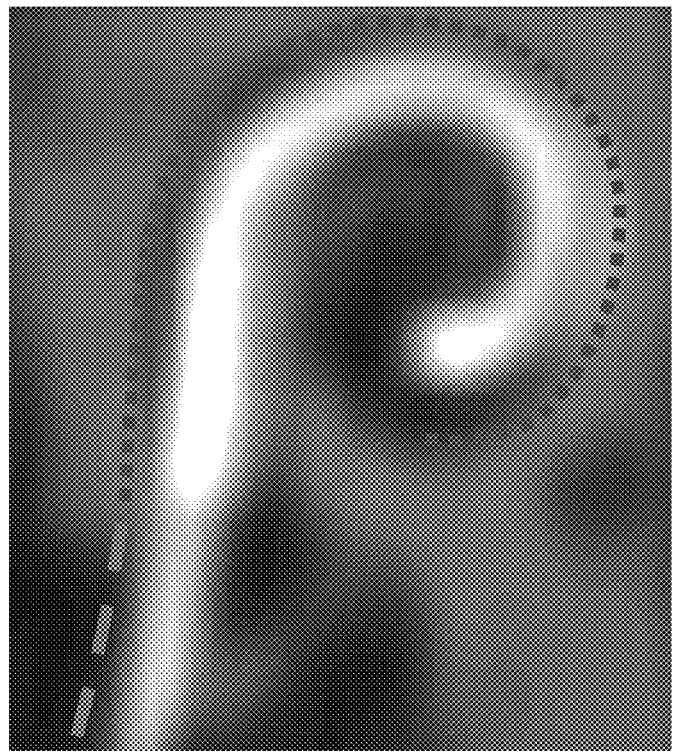
FIG. 26 shows implanted electrode array. Curves are used to indicate the electrode contact region (red) and non-contact region (green).

The electrode array produces a metallic artifact in CT that is much brighter than surrounding anatomical structures (see FIG. 26). The medial axis of the artifact should correspond to the centerline of the electrode array. Thus, the next step in the algorithm is a process to localize the centerline of the metallic artifact in the image. Once the curve is initialized, tracking the centerline of the artifact is achieved by minimizing the energy equation $$E=\int_0^1 w_1\|v'(s)\|^2+w_2\|v''(s)\|^2+E_{ext}(v(s))ds, \tag{25}$$

which is the standard snake energy equation. v(s) is the position of the parameterized curve at s, $w_1$ and $w_2$ are tension and rigidity weighting terms, and $E_{ext}$ is the external energy term. Following the traditional formulation, a curve that minimizes E satisfies the corresponding Euler-Lagrange equation $$-w_1v''(s)+w_2v''''(s)+\nabla E_{ext}(v(s))=0. \tag{26}$$

Figure 27:
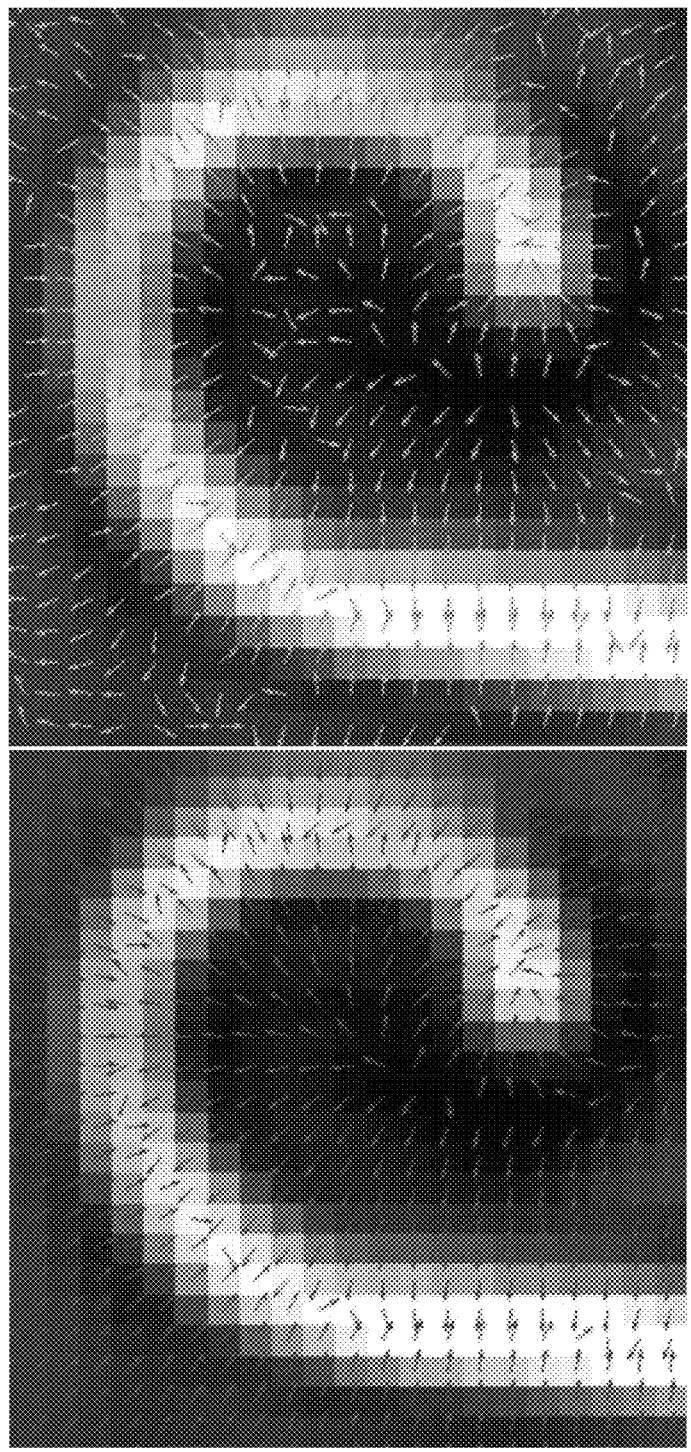
FIG. 27 shows normalized vector fields produced by GVF (left) and standard gradient computations (right).
Figure 28:
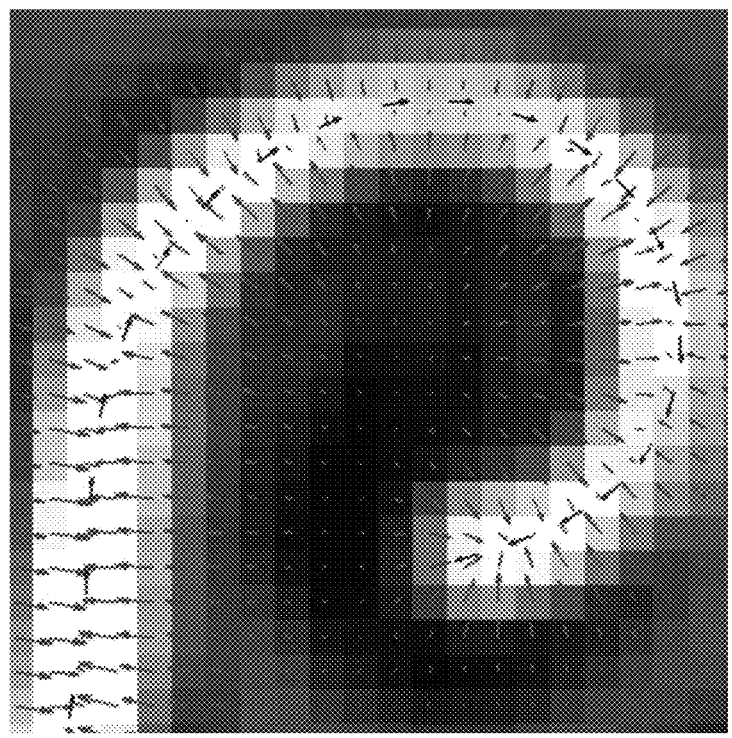
FIG. 28 shows example of GVF field (red arrows) and forward force (blue arrows).

As can be seen in FIG. 26, the metallic artifact in the image is much brighter than any anatomical structure. Therefore, an external energy that will attract the model to the bright regions of the image is derived. One approach would be to use the intensity gradient of the image as the external force. An example of this is shown in the right panel of FIG. 27. In the figure, normalized gradient vectors are overlaid on the image to show the direction of the gradient force throughout the image. The gradient vectors point towards the centerline in a very local region around the array. But, a few voxels away from the array, the gradient vectors point in various directions. Thus, this force will result in a snake with a very limited capture range. This limited capture range led us to a solution based on Gradient Vector Flow (GVF). GVF has been found to be a very robust attraction force for snake-like segmentation models. The algorithm produces a field of vectors over the range of the image that point towards bright regions with very nice field properties. In the original paper, GVF was applied to gradient magnitude images; here it can be applied to the image itself. The field is computed by minimizing an energy functional that favors the gradient vectors where the image gradient is strong and favors spatially smooth variation of neighboring vectors in homogeneous regions of the image. The resulting optimization process effectively diffuses the gradient vectors from bright regions throughout the image using equations identical to those that describe heat conduction. A normalized gradient vector flow vector field is shown in the left panel of FIG. 27 to show the direction of GVF vectors throughout the image. The vectors clearly point towards the array over a much larger range than the intensity gradient vector field. An example of a GVF vector field with properly scaled vectors is shown in FIG. 28. As can be seen from the figure, GVF produces a smoothly varying vector field that points towards the centerline of the metallic artifact in the image with stronger vectors closer to the centerline.

The GVF force alone is not enough to ensure accurate results. A large portion of the implant lead in which one is not interested extends laterally beyond the contact region into the non-contact region and also produces bright metallic artifact in the image (see FIG. 26). Thus, the GVF vector field will point toward the contact region as well as the rest of the lead. To ensure that the electrode model is attracted to this electrode contact region, another force must be introduced Akin to the balloon force introduced by Cohen and Cohen [8], a "forward" force is introduced, which has the effect of pushing the curve forward. Therefore, the external force is defined as $$\nabla E_{ext}(v(s)) = -w_3 \hat{v}'(s) - \vec{f}(v(s)), \quad (27)$$

where $\vec{f}$ is the GVF field and $w_3$ is a weighting parameter on the forward force that scales the length of the forward force vector. The v' term defines the direction of the forward force, such that the curve is pushed forward in the direction of its derivative. Example forward force vectors are shown in FIG. 28.

A solution to Eqn. (26) can be approximated by applying finite differences and switching to a discrete, time-varying, iterative formulation. Taking into account a time-step equal to 1, Eqn. (26) is satisfied by solving $$v_i^t + w_1(2v_i^t - (v_{i-1}^t + v_{i+1}^t)) + w_2(6v_i^t - 4(v_{i-1}^t + v_{i+1}^t) + (v_{i-2}^t + v_{i+2}^t)) = \quad (28)$$
$$v_i^{t-1} + w_3(t)\frac{(v_{i+1}^{t-1} - v_{i-1}^{t-1})}{\|v_{i+1}^{t-1} - v_{i-1}^{t-1}\|} + \vec{f}(v_i^{t-1})$$
$$2 < i < N - 1$$

$$v_i^t + w_1(2v_i^t - (v_{i-1}^t + v_{i+1}^t)) = v_i^{t-1} + w_3(t)\frac{(v_{i+1}^{t-1} - v_{i-1}^{t-1})}{\|v_{i+1}^{t-1} - v_{i-1}^{t-1}\|} + \vec{f}(v_i^{t-1})$$
$$i = 2, N - 1$$

$$v_i^t - w_1(2v_{i+1}^t - (v_i^t + v_{i+2}^t)) = v_i^{t-1} + w_3(t)\frac{(v_{i+1}^{t-1} - v_i^{t-1})}{\|v_{i+1}^{t-1} - v_i^{t-1}\|} + \vec{f}(v_i^{t-1})$$
$$i = 1$$

$$v_i^t - w_1(2v_{i-1}^t - (v_{i-2}^t + v_i^t)) = v_i^{t-1} + w_3(t)\frac{(v_i^{t-1} - v_{i-1}^{t-1})}{\|v_i^{t-1} - v_{i-1}^{t-1}\|} + \vec{f}(v_i^{t-1})$$
$$i = N.$$

Eqn. (28) is solved iteratively for $\{v_i^t\}_{i=1}^N$, where the terms weighted by $w_1$ and $w_2$ are approximations of v"(s) and v""(s) and are the standard finite difference formulation. $\hat{v}'(s)$ is approximated by the term weighted by $w_3$, which is a finite difference approximation of the curve derivative. In practice, this is solved easily using well-known linear system solvers. The first conditional in Eqn. (28) is applied to all the curve points where boundary conditions are not an issue. Central differences are used to approximate all derivatives. The second equation is applied to the points adjacent to the endpoints. Here, the rigidity term, v""(s) is removed. This is done because a central difference approximation is not possible, and the forward and reverse approximations are not well-behaved. The last two conditional equations apply to the endpoints. Again, there is no rigidity term. The v"(s) tension term is also removed, and is replaced with a linear extrapolation-based smoothing term. The direction of linear extrapolation is the negative of the non-central finite difference approximation of v"(s), which is not well-behaved for this open-curve snake model. The curve derivative is approximated with forward and reverse differences. $w_1$ and $w_2$, the tension and rigidity weightings, are chosen to be constant values of 0.1 and 0.05. The forward force weighting $w_3$ is treated as a function of time and is equal to $$w_3(t) = \begin{cases} 3e - 4t & t < 500 \\ 0.15 & t \geq 500 \end{cases}. \quad (29)$$

This is a piecewise-linear, continuous function of t, such that when the curve is initially evolving, the forward energy has very little influence and the curve evolves toward the center of the artifact. The forward energy weighting increases over time and reaches a maximum of 0.15 well after the curve should be on the artifact centerline. All weighting values were chosen experimentally.

This time varying formulation is used in an iterative process to accurately locate the centerline of the metallic artifact. At each iteration, Eqn. (28) is solved and the curve is resampled. The re-sampling process is applied to ensure that the distances between points are maintained as specified by the model (see FIG. 25). To re-sample the curve, the tip point is treated as fixed, and the remaining curve points are sequentially re-sampled from the electrode tip point toward the lead. When necessary the lead points are defined using linear extrapolation. Repeating this iterative curve update and re-sampling process until convergence produces a very accurate estimation of the artifact centerline.

A.4 Centerline Adjustment

Figure 29:
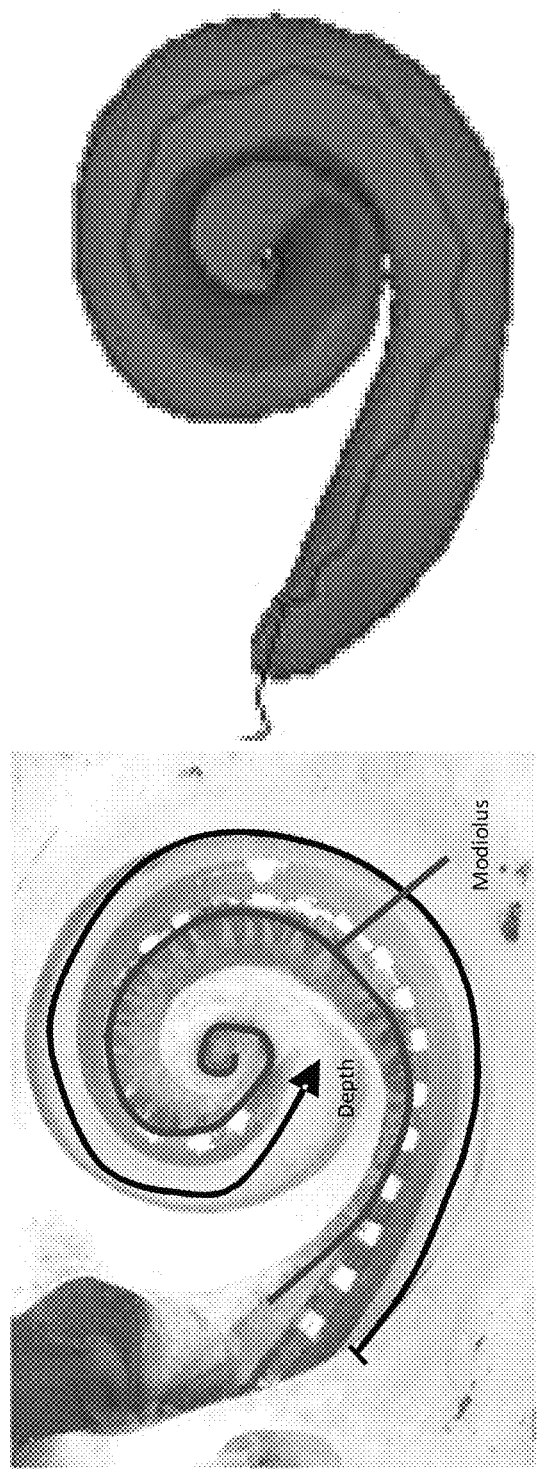
FIG. 29 shows histological image (left) and CT reconstruction (right) of cochlear implant. The manually localized artifact centerline from CT (blue line) seen in the Scala Tympani (red surface) is distinctly different from actual electrode position in histological image.

Experiments have shown that the position of the centerline of the metallic artifact in CT does not exactly agree with the position of the centerline of the array in histological imaging (see FIG. 29). In fact, the metallic artifact is located further laterally in the cochlea and also appears to terminate at a cochlear depth prior to the actual tip of the electrode. Work is currently being done to understand this phenomenon; however, for the purposes of segmentation, one further step can be employed to make the centerline more accurate with respect to the true anatomical location. In this adjustment step, another term is included, which moves the centerline towards the medial wall of the cochlea, and the strength of the forward force is increased. This step is performed by solving $$v_i^t + w_1(2v_i^t - (v_{i-1}^t + v_{i+1}^t)) + w_2(6v_i^t - 4(v_{i-1}^t + v_{i+1}^t) + (v_{i-2}^t + v_{i+2}^t)) = \quad (30)$$
$$v_i^{t-1} + w_4\frac{(v_{i+1}^{t-1} - v_{i-1}^{t-1})}{\|v_{i+1}^{t-1} - v_{i-1}^{t-1}\|} + w_5\hat{n}_i$$
$$2 < i < N - 1$$

$$v_i^t + w_1(2v_i^t - (v_{i-1}^t + v_{i+1}^t)) = v_i^{t-1} + w_4\frac{(v_{i+1}^{t-1} - v_{i-1}^{t-1})}{\|v_{i+1}^{t-1} - v_{i-1}^{t-1}\|} + w_5\hat{n}_i$$
$$i = 2, N - 1$$

$$v_i^t - w_1(2v_{i+1}^t - (v_i^t + v_{i+2}^t)) = v_i^{t-1} + w_4\frac{(v_{i+1}^{t-1} - v_i^{t-1})}{\|v_{i+1}^{t-1} - v_i^{t-1}\|} + w_5\hat{n}_i$$
$$i = 1$$

$$v_i^t - w_1(2v_{i-1}^t - (v_{i-2}^t + v_i^t)) = v_i^{t-1} + w_4\frac{(v_i^{t-1} - v_{i-1}^{t-1})}{\|v_i^{t-1} - v_{i-1}^{t-1}\|} + w_5\hat{n}_i$$
$$i = N,$$

where $\hat{n}$ is a vector normal to the curve that points toward the medial wall of the cochlea, $w_4$ is a distance weighting on the forward force set equal to 0.35, and $w_5$ is a distance weighting on the normal vector set to 0.15. Both weightings were chosen experimentally.

A.5 Electrode Array Surface Reconstruction

To finish the segmentation, the electrode array surface must be reconstructed around the extracted centerline. To do this, a thin-plate spline (TPS) transformation is used [55]. This is a non-rigid transformation that is computed by matching two corresponding point-sets. The first point-set is extracted by acquiring points in cylinder patterns around each point along the extracted centerline curve, where the cylinders are chosen to be identical in radius to the array. This point set is matched to points acquired in the same cylinder pattern around the corresponding centerline points in the electrode surface model. Cylindrical point-sets are used, rather than just the centerline points, because (1) a TPS transformation between points in a 3D space and points in a straight line is ill-conditioned, and (2) matching cylinders that are identical in radius to the electrode array will lead to a TPS that includes the entire electrode array within the interpolating region of the transformation. This is desirable because non-rigid transformations, like those based on TPS, are generally much more accurate and well-behaved in the interpolation, rather than the extrapolation, regions. To reconstruct the array surface, the electrode surface model is passed through the TPS-based transformation that is defined by the two point-sets.

A.6 Validation

To validate the localization of the centerline of the artifact, automatic localization results are compared to the centerlines of manual segmentations of the electrode artifact using seven specimens. Pre- and post-operative CTs (Xoran XCAT fpvCT with voxel size 0.3×0.3×0.3 mm$^3$) were acquired for each specimen, and the proposed reconstruction approach was carried out using these CTs. After the software is executed, each electrode artifact localization was validated by measuring the closest distance between the automatic curve and the manual segmentation centerline.

Next, the centerline adjustment procedure is used to identify the position of the array in CT that matches the true position of the array as seen in histological images, so that it can be used for accurate qualitative assessment of electrode position. As such, the surface reconstruction through qualitative assessment is validated. The important properties of the array position to be measured include the depth (see FIG. 25), the cavity in which each contact is located, and the proximity to the modiolus of each contact (also shown in FIG. 28). These three quantities are qualitatively measured by examining the histological images and the automatic reconstructions independently, and then compare the two results.

B. Results and Discussions

In one embodiment, all algorithms were implemented in C++. Other program languages can also be utilized to practice the invention. The whole process of localizing the scalae and electrode array takes approximately 3 minutes on a Windows Server-based machine with dual 2.6 GHz Intel Xeon processors. Mean and max error results for the localization of the artifact centerline are shown in Table 2.

TABLE 2

Quantitative electrode artifact localization results.

| | Experiment | | | | | | | Overall |
|---|---|---|---|---|---|---|---|---|
| | 1 | 2 | 3 | 4 | 5 | 6 | 7 | Stats. |
| Mean Err (mm) | 0.157 | 0.185 | 0.182 | 0.190 | 0.235 | 0.203 | 0.214 | 0.195 |
| Max Err (mm) | 0.436 | 0.330 | 0.548 | 0.365 | 0.826 | 0.722 | 0.345 | 0.826 |

Figure 30:
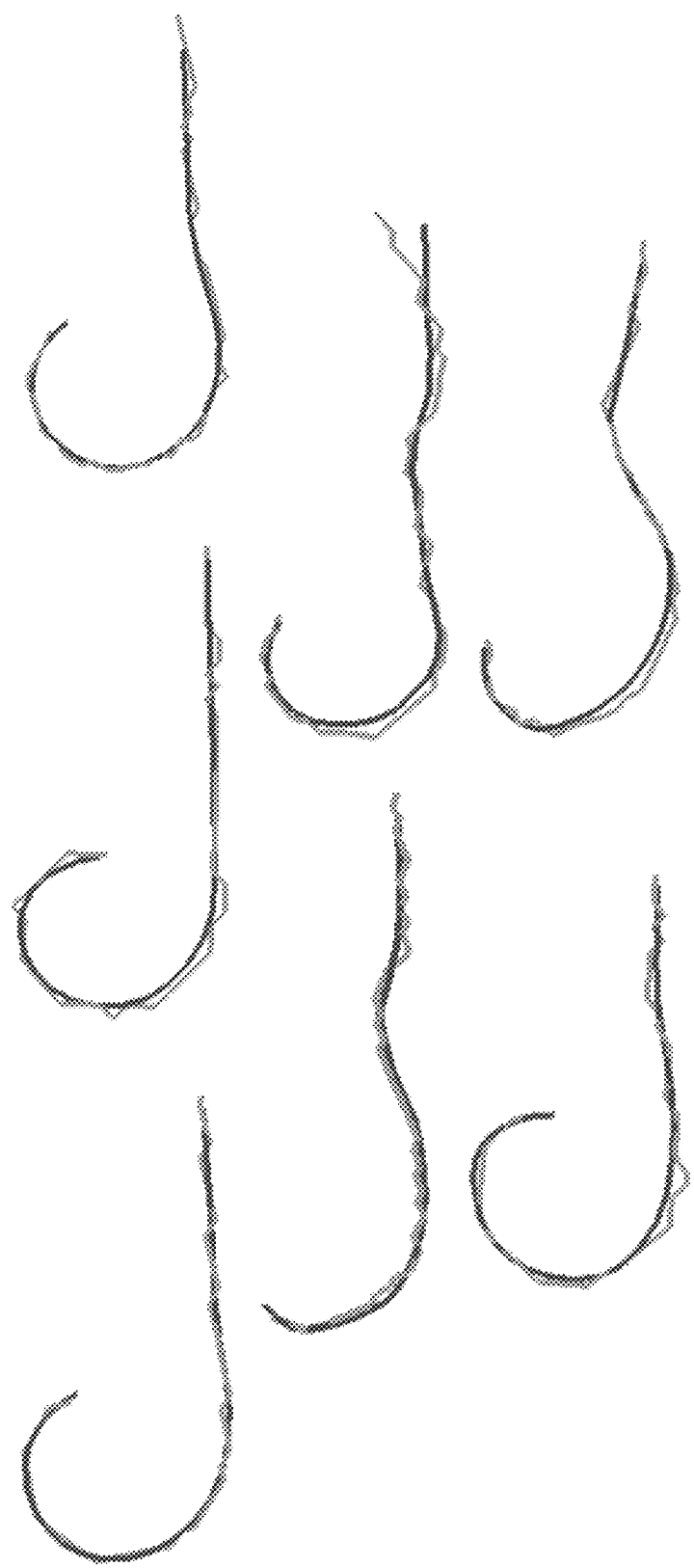
FIG. 30 shows renderings of electrode artifact localization results. Shown are the automatic (red) and manually (green) localized curves for experiments 1-7 (left-to-right, top-to-bottom).

It can be seen that all mean errors are under 0.3 mm (under 1 voxel's width), and that the maximum error is less than 0.9 mm (under 3 voxel's width). Renderings of these results are shown in FIG. 30. All results appear qualitatively accurate.

Surface reconstruction results of the experiments are shown in FIG. 31. In the figure, histological images can be seen in the left column. In the middle column are 3D renderings of the automatic reconstruction results. The scala tympani is rendered transparently in red to allow visualization of the relative position of the array. The cavity in which each contact is positioned and the modiolar proximity are assessed first by qualitatively examining the histological images (results shown as black line in the graphs), and then by examining the automatic 3D reconstructions (results shown as red-dashed line). Each electrode is labeled as being positioned within the scala tympani (ST) or scala vestibuli (SV), or in the case of experiment 4, the scala media (SM). Experiment 4 is representative of a particularly traumatic insertion, where the array became partially lodged underneath both the scala tympani and vestibuli in the region known as scala media. Modiolar proximity is qualified as being Medial (modiolar hugging), Lateral (far from the modiolus), or M/L (between medial and lateral). As can be seen from the graph, there is excellent agreement between the histological and reconstruction based assessments. The errors in cochlear depth are shown in Table 3.

TABLE 3

Depth error of array surface reconstructions.
Error is reported in number of electrodes.

| | Experiment No. | | | | | | |
|---|---|---|---|---|---|---|---|
| | 1 | 2 | 3 | 4 | 5 | 6 | 7 |
| Depth Error | 1 | 0 | 1 | 0 | 2 | 1 | 0 |

This is the error in the cochlear depth of the tip electrode measured in terms of number of electrodes. This was measured using the following process: Let the deeper of histological or reconstruction based views of the array be labeled D and the shallower of the two views be A. The error in cochlear depth is equal to the number of electrodes in D that are implanted deeper than A. As can be seen from the table, the worst disagreement in depth estimation is two electrodes, and several experiments result in perfect agreement.

According to the invention, this example presents the first method for determining the position of a cochlear implant electrode array in vivo that takes advantage of non-rigid models to produce highly accurate patient-specific reconstructions of cochlear anatomy. The methods employed for localizing the scalae have been shown in [35] to produce the most accurate patient-specific reconstructions of cochlear anatomy to date. Thus, the level of accuracy achievable with the proposed approach exceeds other approaches that rely on a rigid model of cochlear anatomy [68] or approaches that rely purely on an expert's visual assessment [69]. To the best of the knowledge, this work also presents the first approach for automatically segmenting, and generating a realistic 3D reconstruction of a cochlear implant array, which allows the position of the array to be easily assessed in an interactive 3D rendering environment. To validate these results, assessment of electrode position was conducted using the proposed approach and by examining histological results independently. This validation study has shown that the reconstructions are accurate, and thus could be useful in several applications.

The approach required manually tuning five weighting values. Two of these parameters, $w_4$ and $w_5$, assign lengths to the forward and normal forces of the centerline adjustment step. Choosing these values was accomplished simply by measuring the average disparities between the artifact position in CT and the array position in histological images. The other three parameters required tuning by observing the behavior of the algorithm on the testing volumes. Future work will include studying the sensitivity of the approach to the choice of parameters, as well as to explain the apparent disparity between the position of metallic artifact in CT and the histological assessment of electrode position.

Using the proposed approach to assess electrode positioning in live subjects, researchers will be able to correlate hearing restoration with data such as depth of insertion, in which cavity each contact is placed, and the modiolar proximity of each contact with a high degree of accuracy. Since the approach only requires an additional low dose CT, it should be possible to assess implant position, and establish correlation with hearing restoration, using a large number of patients.

In sum, the invention, among other things, discloses image processing techniques that can be used to detect, for the first time, the positions of implanted CI electrodes and the nerves they stimulate for individual CI users. These techniques permit development of new, customized CI stimulation strategies. Accordingly, the strategies leads to significant hearing improvement in an experiment conducted with a number of CI recipients. These results indicate that image-guidance can be used to improve hearing outcomes for many existing CI recipients without requiring additional surgical procedures.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the invention pertains without departing from its spirit and scope. Accordingly, the scope of the invention is defined by the appended claims rather than the foregoing description and the exemplary embodiments described therein.

REFERENCE LIST

[1]. "Cochlear Implants," National Institute on Deafness and Other Communication Disorders, No. 11-4798, 2011.
[2]. Rubenstein J. T., "How cochlear implants encode speech," Curr Opin Otolaryngol Head Neck Surg. 12(5): 444-8, 2004.
[3]. Wilson B. S., Dorman M. F., "Cochlear implants: Current designs and future possibilities," J. Rehab. Res. Dev. 45(5): 695-730, 2008.
[4]. Fu Q. J., Nogaki G., "Noise susceptibility of cochlear implant users: The role of spectral resolution and smearing," J Assoc Res Otolaryngol. 6(1):19-27, 2005.
[5]. Boex C, de Balthasar C., Kos M. I., Pelizzone M., "Electrical field interactions in different cochlear implant systems," J Acoust Soc Am 114:2049-2057, 2003.
[6]. Noble J. H., Labadie R. F., Majdani O., Dawant B. M., "Automatic segmentation of intra-cochlear anatomy in conventional C T", IEEE Trans. on Biomedical. Eng., 58(9): 2625-32, 2011.
[7]. Noble, J. H., Gifford, R. H., Labadie, R. F., Dawant, B. M., "Statistical Shape Model Segmentation and Frequency Mapping of Cochlear Implant Stimulation Targets in C T," N. Ayache et al. (Eds.): MICCAI 2012, Part II, LNCS 7511, pp. 421-428. 2012.
[8]. Noble, J. H., Schuman, A., Wright, C. G., Labadie, R. F., Dawant, B. M., "Automatic Identification of Cochlear Implant Electrode Arrays for Post-Operative Assessment," Proc. of the SPIE conf. on Med. Imag., 7962: 796217, 2011.
[9]. Wilson B. S., Finley C. C., Lawson, D. T., Wolford, R. D., Eddington, D. K., Rabinowitz, W. M., "Better speech recognition with cochlear implants," Nature 352, 236-238, 1991.
[10]. Stakhovskaya O., Spridhar D., Bonham B. H., Leake P. A., "Frequency Map for the Human Cochlear Spiral Ganglion: Implications for Cochlear Implants," J. Assoc. Res. Otol. 8: 220-33, 2007.
[11]. Friesen L. M., Shannon R. V., Baskent D., Wang X., "Speech recognition in noise as a function of the number of spectral channels: Comparison of acoustic hearing and cochlear implants," J. Acoust Soc Am. 110(2): 1150-63, 2001.
[12]. Garnham C., O'Driscoll M., Ramsden R., Saeed S., "Speech understanding in noise with a Med-El COMBI 40+ cochlear implant using reduced channel sets," Ear Hear. 23(6): 540-52, 2002.
[13]. Zwolan T. A., Collins L. M., Wakefiled G. H., "Electrode discrimination and speech recognition in postlingually deafened adult cochlear implant subjects," J. Acoust. Soc. Am. 102(6): 3673-85, 1997.
[14]. Garadat S. N., Zwolan T. A., Pfingst B. E., "Across-site patterns of modulation detection: Relation to speech recognition," J. Acoust. Soc. Am. 131(5): 4030-41, 2012.
[15]. Peterson G. E., Lehiste I., "Revised CNC lists for audiotory tests," J. Speech and Hear. Dis. 27: 62-70, 1962.
[16]. Spahr A. J., Dorman M. F., Litvak L. M., Van Wie S., Gifford R. H., Loizou P. C., Loiselle L. M., Oakes T., Cook S., "Development and validation of the AzBio sentence lists," Ear Hear. 33(1): 112-7, 2012.
[17]. Bench J., Kowal A., Bamford J., "The BKB (Bamford-Kowal-Bench) sentences lists for partially-hearing children," Br. J. Audiol. 13: 108-12, 1979.
[18]. Saoji A. A., Litvak L. M., Spahr A. J., Eddins D. A., "Spectral modulation detection and vowel and consonant identifications in cochlear implant listeners," J. Acoust. Soc. Am. 126 (3): 955-8, 2009.
[19]. Henry B. A., Turner C. W., "The resolution of complex spectral patterns by cochlear implant and normal-hearing listeners," J Acoust Soc Am 113(5):2861-73, 2003.
[20]. Drennan W. R., Won J. H., Nie K., Jameyson E., Rubinstein J. T., "Sensitivity of psychophysical measures to signal processor modifications in cochlear implant users," Hear Res 262: 1-8, 2010.
[21]. Wilcoxon, F., "Individual comparisons by ranking methods," Biometrics Bulletin 1 (6): 80-83, 1945.
[22]. Cox R. M., Alexander G. C., "The abbreviated profile of hearing aid benefit," Ear Hear. 16(2): 176-86, 1995.
[23]. Tyler R. S., Preece J. P., Lansing C. R., Otto S. R., Gantz B. J., "Previous experience as a confounding factor in comparing cochlear-implant processing schemes," J. Speech Hear. Res. 29: 282-7, 1986.
[24]. Rogers M., Graham J., "Robust Active Shape Model Search," ECCV 2002, LNCS, vol. 2353, pp. 517-53, 2002.
[25]. Cootes, T. F., Taylor, C. J., Cooper, D. H., Graham, J, "Active Shape Models—Their Training and Application," Comp. Vis. Image Unders. 61(1), 39-59, 1995.

[26]. Green, B. F., "The orthogonal approximation of an oblique structure in factor analysis," Psychometrika 17, 429-440, 1952.

[27]. Dice, L. R., "Measures of the amount of ecologic association between species," Ecology 26, 297-302, 1945.

[28]. Zijdenbos A. P., Dawant B. M., Margolin R., "Morphometric Analysis of White Matter Lesions in M R Images: Method and Validation," IEEE Trans. on Med. Imag. 13(4), 716-724, 1994.

[29]. Fechner G T, *Elemente der Psychophysik*. B. Rand, Ed. The Classical Psychologists (pp. 562-572). Boston: Houghton Mifflin, 1912.

[30]. Thornton, A. R., Raffin, M. J., "Speech-discrimination scores modeled as a binomial variable," J Speech Hear Res 21, 507-518, 1978.

[31]. Gifford R H, Shallop J K, Peterson A M., "Speech Recognition Materials and Ceiling Effects: Considerations for Cochlear Implant Programs," Audiol Neurotol, 13:193-205, 2008.

[32]. Aschendorff A, Kromeier J, Klenzner T, Laszig R, Quality Control After Insertion of the Nucleus Contour and Contour Advance Electrode in Adults. Ear & Hearing 28, 2007: 75S-79S.

[33]. Jethanamest D, Tan C T, Fitzgerald M B, Svirsky M A, A new software tool to optimize frequency table selection for cochlear implants. Otology & Neurotology 31(8), 2010: 1242-7.

[34]. Skinner M W, Holden T A, Whiting B R, Voie A H, Brundsden B, Neely J G, Saxon E A, Hullar T E, Finley C C. In vivo estimates of the position of advanced bionics electrode arrays in the human cochlea. Ann Otol Rhinol Laryngol Suppl. 197, 2007: 197:2-24.

[35]. Noble J H, Rutherford R, Labadie R F, Majdani O, Dawant B M. Modeling and segmentation of intra-cochlear anatomy in conventional C T. Proc. of the SPIE conf. on Med. Imag. 7623, 2010: 762302.

[36]. Rogers M, Graham J. Robust Active Shape Model Search. Lecture Notes in Computer Science—ECCV 2353, 2002: 517-530.

[37]. Asman, A. J. and B. A. Landman, Robust Statistical Label Fusion through Consensus Level, Labeler Accuracy and Truth Estimation (COLLATE). IEEE Transactions on Medical Imaging, In press 2011.

[38]. GreenWood D D. A cochlear frequency-position function for several species-29 years later. J. Acoust. Soc. Am. 87(6):2592-2605, 1990.

[39]. Cox R M, Alexander G C. (1995). The abbreviated profile of hearing aid benefit. Ear Hear. 16(2):176-86.

[40]. Drennan W R, Won J H, Nie K, Jameyson E, Rubinstein J T. (2010). Sensitivity of psychophysical measures to signal processor modifications in cochlear implant users. Hear Res. 262(1-2):1-8.

[41]. Gabrielsson A, Schenkman B N, Hagerman B. (1988). The effects of different frequency responses on sound quality judgments and speech intelligibility. J Speech Hear Res, 31(2): 166-77.

[42]. Hinderink J B, Krabbe P F, Van Den Broek P. (2000). Development and application of a health-related quality-of-life instrument for adults withcochlear implants: the Nijmegen cochlear implant questionnaire. Otolaryngol Head Neck Surg. 123(6):756-65.

[43]. Peterson G E, Lehiste I. (1962). Revised CNC lists for auditory tests. J Speech Hear Disord. 27:62-70.

[44]. Saoji A A, Litvak L, Spahr A J, Eddins D A. (2009). Spectral modulation detection and vowel and consonant identifications in cochlear implant listeners. J Acoust Soc Am. 126(3):955-8.

[45]. Spahr A J, Dorman M F, Litvak L M, Van Wie S, Gifford R H, Loizou P C, Loiselle L M, Oakes T, Cook S. (2011). Development and Validation of the AzBio Sentence Lists. Ear Hear. 2011 Aug. 8. [Epub ahead of print]

[46]. Won J H, Drennan W R, Nie K, Jameyson E M, Rubinstein J T. (2011). Acoustic temporal modulation detection and speech perception in cochlear implant listeners. J Acoust Soc Am. 130(1):376-88.

[47]. T. Zhang, T. Spahr, M. Dorman, "Spectral processing and speech recognition in bimodal implant users," Presented at the American Auditory Society Scientific and Technology Meeting, March, 2011.

[48]. de Bruijne, M., van Ginneken, B., Viergever, M. A., Niessen, W. J.: Adapting active shape models for 3D segmentation of tubular structures in medical images. In: Proc. Inf. Process. Med. Imaging, pp. 136-147. Springer (2003).

[49]. E. Lehnhardt and R. Laszig, "Specific surgical aspects of cochlear implant-soft surgery," *Adv. in coch. Imp.*, pp. 228-9, 1994.

[50]. C. James, K. Albegger, and R. Battmer, et. al, "Preservation of residual hearing with cochlear implantation: How and why," *Acta Oto-Laryngologica*, 125:5, pp. 481-91, 2005.

[51]. E. Erixon, H. Hogstorp, K. Wadin, and H. Rask-Anderson, "Variational anatomy of the human cochlea: implications for cochlear implantation," *Otology & Neurotology*, 30, pp. 14-22, 2008.

[52]. P. Dimopoulos, C. Muren, "Anatomic variations of the cochlea and relations to other temporal bone structures. *Acta Radiologica*, 31, pp. 439-44, 1990.

[53]. D. R. Ketten, M. W. Skinner, G. Wang, et al., "In vivo measure of cochlear length and insertion depth of nucleus cochlear implant electrode arrays," *Ann Otol Rhinol Laryngol Suppl.*, 175, pp. 1-16, 1998.

[54]. B. Escude, C. James, O. Dequine, N. Cochard, E. Eter, B. Fraysse, "The size of the cochlea and predictions of insertion depth angles for cochlear implant electrodes," *Audiol. Neurootol.*, 11 Suppl 1, pp. 27-33, 2006.

[55]. W. H. Press, B. P. Flannery, S. A. Teukolsky, and W. T. Vetterling, *Numerical Recipes in C, 2nd ed*. Cambridge, U. K.: Cambridge Univ. Press, 1992, ch. 10, pp. 412-419.

[56]. F. Maes, A. Collignon, D. Vandermeulen, G. Marchal, and P. Suetens, "Multimodality image registration by maximization of mutual information," *IEEE Trans Med Imag.* 16, pp. 187-198, 1997.

[57]. G. K. Rohde, A. Aldroubi, B. M. Dawant, "The adaptive bases algorithm for intensity-based nonrigid image registration," *IEEE Trans. Med. Imag.*, 22, pp. 1470-1479, 2003.

[58]. Z. Wu, "Multivariate compactly supported positive definite radial functions," *Adv. Comput. Math.* 4, 283-292, 1995.

[59]. C. Studholme, D. L. G. Hill and D. J. Hawkes, "An overlap invariant entropy measure of 3D medical image alignment," *Pattern Recognition* 32; 1, pp. 71-86, 1999.

[60]. Frangi, A. F., Rueckert, D., Schnabel, J. A., Niessen, W. J., "Automatic construction of multiple-object three-dimensional statistical shape models: Application to cardiac modeling," *IEEE Trans on Med. Imag.*, Vol. 21, No. 9, pp. 1151-66, 2002.

[61]. Arun, K. S., Huang, T. S., and Blostein, S. D., "Least square fitting of two 3-D point sets," *IEEE Trans. Patt. Anal. Machine Intell*. Vol. 9, no. 5, pp. 698-700, 1987.

[62]. Schuman T A, Noble J H, Wright C G, Wanna G B, Dawant B, Labadie, R F. "Anatomic Verification of a Novel, Non-rigid Registration Method for Precise Intrascalar Localization of Cochlear Implant Electrodes in Adult Human Temporal Bones Using Clinically-available Computerized Tomography." *Laryngoscope,* 120 (11), pp. 2277-2283, 2010.

[63]. Wanna, G., Noble, J. H., Mcrackan, T., Dawant, B. M., Dietrich, M., Watkins, L., Rivas, A., Schuman, T., Labadie, R., "Assessment of electrode positions and hearing outcome in bilateral cochlear implant patients," *Otology & Neurotology,* 32 (3), pp. 428-432, 2011.

[64]. Finley, C. C., Holden, T. A., Holden, L. K., Whiting, B. R., Chole, R. A., Neely, G. J., Hullar, T. E., & Skinner, M. W. (2008). Role of electrode placement as a contributor to variability in cochlear implant outcomes. *Otology & Neurotology,* 29(7), 920-928.

[65]. Labadie, R. F., Balachandran, R., Mitchell, J., Noble, J. H., Majdani, O., Haynes, D. S., Bennett, M., Dawant, B. M., Fitzpatrick, J. M., 2010, "Clinical Validation Study of Percutaneous Cochlear Access Using Patient Customized Micro-Stereotactic Frames," *Otology & Neurotology,* 31(1):94-99.

[66]. C. Xu, J. L. Prince, "Snakes, shapes, and gradient vector flow," IEEE Trans. on Image Processing, 7(3): 259-69, 1998.

[67]. M. Kass, A. Witkin, D. Terzopoulos, "Snakes: Active Contour Models," Int'l Jour. Of Computer Vision, 321-331, 1988.

[68]. M. W. Skinner, T. A. Holden, B. R. Whiting, et. al, "In vivo estimates of the position of advanced bionics electrode arrays in the human cochlea," *Ann Otol Rhinol Laryngol Suppl.,* 197:2-24, April 2007.

[69]. A. Aschendorff, J. Kromeier, T. Klenzner, and R. Laszig, "Quality Control After Insertion of the Nucleus Contour and Contour Advance Electrode in Adults", Ear & Hearing, 28, 75S-79S, April 2007.

What is claimed is:

1. A method for customizing cochlear implant stimulation of a living subject, wherein the cochlear implant comprises an electrode array having a plurality of electrodes implanted in a cochlea of the living subject, comprising the steps of:
   (a) identifying a spiral ganglion (SG) neural region that is targeted for stimulation and its corresponding modiolar interface and determining a position for each of the plurality of electrodes relative to the SG neural region, wherein each electrode has a distance relative to a closest stimulation point on the SG neural region, and the SG has a characteristic frequency corresponding to each closest stimulation point;
   (b) constructing a tonotopic map of the modiolar interface to have a tonotopically mapped modiolar interface;
   (c) determining a geometric relationship between the tonotopically mapped modiolar interface and each of the plurality of electrodes by an electrode distance-vs-frequency curve showing the distance from each frequency mapped region of the SG to each electrode; and
   (d) configuring one or more electrodes of the electrode array to stimulate a region of the modiolar interface based on the position of the one or more electrodes and their geometric relationship with the tonotopically mapped modiolar interface.

2. The method of claim 1, wherein the step of identifying the SG neural region comprises the step of constructing a statistical shape model (SSM) of cochlear anatomy that includes the SG from a set of CT image volumes of cochlea.

3. The method of claim 2, wherein the set of CT image volumes of cochlea comprises μCT image volumes of cochlea, wherein in each μCT image volume, structures of the scala vestibuli, scala tympani, and SG are manually segmented.

4. The method of claim 3, wherein, prior to constructing the SSM, the step of identifying the SG neural region further comprises the steps of:
   (a) identifying points in the manual segmentation that correspond to strong cochlear edges in each CT image volume; and
   (b) assigning the identified points a weight of 1, and all the other points in the manual segmentation a weight of 0.01.

5. The method of claim 4, wherein the step of constructing the SSM comprises the steps of:
   (a) establishing a point correspondence between surfaces of the structures that are manually segmented in each CT image volume;
   (b) registering the surfaces to each other with a seven degrees of a freedom similarity transformation by using the points; and
   (c) computing eigenvectors of the registered points' covariance matrix.

6. The method of claim 5, wherein the step of establishing the point correspondence between the structure surfaces comprises the steps of:
   (a) mapping a set of CT image volumes to one of the CT image volumes chosen as a reference volume by using a non-rigid registration; and
   (b) registering surfaces of each CT image volume to the surface of the reference volume, so as to establish the correspondence between each point on the reference surface with the closest point in each of the registered CT image surfaces.

7. The method of claim 6, wherein during constructing the SSM, a set of SG points in the SSM that interfaces with intra-cochlear anatomy is identified, wherein the set of SG points is located in an active region (AR) to be stimulated.

8. The method of claim 7, wherein the step of constructing the tonotopic map of the modiolar interface comprises the steps of:
   (a) tonotopic mapping each SG point in the AR of the reference volume by using equations relating cochlear place frequency and angular depth; and
   (b) once segmentation is completed, transferring tonotopic frequency labels from the SSM to a target image.

9. The method of claim 8, wherein the step of determining the position for each of the plurality of electrodes comprises the step of:
   (a) identifying a centerline of an image artifact created by the electrode array; and
   (b) sampling points representing the center of each electrode along the centerline to identify the position for each of the plurality of electrodes.

10. The method of claim 9, wherein the step of determining the position for each of the plurality of electrodes comprises the step of projecting the position for each of the plurality of electrodes and the SG into the same space by using a transformation that registers the pre-operative and post-operative CTs of the living subject.

11. The method of claim 5, wherein the step of constructing the SSM further comprises the step of constructing a point distribution model (PDM) on the registered manual segmentation surfaces for weighted active shape model (wASM) segmentation by using the weights, so that the SSM is built as a standard PDM computed on the registered exemplar point sets.

12. The method of claim 1, wherein the step of determining the position for each of the plurality of electrodes relative to the SG neural region comprises the step of:
identifying the position for each of the plurality of electrodes relative to the tonotopically mapped modiolar interface in vivo.

13. The method of claim 1, further comprising the step of using the geometric relationship between the electrodes and the modiolar interface to detect when at least one electrode of the electrode array interferes with the others.

14. The method of claim 13, further comprising the step of deactivating at least one electrode of the electrode array if it interferes with other electrodes.

15. The method of claim 1, wherein the step of configuring one or more electrodes of the electrode array to stimulate comprises the step of assigning a frequency band to the one or more electrodes of the electrode array for stimulation.

16. The method of claim 1, wherein the step of configuring one or more electrodes of the electrode array to stimulate comprises the step of adjusting a strength of an input to the one or more electrodes to produce an electric field that is tailored to stimulate specific areas on the tonotopically mapped modiolar interface using the position of the one or more electrodes on the distance-to-frequency curve.

17. The method of claim 1, wherein the step of configuring one or more electrodes of the electrode array to stimulate comprises the step of adjusting a strength of an input to the one or more electrodes to produce an electric field that is tailored to stimulate specific areas on the tonotopically mapped modiolar interface using the position of the one or more electrodes on the electrode distance-vs-frequency curve and inner ear tissue-specific conductivity values.

18. The method of claim 1, wherein the electrode distance-vs-frequency curve is labeled and indicates which electrode is the closest in a frequency region spanned by that segment.

19. A system for customizing cochlear implant stimulation of a living subject, wherein the cochlear implant comprises an electrode array having a plurality of electrodes implanted in a cochlea of the living subject, comprising a controller configured to perform functions of:
(a) identifying a spiral ganglion (SG) neural region that is targeted for stimulation and its corresponding modiolar interface and determining a position for each of the plurality of electrodes relative to the SG neural region, wherein each electrode has a distance relative to a closest stimulation point on the SG neural region, and the SG has a characteristic frequency corresponding to each closest stimulation point;
(b) constructing a tonotopic map of the modiolar interface to have a tonotopically mapped modiolar interface;
(c) determining a geometric relationship between the tonotopically mapped modiolar interface and each of the plurality of electrodes by an electrode distance-vs-frequency curve showing the distance from each frequency mapped region of the SG to each electrode; and
(d) configuring one or more electrodes of the electrode array to stimulate a region of the modiolar interface based on the position of the one or more electrodes and their geometric relationship with the tonotopically mapped modiolar interface.

20. A non-transitory tangible computer-readable medium storing instructions which, when executed by one or more processors, cause a system to perform functions for customizing cochlear implant stimulation of a living subject, wherein the cochlear implant comprises an electrode array having a plurality of electrodes implanted in a cochlea of the living subject, the functions comprising:
(a) identifying a spiral ganglion (SG) neural region that is targeted for stimulation and its corresponding modiolar interface and determining a position for each of the plurality of electrodes relative to the SG neural region, wherein each electrode has a distance relative to a closest stimulation point on the SG neural region, and the SG has a characteristic frequency corresponding to each closest stimulation point;
(b) constructing a tonotopic map of the modiolar interface to have a tonotopically mapped modiolar interface;
(c) determining a geometric relationship between the tonotopically mapped modiolar interface and each of the plurality of electrodes by an electrode distance-vs-frequency curve showing the distance from each frequency mapped region of the SG to each electrode; and
(d) configuring one or more electrodes of the electrode array to stimulate a region of the modiolar interface based on the position of the one or more electrodes and their geometric relationship with the tonotopically mapped modiolar interface.

\* \* \* \* \*

UNITED STATES PATENT AND TRADEMARK OFFICE
CERTIFICATE OF CORRECTION

PATENT NO. : 9,572,981 B2
APPLICATION NO. : 14/390503
DATED : February 21, 2017
INVENTOR(S) : Jack H. Noble et al.

It is certified that error appears in the above-identified patent and that said Letters Patent is hereby corrected as shown below:

In the Specification

Column 1, Lines 41-47: reading "This invention was made with government support under grant numbers R01DC008408, R01DC009404, R21DC012620 and F31DC009791 awarded by the National Institute on Deafness and Other Communication Disorders, and UL1TR000011 awarded by the National Center for Advancing Translational Sciences. The government has certain rights in the invention."

Should read as follows:
-- This invention was made with government support under grant numbers DC008408, DC009791, DC009404, DC012620, and TR000011 awarded by the National Institutes of Health. The government has certain rights in the invention. --

Signed and Sealed this
Nineteenth Day of November, 2019

Andrei Iancu
*Director of the United States Patent and Trademark Office*